US009271894B2

(12) United States Patent
Nakamura

(10) Patent No.: US 9,271,894 B2
(45) Date of Patent: *Mar. 1, 2016

(54) CARBON DIOXIDE GAS MIST PRESSURE BATH APPARATUS FOR PREVENTING, IMPROVING OR CURING MYOCARDIAL INFARCTION

(75) Inventor: Shoichi Nakamura, Nagano (JP)

(73) Assignees: ADVANCE BIOTRON CO., LTD., Higashichikuma-gun, Nagano (JP); Shoichi Nakamura, Higashichikuma-gun, Nagano (JP)

( * ) Notice: Subject to any disclaimer, the term of this patent is extended or adjusted under 35 U.S.C. 154(b) by 433 days.

This patent is subject to a terminal disclaimer.

(21) Appl. No.: 13/701,748

(22) PCT Filed: Dec. 20, 2011

(86) PCT No.: PCT/JP2011/079485

§ 371 (c)(1),
(2), (4) Date: Dec. 3, 2012

(87) PCT Pub. No.: WO2012/086635

PCT Pub. Date: Jun. 28, 2012

(65) Prior Publication Data

US 2013/0072863 A1 Mar. 21, 2013

(30) Foreign Application Priority Data

Dec. 20, 2010 (JP) ................................ 2010-283831

(51) Int. Cl.
*A61M 37/00* (2006.01)
*A61H 33/14* (2006.01)
(Continued)

(52) U.S. Cl.
CPC ................ *A61H 33/14* (2013.01); *A61H 33/02* (2013.01); *A61H 33/066* (2013.01); *A61H 35/00* (2013.01);
(Continued)

(58) Field of Classification Search
CPC .................. A61H 2033/145; A61H 2035/004; A61H 2201/105; A61H 2201/5007; A61H 2201/5071; A61H 2201/5089; A61H 33/02; A61H 33/14; A61H 35/00; A61M 35/00; A61B 19/38
USPC ...................................................... 604/23, 24
See application file for complete search history.

(56) References Cited

U.S. PATENT DOCUMENTS

2010/0286750 A1 11/2010 Nakamura
2012/0172788 A1 * 7/2012 Torok et al. ..................... 604/24
2013/0079703 A1 * 3/2013 Nakamura ............. A61H 33/14 604/24

FOREIGN PATENT DOCUMENTS

JP H07-171189 A 7/1995
JP 2006-263253 10/2006

(Continued)

OTHER PUBLICATIONS

PCT, "International Search Report for PCT/JP2011/079485", Jan. 31, 2012.

*Primary Examiner* — Emily Schmidt
*Assistant Examiner* — Deanna K Hall
(74) *Attorney, Agent, or Firm* — Manabu Kanesaka

(57) ABSTRACT

A carbon dioxide gas mist pressure bath apparatus for preventing, improving or curing a myocardial infarction by contacting a carbon dioxide gas mist to a skin and a mucous membrane of a living organism directly or through a clothing, thereby to improve or promote a circulation of a blood, includes a carbon dioxide gas mist-enclosing unit for enclosing the living organism; a gas supply unit for supplying a carbon dioxide gas; a carbon dioxide gas mist generating and supplying unit for pulverizing and dissolving the carbon dioxide gas into a liquid, and supplying the carbon dioxide gas mist into the carbon dioxide gas mist-enclosing unit; an exhausting device for exhausting the gas in the carbon dioxide gas mist-enclosing unit to an outside thereof; and a control device for controlling a supplying amount of the carbon dioxide gas mist from the carbon dioxide gas mist generating and supplying unit.

11 Claims, 50 Drawing Sheets

(51) Int. Cl.

| | |
|---|---|
| ***A61H 33/02*** | (2006.01) |
| ***A61H 33/06*** | (2006.01) |
| ***A61H 35/00*** | (2006.01) |
| *A61H 33/04* | (2006.01) |

(52) U.S. Cl.

CPC ..... *A61H 2033/048* (2013.01); *A61H 2033/145* (2013.01); *A61H 2035/004* (2013.01); *A61H 2201/0161* (2013.01); *A61H 2201/0173* (2013.01); *A61H 2201/0207* (2013.01); *A61H 2201/105* (2013.01); *A61H 2201/5007* (2013.01); *A61H 2201/5043* (2013.01); *A61H 2201/5071* (2013.01); *A61H 2201/5082* (2013.01); *A61H 2201/5089* (2013.01)

(56) References Cited

FOREIGN PATENT DOCUMENTS

| | | | |
|---|---|---|---|
| JP | 2009-183625 | A | 8/2009 |
| JP | 3163836 | U | 11/2010 |
| JP | 3163837 | U | 11/2010 |
| WO | WO 2009/157538 | A1 | 12/2009 |

* cited by examiner (a)

(b)

Volume of deoxygenated blood in tissue (Volume of deoxyhemoglobin)

Volume of total blood in tissue (Volume of total hemoglobin)

Changes in pH in tissue

Ejection rate (EF) of heart left ventricle

** $P<0.01$ vs control

† $P<0.05$ vs M, ‡ $P<0.01$ vs M

C: control, NM: no $CO_2$ gas mist therapy,
M: $CO_2$ gas mist therapy,
M+L: $CO_2$ gas mist therapy + L-NAME Terminal diameter (LVDd) of expansion of heart left ventricle

* P<0.05 vs control, ** P<0.01 vs control

† P<0.05 vs M

C: control, NM: no $CO_2$ gas mist therapy,
M: $CO_2$ gas mist therapy,
M+L: $CO_2$ gas mist therapy + L-NAME Terminal diameter (LVDs) of contraction of heart left ventricle

* $P<0.05$ vs control, ** $P<0.01$ vs control

† $P<0.05$ vs M

C: control, NM: no $CO_2$ gas mist therapy,
M: $CO_2$ gas mist therapy,
M+L: $CO_2$ gas mist therapy + L-NAME

* $P<0.05$ vs control, ** $P<0.01$ vs control

† $P<0.05$ vs M, ‡ $P<0.01$ vs M

C: control, NM: no $CO_2$ gas mist therapy,
M: $CO_2$ gas mist therapy,
M+L: $CO_2$ gas mist therapy + L-NAME Attenuation times of E wave C: control, NM: no $CO_2$ gas mist therapy,
M: $CO_2$ gas mist therapy,
M+L: $CO_2$ gas mist therapy + L-NAME

* $P<0.05$ vs control, ** $P<0.01$ vs control
† $P<0.05$ vs M, ‡ $P<0.01$ vs M

* P<0.05 vs control, ** P<0.01 vs control

‡ P<0.01 vs M

C: control, NM: no $CO_2$ gas mist therapy,
M: $CO_2$ gas mist therapy,
M+L: $CO_2$ gas mist therapy + L-NAME

* P<0.05 vs control, ** P<0.01 vs control

‡ P<0.01 vs M

C: control, NM: no $CO_2$ gas mist therapy,
M: $CO_2$ gas mist therapy,
M+L: $CO_2$ gas mist therapy + L-NAME Nitrate ion ($NO_3^-$) of blood serum C: control, NM: no $CO_2$ gas mist therapy,
M: $CO_2$ gas mist therapy,
M+L: $CO_2$ gas mist therapy + L-NAME † $P<0.05$ vs M, ‡ $P<0.01$ vs M Skin growth factor (VEGF) in blood vessel of blood serum C: control, NM: no $CO_2$ gas mist therapy,
M: $CO_2$ gas mist therapy,
M+L: $CO_2$ gas mist therapy + L-NAME † $P<0.05$ vs M, ‡ $P<0.01$ vs M Skin growth factor (VEGF) in blood vessel of myocardium
(Critical myocardium)

C: control, NM: no $CO_2$ gas mist therapy,
M: $CO_2$ gas mist therapy,
M+L: $CO_2$ gas mist therapy + L-NAME

* $P<0.05$ vs control, † $P<0.05$ vs M

** $P<0.01$ vs control

† $P<0.05$ vs M, ‡ $P<0.01$ vs M

C: control, NM: no $CO_2$ gas mist therapy,
M: $CO_2$ gas mist therapy,
M+L: $CO_2$ gas mist therapy + L-NAME C: control, NM: no $CO_2$ gas mist therapy,
M: $CO_2$ gas mist therapy,
M+L: $CO_2$ gas mist therapy + L-NAME C: control, NM: no $CO_2$ gas mist therapy,
M: $CO_2$ gas mist therapy,
M+L: $CO_2$ gas mist therapy + L-NAME

* $P<0.05$ vs control, ** $P<0.01$ vs control

‡ $P<0.01$ vs M

C: control, NM: no $CO_2$ gas mist therapy,
M: $CO_2$ gas mist therapy,
M+L: $CO_2$ gas mist therapy + L-NAME EIC chromatograph of $CO_2$ standard solution (equivalent to concentration 500 pg/p in specimen) [m/z44 (upper) and m/z45 (lower)]

$^{12}CO_2$ analytical curve (m/z44)

Sample: EIC chromatograph of non-treated plasma (No.1) [m/z 44 (upper), m/z45 (lower)]

Sample: EIC chromatograph of non-treated plasma (No.2) [m/z 44 (upper), m/z45 (lower)]

Sample: EIC chromatograph of $^{13}CO_2$ mist treated plasma (No.1) [m/z 44 (upper), m/z45 (lower)]

Sample: EIC chromatograph of $^{13}CO_2$ mist treated plasma (No.2) [m/z 44 (upper), m/z45 (lower)]

Sample: EIC chromatograph of non-treated heart (No.1) [m/z 44 (upper), m/z45 (lower)]

Sample: EIC chromatograph of non-treated heart (No.2) [m/z 44 (upper), m/z45 (lower)]

Sample: EIC chromatograph of $^{13}CO_2$ mist treated heart (No.1) [m/z 44 (upper), m/z45 (lower)]

Sample: EIC chromatograph of $^{13}CO_2$ mist treated heart (No.2) [m/z 44 (upper), m/z45 (lower)]

Sample: EIC chromatograph of non-treated liver (No.1) [m/z 44 (upper), m/z45 (lower)]

Sample: EIC chromatograph of non-treated liver (No.2) [m/z 44 (upper), m/z45 (lower)]

Sample: EIC chromatograph of $^{13}CO_2$ mist treated liver (No.1) [m/z 44 (upper), m/z45 (lower)]

Sample: EIC chromatograph of $^{13}CO_2$ mist treated liver (No.2) [m/z 44 (upper), m/z45 (lower)]

Sample: EIC chromatograph of non-treated muscle (No.1) [m/z 44 (upper), m/z45 (lower)]

Sample: EIC chromatograph of non-treated muscle (No.2) [m/z 44 (upper), m/z45 (lower)]

Sample: EIC chromatograph of $^{13}CO_2$ mist treated muscle (No.1) [m/z 44 (upper), m/z45 (lower)]

Sample: EIC chromatograph of $^{13}CO_2$ mist treated muscle (No.2) [m/z 44 (upper), m/z45 (lower)]

CARBON DIOXIDE GAS MIST PRESSURE BATH APPARATUS FOR PREVENTING, IMPROVING OR CURING MYOCARDIAL INFARCTION

RELATED APPLICATIONS

The present application is National Phase of International Application No. PCT/JP2011/079485 filed Dec. 20, 2011, and claims priority from Japanese Application No. 2010-283831, filed Dec. 20, 2010.

TECHNICAL FIELD

The present invention relates to a carbon dioxide gas mist pressure bath apparatus in a manner of contacting carbon dioxide to a skin and mucous membrane of a living organism directly or through clothing under a predetermined condition for improving or promoting circulation of the blood in the myocardial region, thereby to prevent, improve or cure myocardial infarction.

BACKGROUND OF THE INVENTION

Carbon dioxide (carbonic acid anhydride: CO2) has properties of being not only soluble in water (water-soluble) but also soluble in fat (fat-soluble) together, and therefore it has conventionally been known that, if carbon dioxide contacts the skin and mucous membrane of the living organism having both properties of water and fat, carbon dioxide penetrates under a subcutaneous layer of the living organism and expands blood vessels around penetrated parts of carbon dioxide, and works to improve the blood circulation.

Further, if penetrating subcutaneously, carbon dioxide has possibilities of displaying various physiological effects such as expanding the blood vessels, accelerating the blood circulation, dropping blood pressure, improving metabolism or accelerating to remove pain substance or waste products. In addition, it has also anti-inflammation and anti-bacterial. Therefore, carbon dioxide has recently been given attentions also from viewpoints of improving health or beauty other than the purpose of medical cares.

In the organization of the living organism, carbon dioxide works to release oxygen having been carried in combination with hemoglobin in a red blood cell. Around parts at the high concentration of carbon dioxide, the red blood cell releases more oxygen. Thus, supply of oxygen to cells by the red blood cell is mainly controlled by carbon dioxide. In short, being without carbon dioxide, hemoglobin remains as having been combined with oxygen and the cell becomes unable to receive oxygen. Carbon dioxide serves to play in fact very important roles also in metabolism within the living organism. Thus, carbon dioxide is not mere waste products resulted from energy action of the cell, and it has gradually cleared that carbon dioxide exerts various important services in the living organism.

Then, for causing carbon dioxide to be absorbed directly in the skin and mucous membrane of the living organism, various apparatuses have been proposed such as utilization of bath agents for generating carbon dioxide in hot water of a bathtub (for example, refer to patent documents 1 to 3).

RELATED PRIOR ART TECHNICAL DOCUMENTS

Patent Documents

Patent Document 1: Japanese Patent Application Publication No. 7-171189

Patent Document 2: Japanese Patent Application Publication No. 2006-263253

Patent Document 3: Japanese Patent Application Publication No. 2009-183625

SUMMARY OF THE INVENTION

Problems that the Invention is to Solve

In view of various known physiological actions in the living organism as above mentioned of carbon dioxide, in particular, blood circulation effects, blood vessel expansion effects or hyper metabolism effects, an inventor of this invention considered that in case continuously contacting carbon dioxide to the living organism, this action would be effective in improvement or acceleration of blood circulation in an ischemic region. That is, carbon dioxide penetrating under the skin is taken into a tissue (muscle) or the blood.

Blood much containing carbon dioxide is recognized as a condition of so-called "oxygen deficiency", and it expands the blood vessels, accelerates to increase blood flow, and at a myocardial infarction affected part, it improves infarction of the blood vessel and concurrently also urges to form new blood vessels (new formation of the blood vessel). It is considered that such blood accelerates metabolism by using $CO_2$ within the tissue, and supports new formation of the blood vessel.

As a result of the inventor's various experiments, it has been found that, only by contacting carbon dioxide to the skin and mucous membrane of the living organism, the concentration of carbon dioxide taken into blood was low, and until carbon dioxide in blood got to the heart, blood was much nullified on the way, so that a manner of only contacting carbon dioxide to the skin and mucous membrane of the living organism did not bring about effects in improving or curing myocardial infarction.

Therefore, the inventor has discovered that, for taking carbon dioxide effectively into blood, carbon dioxide is changed into a form of a mist, that is, such a condition is prepared that carbon dioxide is shut into bubbles of a thin skin of liquid (called it as "carbon dioxide gas mist" in this invention), and predetermined pressure (higher than internal pressure of the living organism) is added to contact the skin and mucous membrane of the living organism, so that concentration of carbon dioxide taken in blood is heightened, the ischemic region at a myocardial infarction affected part is improved and at the same time, blood vessel of myocardium is expanded and the condition of an infarction is improved.

Means of Solving the Problems

Thus, the present invention is to provide a carbon dioxide gas mist pressure bath method which causes carbon dioxide to contact directly or through clothing the skin and mucous membrane of a living organism, thereby to improve or promote circulation of blood in the myocardial region, and furthermore to prevent, improve or cure myocardial infarction, characterized by having following steps (a) to (d) being continued at least once per day for four weeks, that is, a step (a) of producing a carbon dioxide gas mist by pulverizing and dissolving carbon dioxide gas into a liquid, and forming this liquid into a mist; a step (b) of spraying the carbon dioxide gas mist into a carbon dioxide gas mist-enclosing means for enclosing the living organism under an air tight condition, a step (c) of expelling gas existing in the carbon dioxide gas mist-enclosing means into the outside, if necessary in parallel with the step (b), in order to maintain the pressure of gas within the carbon dioxide gas mist-enclosing means at or above a prescribed value being higher than the atmospheric pressure, and a step (d) of continuing such a step of supplying, for at least 20 minutes, the carbon dioxide mist into the carbon dioxide gas mist-enclosing means.

By the way, the invention calls it as "pulverizing and dissolving" to pulverize the liquid into fine liquid drops, and cause to contact and mix with gas (carbon dioxide).

In the meantime, the step (d) is characterized in that while measuring the concentration of the carbon dioxide gas mist existing in the carbon dioxide gas mist-enclosing means, the carbon dioxide gas mist continues to supply the carbon dioxide gas mist for at least 20 minutes.

Further, the above step (d) is characterized by controlling the supply amount of the carbon dioxide gas mist such that air pressure within the carbon dioxide gas mist-enclosing means is at a predetermined value.

The carbon dioxide gas mist is characterized by containing such carbon dioxide gas mist of not more than 10 μm in diameter. In addition, air pressure within the carbon dioxide gas mist-enclosing means in the step (c) is characterized by being 1.01 to 2.5 air pressure. The concentration of the carbon dioxide gas mist within the carbon dioxide gas mist-enclosing means in the step (d) is characterized by being 60% or more.

Further, the present invention relates to a carbon dioxide gas mist pressure bath apparatus for preventing, improving or curing myocardial infarction by contacting the carbon dioxide gas mist to the skin and mucous membrane of the living organism directly or through clothing, thereby to improve or promote circulation of the blood, characterized by furnishing a carbon dioxide gas mist enclosing-means for enclosing the living organism under a sealing condition; a carbon dioxide gas mist generating and supplying means for pulverizing and dissolving carbon dioxide into a liquid, generating a carbon dioxide gas under a mist state, and supplying the carbon dioxide gas mist into the carbon dioxide gas mist-enclosing means; an exhausting means for exhausting outside gas in the carbon dioxide gas mist-enclosing means; and a control device for, while exhausting outside gas in the carbon dioxide gas mist-enclosing means, controlling, if necessary, the supplying amount of the carbon dioxide gas mist from the carbon dioxide gas mist generating and supplying means, such that air pressure within the carbon dioxide gas mist enclosing means is set within a predetermined range.

Herein, the carbon dioxide gas mist pressure bath apparatus is characterized by further providing a concentration detecting means for measuring the concentration of the carbon dioxide gas mist in the carbon dioxide gas mist-enclosing means, and the control means controls the supply amount of the carbon dioxide gas mist such that the concentration of the carbon dioxide gas mist is at a predetermined value or more. In addition, an air pressure detecting means is further provided for measuring air pressure in the carbon dioxide gas mist-enclosing means, and the control means is characterized by controlling the supply amount of the carbon dioxide gas mist such that the concentration of the carbon dioxide gas mist is at a predetermined value or more.

The carbon dioxide gas mist-enclosing means is a foldable cover type, a bag type or a fixedly stationary box type. Herein, the carbon dioxide gas mist-enclosing means is characterized by furnishing a carbon dioxide gas mist inlet port having inside a check valve, an outlet port of discharging an inside gas, a doorway for getting in and out the living body, and an open for exposing the head of the living body. The open has a leakage prevention means for the carbon dioxide gas mist leaking from a space between the open and the living body.

Effects of the Invention

As will be explained in detail, the invention obtained test results of various animal tests concerning improvement or acceleration of the blood circulation in the myocardial region, and contacted the carbon dioxide gas mist of concentration being not less than a predetermined value to the skin and mucous membrane of the living organism for more than a predetermined period, so that a heart re-modeling depression effect not depending on blood kinetics has been recognized, and therefore it has been confirmed that the invention would be a new curing method of cardiac failure after myocardial infarction.

Further, by treatment of the invention, it has been confirmed that nitrate ion in blood ($NO_3^-$) increases significantly. That is, $NO_3^-$ is a comparatively stable oxidation metabolism derived from NO (nitrogen monoxide) being an entity of relaxation factor EDRF derived from endothelial cell in blood, and since NO is discharged from an endothelial cell of blood vessel, a blood flow improving effect by the carbon dioxide gas mist treatment of high concentration (80 to 100%) or the heart re-modeling depression effect has been distinctly suggested in that the endothelial function of blood vessel takes part in.

Many results of animal tests concerning improvements of diseases in the myocardial infarction described in the specification of this invention are concerned mainly with wistar rats aged of 8 weeks, and can be applied to human bodies and the living organisms of other mammalian as evidently from correlation with many other experimental examples and clinical data.

EMBODIMENTS FOR PRACTICING THE INVENTION

In the following description, explanations will be made to the embodiments of this invention, referring to the attached drawings.

At first, explanation will be made to the carbon dioxide gas mist pressure bath method of promoting blood circulation by contacting the carbon dioxide gas mist to the skin and mucous membrane of the living organism through either direct contact or contact through a clothing, thereby to prevent, improve or curing myocardial infarction.

Figure 1:
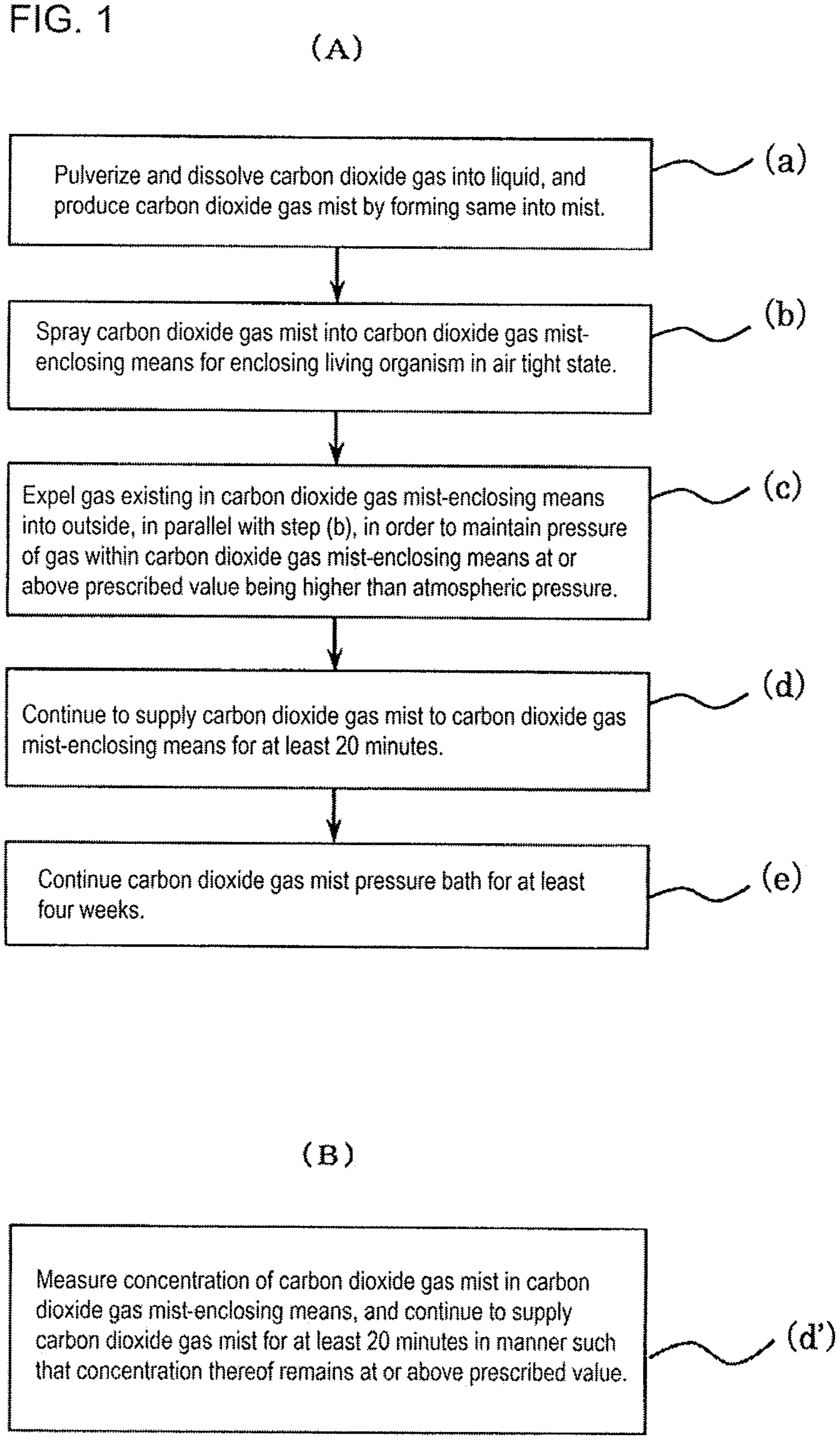
FIG. 1 Drawings showing the process flows of the carbon dioxide gas mist pressure bath method for preventing, improving or curing myocardial infarction of the living body depending on the present invention.

FIG. 1 shows process flows of the carbon dioxide gas mist pressure bath method for preventing, improving or curing myocardial infarction in the living organism. As shown in (A) part of FIG. 1, by use of a carbon dioxide gas mist generating and supplying apparatus which will be explained in detail later (in FIGS. 2 and 5), as shown in (A) part of FIG. 1, this invention is to provide a carbon dioxide gas mist pressure bath method having a step (a) of producing a carbon dioxide gas mist by pulverizing and dissolving carbon dioxide gas into a liquid, and forming this liquid into a mist; a step (b) of spraying the carbon dioxide gas mist into a carbon dioxide gas mist-enclosing means for enclosing the living organism under an air tight condition, a step (c) of expelling gas existing in the carbon dioxide gas mist-enclosing means into the outside, if necessary in parallel with the step (b), in order to maintain the pressure of gas within the carbon dioxide gas mist-enclosing means at or above a prescribed value being higher than the atmospheric pressure, and a step (d) of continuing such a step of supplying, for at least 20 minutes, the carbon dioxide mist into the carbon dioxide gas mist-enclosing means, thereby to prevent, improve or curing myocardial infarction of the living organism.

In place of the above step (d), it is also sufficient to measure concentration of the carbon dioxide gas mist in the carbon dioxide gas mist-enclosing means, and continue to supply carbon dioxide gas mist for at least 20 minutes in manner such that concentration of the carbon dioxide gas mist remains at or above prescribed value (as shown in (B) part of FIG. 1).

By the way, the step (e) controls the supplying amount of the carbon dioxide gas mist and continues this for at least 20 minutes or more, and preferably, continuation of 30 minutes or more is optimum for preventing, improving or curing myocardial infarction.

The carbon dioxide gas mist is characterized by containing a carbon dioxide gas mist of not more than 10 μm in diameter. Thereby, the carbon dioxide gas mist penetrates efficiently under the skin of the living organism through skin pores or the skin and mucous membrane of the living organism.

Air pressure in the carbon dioxide gas mist-enclosing means is characterized by being 1.01 to 2.5 air pressure. Body-pressure of the living organism is almost equivalent to air pressure (1 air pressure), and so in the present carbon dioxide gas mist pressure bath method, the carbon dioxide gas mist is controlled to contact the skin and mucous membrane of the living organism at pressure being higher than air pressure for more heightening permeability into a subcutaneous tissue.

In this carbon dioxide gas mist pressure bath method, the concentration of the carbon dioxide gas mist within the carbon dioxide gas mist-enclosing means is determined to be 60% or more.

Figure 36:
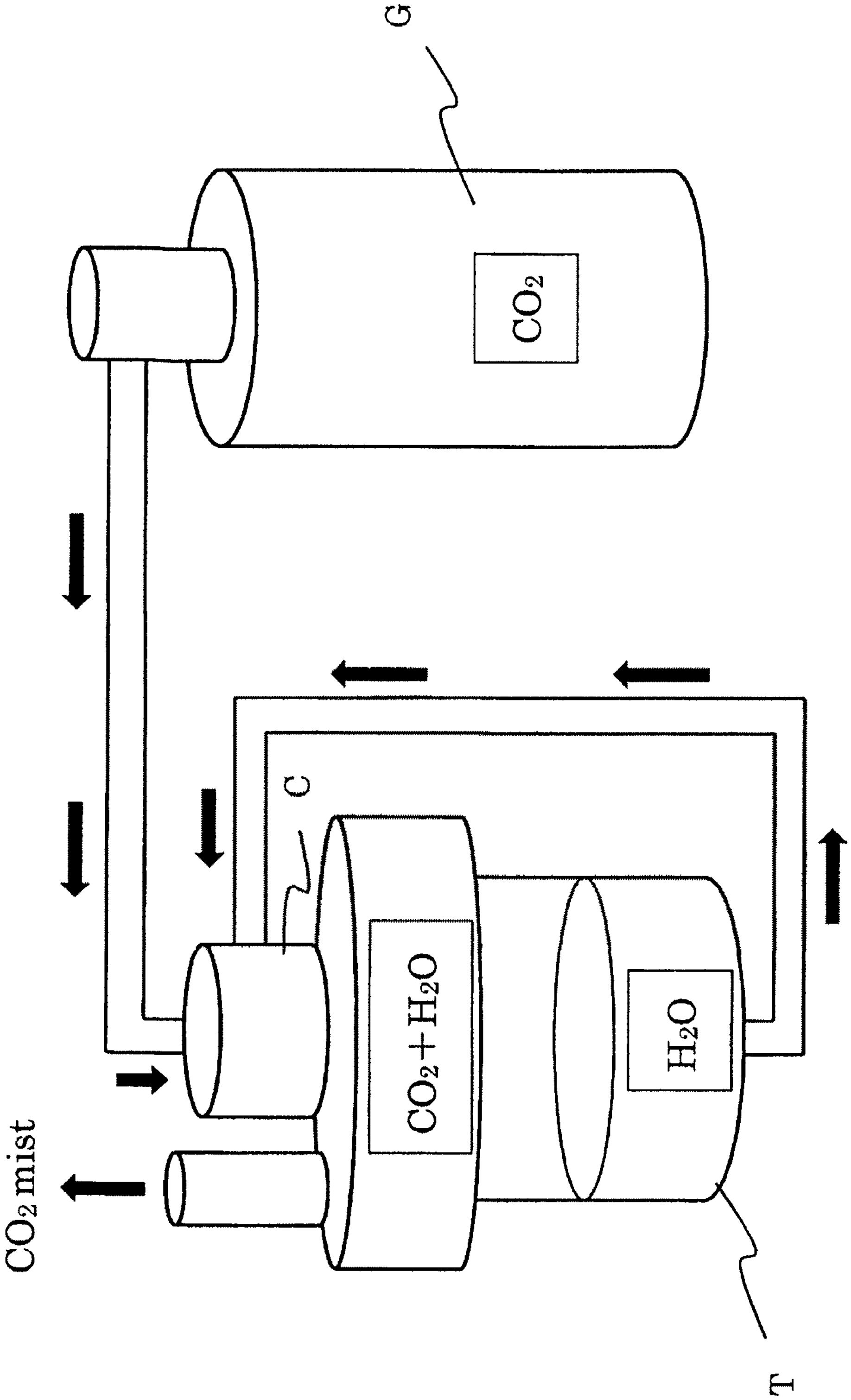
FIG. 36 A view explaining the principle structure of the means of generating the carbon dioxide gas mist.

A principle structure of a means generating the carbon dioxide gas mist is shown in FIG. 36. Water in a water tank T is injected from the inside of a carbon dioxide supply device G into a closed container C where carbon dioxide pressure is impressed to jet into an enclosed container C being under the carbon dioxide atmosphere, whereby carbon dioxide and water are pulverized and dissolved, so that the carbon dioxide gas mist is formed.

Figure 2:
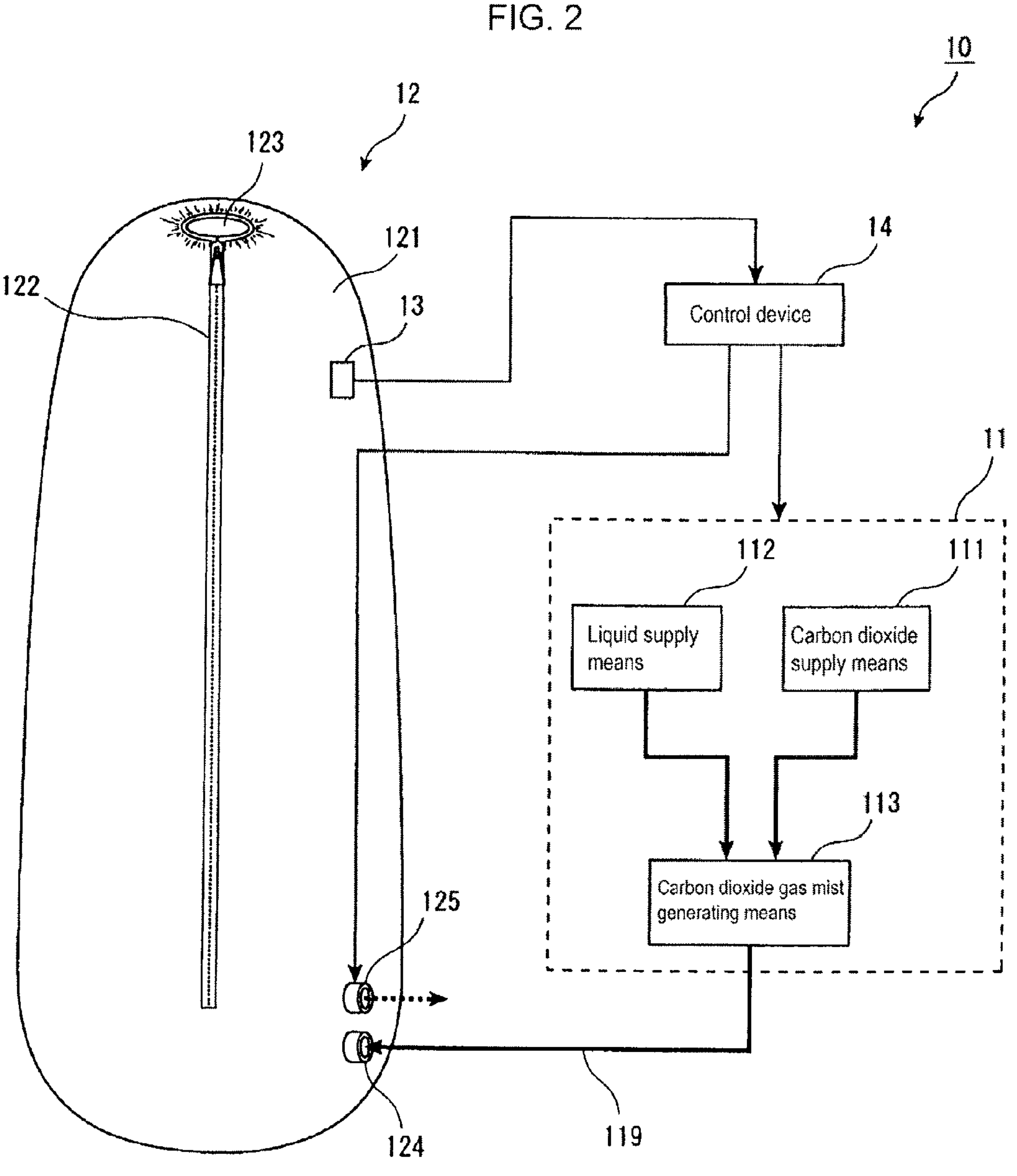
FIG. 2 A typical view showing the outline of a first embodiment of the carbon dioxide gas mist pressure bath apparatus of the invention for preventing, improving or curing myocardial infarction.

FIG. 2 is the typical view showing the outline of the first embodiment of the carbon dioxide gas mist pressure bath apparatus for preventing, improving or curing myocardial infarction of this invention. The carbon dioxide gas mist pressure bath apparatus 10 has, as shown in FIG. 2, the carbon dioxide gas mist generating and supplying means 11, the pressure bath cover 12 (a carbon dioxide gas mist encircling means) for encircling the carbon dioxide gas mist together with the living organism under the sealing condition, the concentration meter 13 (concentration detecting means) for measuring the concentration of the carbon dioxide gas mist within the pressure bath cover 12, and a control device 14 (control means) for controlling the supplying amount of the carbon dioxide gas mist from the carbon dioxide gas mist generating and supplying means 11 such that the concentration of the carbon dioxide gas mist becomes a predetermined value or more.

The carbon dioxide gas mist generating and supplying means 11 comprises a carbon dioxide supply means 111 for supplying carbon dioxide, a liquid supply means 112 for supplying a liquid, and a carbon dioxide gas mist generating means 113 for generating and supplying a gas mist (called as "carbon dioxide gas mist" hereafter) prepared by pulverizing and dissolving carbon dioxide from the carbon dioxide supply means 111 and the liquid from the liquid supply means 112.

The carbon dioxide supply means 111 is composed of, e.g., a gas bomb, and supplies carbon dioxide to the carbon dioxide gas mist generating means 113. This carbon dioxide supply means 111 is furnished, though omitting a drawing, with a regulator for adjusting gas pressure. There may be disposed a heater for heating gas and a thermometer for controlling temperature.

The liquid supply means 112 is composed of a pump or the like, and supplies the liquid to the carbon dioxide gas mist generating means 113. Otherwise, a supply means of gas mixing water such as, for example, an ozone water generating means is sufficient.

As the liquid to be supplied, it is preferable to employ water, ionic water, ozone water, physiological salt solution, purified water or sterilized and purified water. Further, these liquids are sufficient to contain medicines useful to users' diseases or symptom. As the medicines, for example, listed are anti-allergic agent, anti-inflammatory, anti-febrile agent, anti-fungus agent, anti-influenza virus agent, anti-influenza vaccine, steroid agent, anti-cancer agent, anti-hypertensive agent, cosmetic agent, or trichogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, anti-inflammatory agent, pain-killing, anesthetic, and immunity. Otherwise the liquids may be added with ethanol, gluconic acid chlorohexizine, amphoteric surface active agent, benzalkonium chloride, alkyldiamino ether glycin acetate, sodium hypochlorite, acetyl hydroperoxide, sodium sesqui-carbonate, silica, povidone-iodine, sodium hydrogen carbonate. In addition, high density carbonate spring, bactericide or cleaning agent may be added (as examples organic components, sulfate, carbonate, sodium dichloroisocyanurate).

By the way, though not showing, preferably, there may be disposed a heater for heating liquid and a thermometer for controlling temperature in the liquid supply means 112.

The carbon dioxide gas mist generating means 113 is such a device for generating the carbon dioxide gas mist prepared by pulverizing and dissolving gas supplied from the carbon dioxide supply means 111 and liquid supplied from the liquid supply means 112, and supplying it to a pressure bath cover 12. The diameter of the mist is optimum being not more than 10 μm. As the carbon dioxide gas mist generating means 113, for example, systems using a supersonic, an atomizing or fluid nozzles may be applied.

Figure 3:
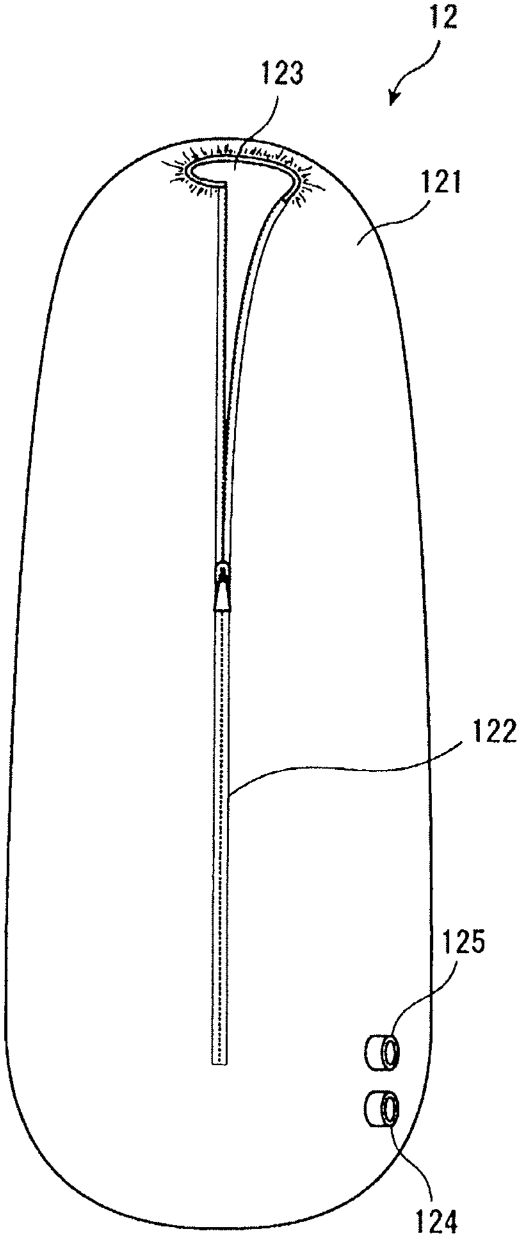
FIG. 3 A typical view showing the outline of the pressure bath cover of the carbon dioxide gas mist pressure bath apparatus shown in FIG. 2.
Figure 4:
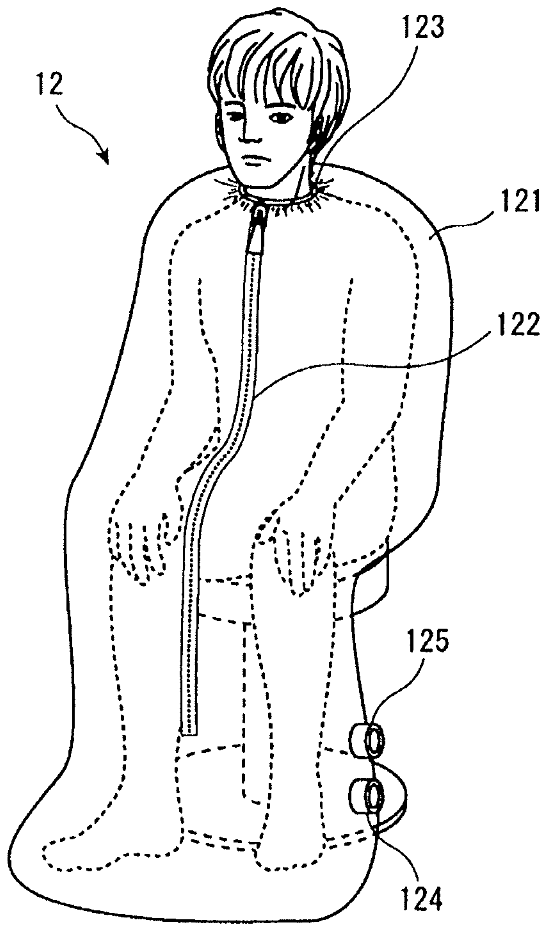
FIG. 4 A typical view showing a condition of applying the pressure bath cover of FIG. 3 to a human body.

Next, the pressure bath cover 12 is composed of a cover main body 121 which covers the skin and mucous membrane of the living organism (herein, as the example, the human body) and forms a space of sealing inside the carbon dioxide gas mist. FIG. 3 shows the outline of the pressure bath cover, and FIG. 4 shows the condition of applying the pressure bath cover 12 to the human body. As shown in these Figures, the cover main body 121 is preferably composed of a bag shaped member of a pressure resistant, non-air permeable and non-moisture permeable materials. In this case, the cover main body 121 should be formed with soft materials such that it is folded or a user can move freely inside as seating on a seat while wearing (refer to FIG. 4). Concrete raw materials are desirable in regard to, for example, a natural rubber, silicone rubber, polyethylene, poly-propylene, polyvinylidene chloride, poly-stylene, polyvinylacetate, polyvinyl chloride, polyamide resin, or polytetrafluoroethylene.

The bag shaped cover body in FIG. 4 covers the whole body, and since blood circulation in the myocardial region is improved or accelerated by the carbon dioxide gas mist pressure bath, it is enough to surround only the upper half of the living body under an enclosed condition. The cover shaped main body 121 is illustrated here, and as will be later mentioned concerning others, a box typed shape may be employed.

The cover main body 121 has an opening and closing part 122 for getting in and out the living body, and also has an open part 123 for exposing the head of the living body outside of the cover 12. Further, this cover main body 121 has an inlet port 124 for getting in the carbon dioxide gas mist inside and an outlet port 125 (exhaust means) for getting out the inside carbon dioxide gas mist. There may be provided a safety valve (by-pass valve) of automatically opening a valve when the inside of the pressure bath cover 12 goes above a predetermined pressure.

An opening and closing part 122 is preferably composed of a linear fastener (zipper) processed with a pressure resistant, non-air permeable and non-moisture permeable materials. Others as a face fastener is also sufficient.

An open part 123 is provided for exposing the head of the living body outside of the cover 12, and its periphery fits the open part 123 to the user around his neck for avoiding the carbon dioxide gas mist to leak from its clearance. The leakage avoiding means may use others such as a string, belt or face fastener.

An inlet port 124 communicates with the cover main body 121 for introducing the carbon dioxide gas mist into the pressure bath cover 12, and a carbon dioxide gas mist supply pipe 119 passes thereto for connecting the carbon dioxide gas mist generating means 113. The inlet port 124 has inside a check valve for avoiding back-flow of the carbon dioxide gas mist.

An outlet port 125 is an air hole for controlling internal pressure or concentration of the carbon dioxide gas mist by exhausting air within the pressure bath cover 12.

A concentration meter 13 is installed within the pressure bath cover 12, measures the concentration of the carbon dioxide gas mist, and outputs measuring values to a control device 14.

On the other hand, the control device 14 is composed of a computer having CPU, memory and display, keeps the concentration of the carbon dioxide gas mist within the pressure bath cover 12 to be a predetermined value or higher (preferably 60% or higher), and further for keeping, controls the carbon dioxide gas mist generating and supplying means 11 and the outlet port 125 of the pressure bath cover 12 on the basis of the measuring values of the concentration meter 13. As to others, the control device 14 may control temperatures or pressure values in the pressure bath cover 12, and further, it has a timer function and enables the carbon dioxide gas mist pressure bath at a set time.

Figure 5:
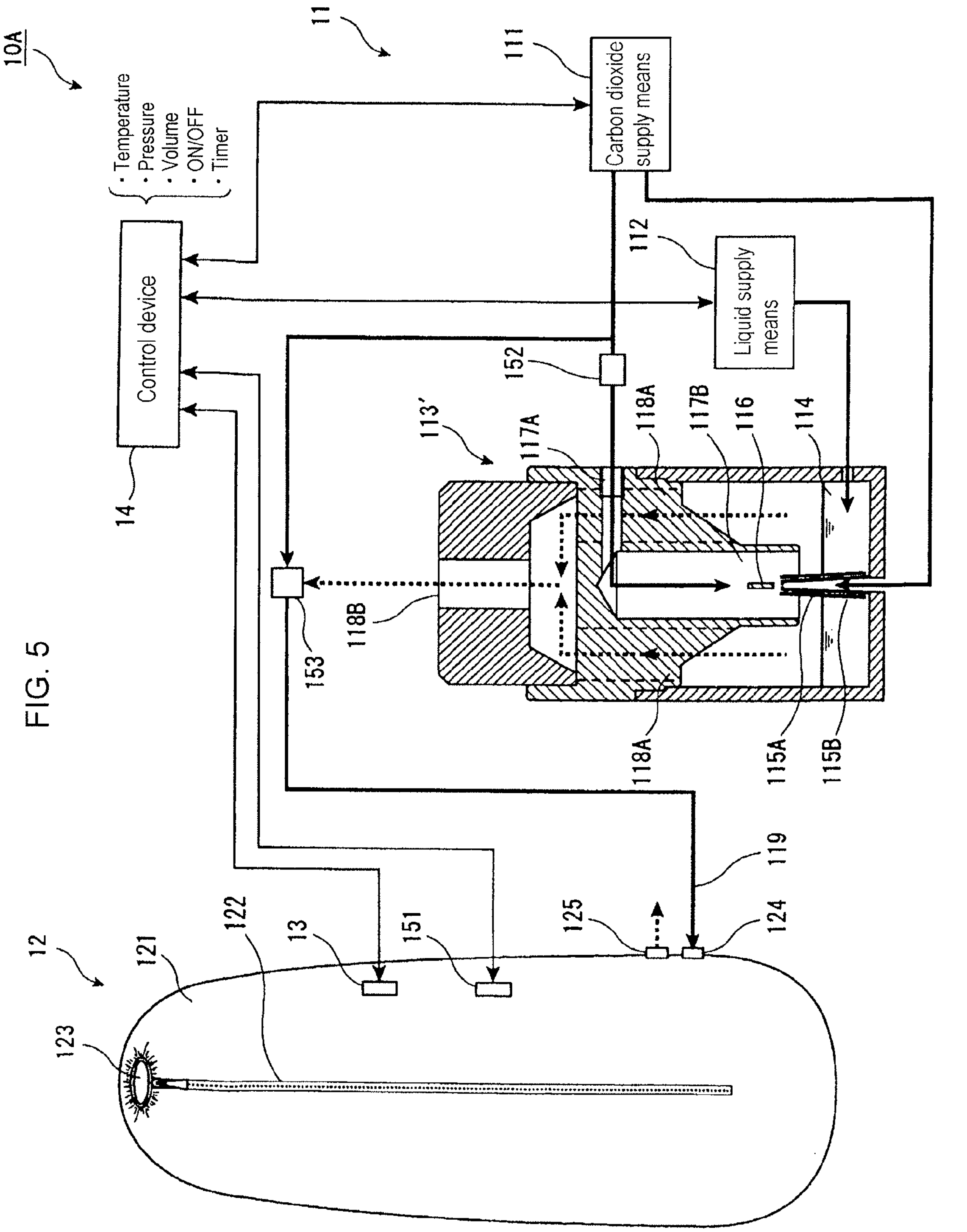
FIG. 5 A typical view showing the carbon dioxide gas mist pressure bath apparatus (First Embodiment) employing the carbon dioxide gas mist generating means of an atomizing system.

One example of the present carbon dioxide gas mist pressure bath apparatus will be concretely explained as follows. FIG. 5 is the typical view showing the carbon dioxide gas mist pressure bath apparatus 10A (First Embodiment) employing the carbon dioxide gas mist generating means of the atomizing system. Herein, a carbon dioxide gas mist generating means of the atomizing system 113' is used as an example of the carbon dioxide gas mist generating means 113.

The carbon dioxide gas mist generating means 113' is formed with a liquid storage 114 for storing a liquid from the liquid supply means 112, a nozzle 115A for discharging, from its front opening, carbon dioxide supplied from the carbon dioxide supply means 111, a liquid suction pipe 115B for sucking liquid stored in the liquid storage 114 up to its front end, and a baffle 116 positioned in opposition to the front end openings of the nozzle 115A and the liquid suction pipe 115B. Further, this apparatus 10A is furnished with a carbon dioxide supply part 117A, a carbon dioxide inlet part 117B, a carbon dioxide gas mist collection part 118A and a carbon dioxide gas mist outlet part 118B, these carbon dioxide supply part 117A and the carbon dioxide inlet part 117B supplying carbon dioxide from the carbon dioxide supply means 111 into the carbon dioxide gas mist generating means 113', the carbon dioxide supply part 117A and the carbon dioxide inlet part 117B introducing carbon dioxide around the nozzle 115A and making air flow for exhausting the carbon dioxide gas mist, and the carbon dioxide gas mist collection part 118A and the carbon dioxide gas mist outlet part 118B collecting the carbon dioxide gas mist and exhausting the carbon dioxide gas mist. The carbon dioxide gas mist discharged from the carbon dioxide gas mist outlet part 118B is supplied into the pressure bath cover 12 through a carbon dioxide gas mist supply pipe 119.

By the way, this carbon dioxide gas mist pressure bath apparatus 10A is also installed with a manometer 151 other than a concentration meter 13 within the pressure bath cover 12. The control device 14 performs controls based on their measuring values. For example, air pressure within the pressure bath cover 12 is controlled to be not lower than 1 (more preferably, 1.2 to 2.5 air pressure). Further, in case air pressure within the pressure bath cover 12 exceeds a predetermined value, it is sufficient to stop the carbon dioxide gas mist generating and supplying means 11 and to control to discharge from an outlet.

Further, in this carbon dioxide gas mist pressure bath apparatus 10A, between the carbon dioxide supply means 111 and the carbon dioxide supply part 117A of the carbon dioxide gas mist generating means 113', a flow valve 141 is provided to enable adjustment of the gas flowing amount to the carbon dioxide gas mist generating means 113' and at the same time, a switch valve 142 is provided in the carbon dioxide gas mist supply pipe 119 for switching the carbon dioxide gas mist from the carbon dioxide gas mist outlet part 118B of the carbon dioxide gas mist generating means 113' with carbon dioxide from the carbon dioxide supply means 111, so that the carbon dioxide gas mist concentration within the pressure bath cover 12 can be adjusted.

Next explanation will be made to a sequence of performing the carbon dioxide gas mist pressure bath using the present carbon dioxide gas mist pressure bath apparatus 10A. The user opens at first an opening and closing part 122, gets himself into the cover main body 121, suitably meets an open part 123 to his neck, closes the opening and closing part 122, and makes a sealed condition.

Then, the liquid is poured from a liquid supply means 112 into the liquid storage 114 of the carbon dioxide gas mist generating means 113', and subsequently carbon dioxide is supplied from the carbon dioxide supply means 111 into the carbon dioxide gas mist generating means 113'.

When carbon dioxide is supplied to the nozzle 115A, since the nozzle 115A is reduced in diameter toward the front end as seeing in FIG. 5, carbon dioxide heightens flowing rate and gets out. Liquid is sucked up within a liquid suction pipe 115B owing to negative pressure generated by air flow at this time, blown up by carbon dioxide at the front end (nozzle front end), collided with the baffle 116, and turns out a mist. Carbon dioxide is also further supplied from the carbon dioxide supply part 117A and the carbon dioxide inlet part 117B into the carbon dioxide gas mist generating means 113', and heightens exhausting pressure of the carbon dioxide gas mist. The generated carbon dioxide gas mist passes through the carbon dioxide gas mist collecting part 118A and the carbon dioxide gas mist outlet part 118B, and comes to the pressure bath cover 12 from the carbon dioxide gas mist supply pipe 119. The control device 14 is based on the values of the concentration meter 13 and the manometer 151, and controls the carbon dioxide gas mist generating and supplying means 11 and the outlet port 125 of the pressure bath cover 12, and carries out the carbon dioxide gas mist pressure bath until a predetermined time of a timer passes.

Preferably, the carbon dioxide gas mist supply pipe 119 is composed wholly or partially with a soft and cornice shaped pipe of large diameter. Since the cornice shaped pipe is freely bent or expanded, the user's action is not limited. Further, if the cornice shaped pipe is formed inside with a groove in an axial direction and in case the gas mist flows in the gas mist is liquidized, liquid drops can be gathered for easily recovering.

The above mentioned has shown an example of supplying the carbon dioxide gas mist into the pressure bath cover 12 through one inlet port 124 from one carbon dioxide gas mist generating and supplying means 11, and instead of this example, it is sufficient to supply the carbon dioxide gas mist via a plurality of inlet ports from a plurality of carbon dioxide gas mist generating and supplying means. In addition, the above example has explained as to the human body as a living body to be applied with the present carbon dioxide gas mist pressure bath device 10, but not limiting to the human body, other animals (for example, racing horses, pets and others) may be applied with.

Figure 6:
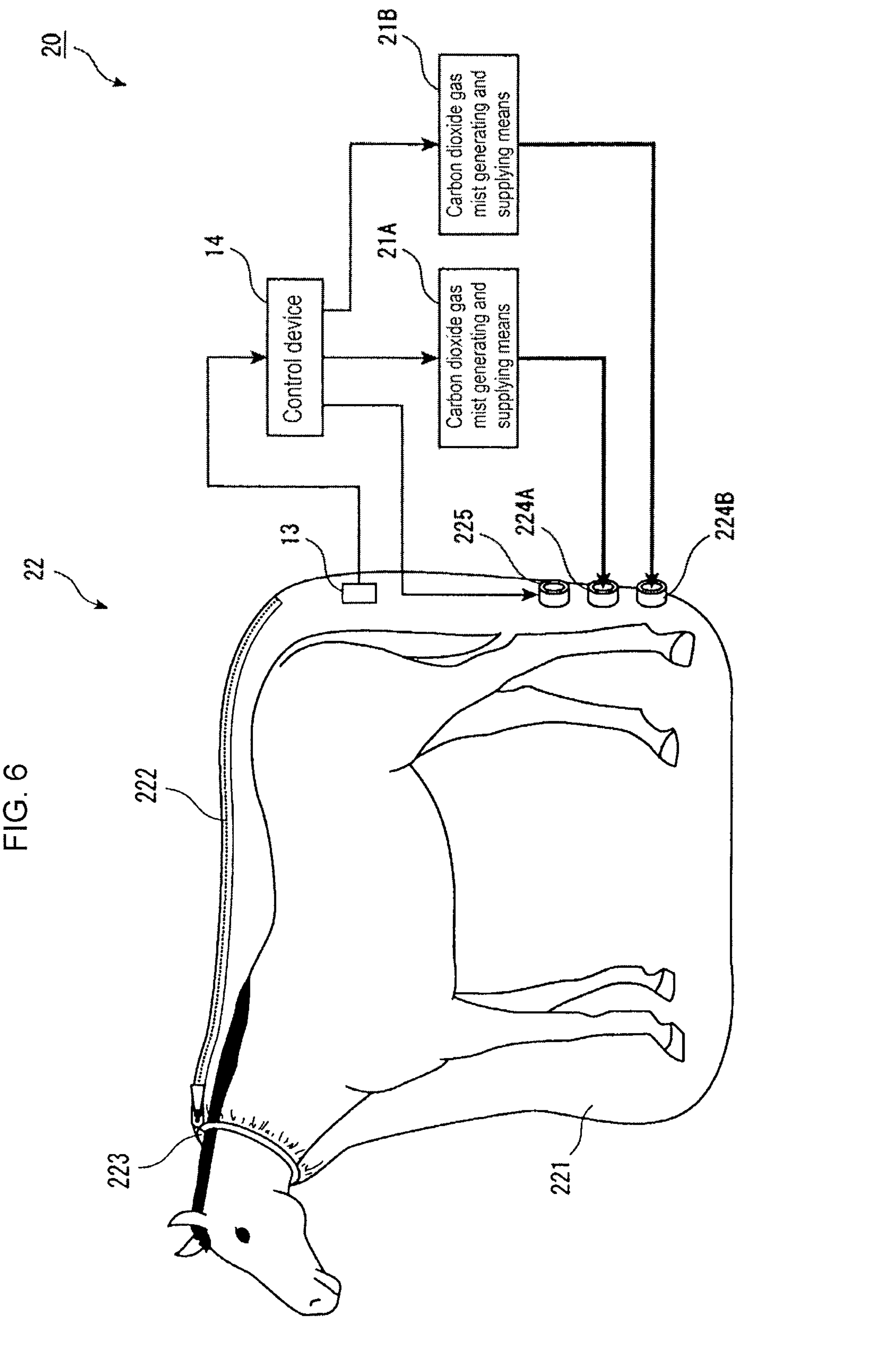
FIG. 6 A typical view showing the carbon dioxide gas mist pressure bath apparatus employing a plurality of the carbon dioxide gas mist generating and supplying means shown in FIG. 2, applied, for example, to a horse.

FIG. 6 is the typical view showing the condition that the carbon dioxide gas mist pressure bath apparatus employing a plurality of the carbon dioxide gas mist generating and supplying means is applied, for example, to a horse. As to the same parts of FIG. 2, the same numerals and signs will be given to omit detailed explanations.

As shown in FIG. 6, the carbon dioxide gas mist pressure bath 20 has the plurality (herein, two, as an example) of carbon dioxide gas mist generating and supplying means 21A, 21B. A horse pressure bath cover 22 is formed in that a cover main body 221 has a size covering almost all of the whole body of the horse, having an opening and closing part 222 and an opening part 223 with the plurality (herein, two, as an example) of inlet ports 224A, 224B and an outlet port 225.

The inlet ports 224A, 224B are connected to the carbon dioxide gas mist generating and supplying means 21A, 21B, respectively. Herein, it is allowed that each of carbon dioxide gas mist generating and supplying means 21A, 21B generates the carbon dioxide gas mist from different liquids for giving actions of the respective liquids to the living body.

Figure 7:
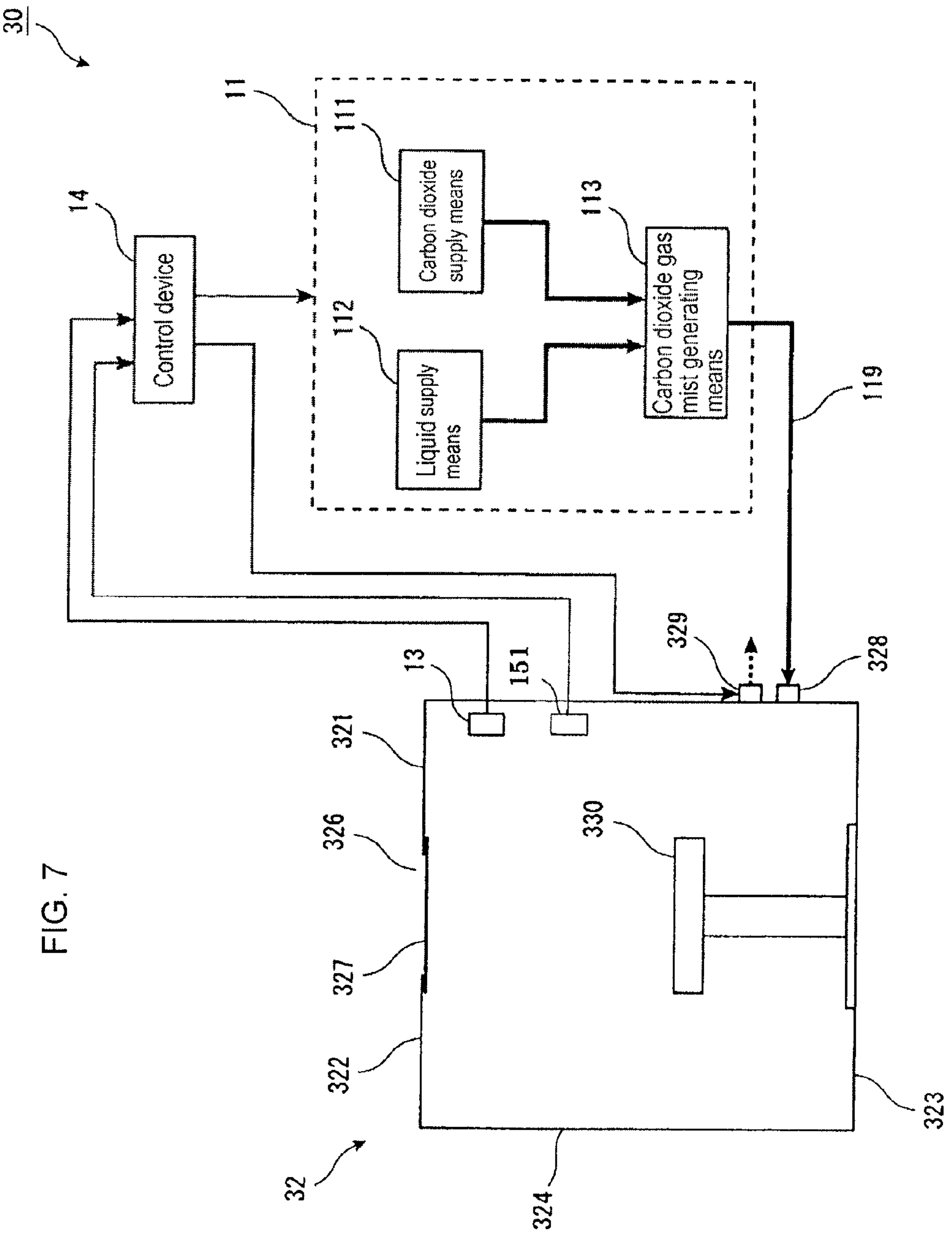
FIG. 7 A typical view showing the outline of Second Embodiment of the carbon dioxide gas mist pressure bath apparatus of the invention for preventing, improving or curing myocardial infarction.
Figure 8:
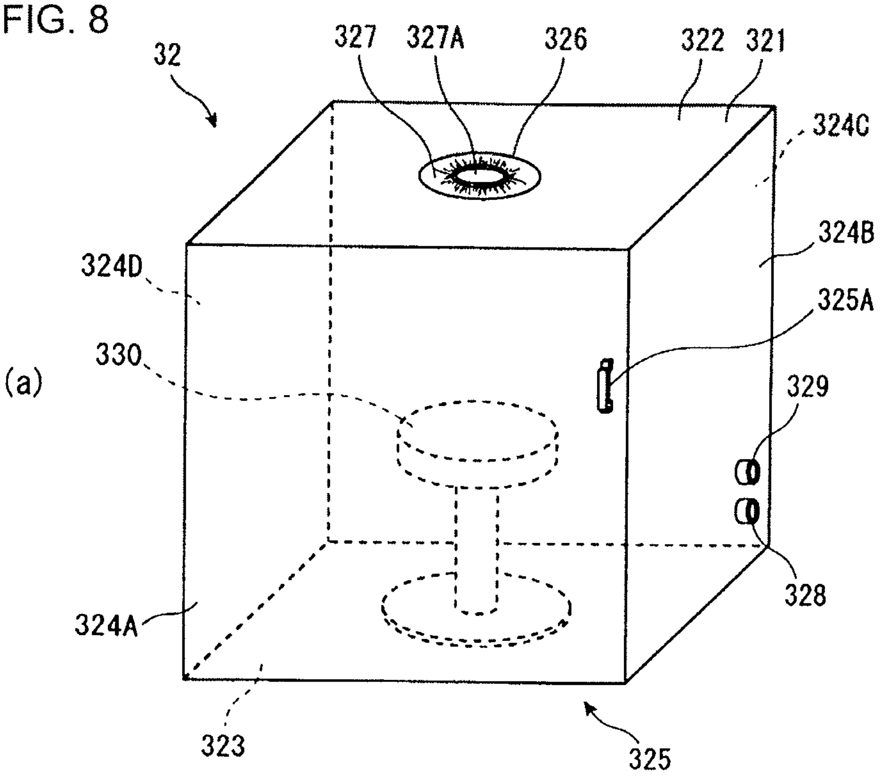
FIG. 8 Typical views showing the outlines of the pressure bath cover of the carbon dioxide gas mist pressure bath apparatus shown in FIG. 7.
Figure 8:
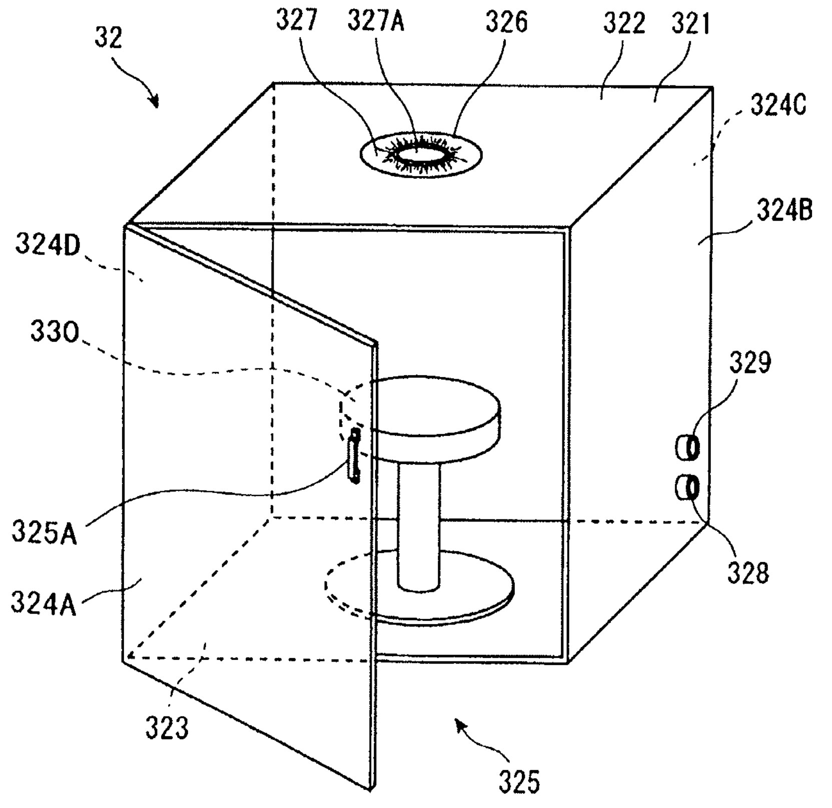
Figure 9:
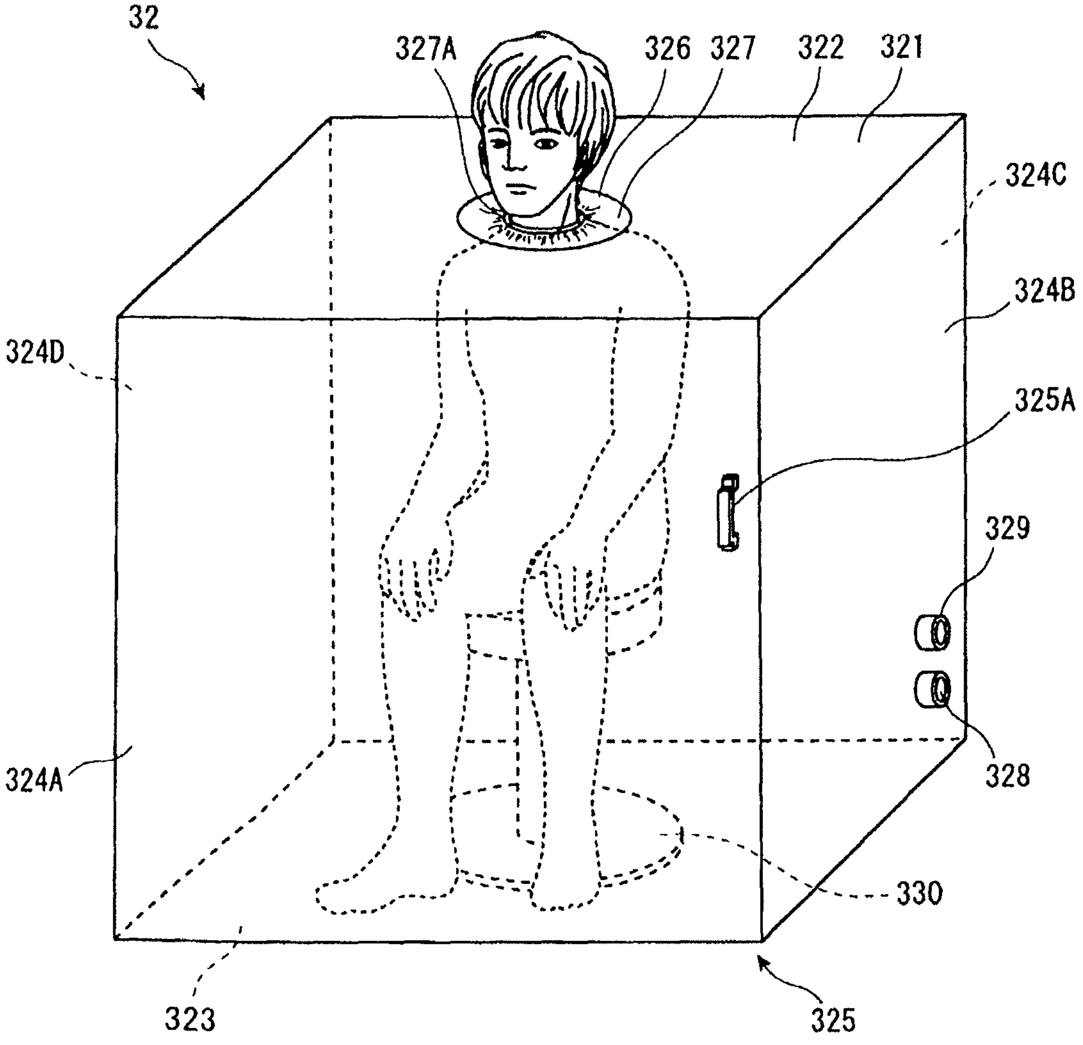
FIG. 9 A typical view showing a condition of applying the pressure bath cover of FIG. 8 to the human body.

The above mentioned has explained the pressure bath cover 12 composed of the bag shaped cover main body 121, and the pressure bath cover 12 is not limited thereto but applicable to various shapes. FIG. 7 is the typical view showing the outline of the carbon dioxide gas mist pressure bath apparatus (the second embodiment) having the pressure bath cover of a box type enabling to be stationary. As to the same parts of FIG. 2, the same numerals and signs will be given to omit detailed explanations. FIG. 8 shows the outline of the pressure bath cover of the box type depending on the present embodiment. FIG. 9 shows the condition of applying this type to the human body.

As shown in FIG. 7, the carbon dioxide gas mist pressure bath apparatus 30 has the carbon dioxide gas mist generating and supplying means 11 of generating and supplying the carbon dioxide gas mist, the pressure bath cover 32 for enclosing the carbon dioxide gas mist gas mist together with the living body under the sealing condition (the carbon dioxide gas mist enclosing means), the concentration meter 13 (the concentration detecting means) of measuring the concentration of the carbon dioxide gas mist within the pressure bath cover 32, and the control device 14 (the control means) of controlling the supplying amount of the carbon dioxide gas mist from the carbon dioxide gas mist generating and supplying means 11. Further, the manometer 151 is provided, and when air pressure within the pressure bath cover 32 becomes higher than the predetermined value, the manometer 151 stops the carbon dioxide gas mist generating and supplying means 11, and also controls exhausting of the carbon dioxide gas mist within the pressure bath cover 32 from the outlet port. There may be provided a safety valve (by-pass valve) of automatically opening a valve when the inside of the pressure bath cover 32 goes above a predetermined pressure.

The pressure bath cover 32 is composed of a box typed cover main body 321 being sized to enable to cover almost the whole of the living body. That is, it is formed with an upper part 322, bottom part 323, plural (herein, four) side parts 324 (324A, 324B, 324C and 324D). Among of them, one side (herein, as an example, 324A) is an opening and closing gate 325 as seeing in FIG. 8(*b*) as the user goes into and out from the pressure bath cover 32. This gate 325 has outside a handle 325A. Omitting illustration, the handle is desirably furnished inside so that the gate 325 can be opened and closed in the inside.

At the upper part 322 of the cover main body 321, an opening 326 is formed for exposing the user's head outside of the cover 32, having a size for freely getting in and out the head. Further, around a periphery of the opening 326, a leakage prevention means 327 is provided for avoiding leakage of the carbon dioxide gas mist from a clearance. Herein, inside of the opening 326, a non-air permeable material (for example, polyethylene seat) having an opening 327A is furnished, and the edge of this opening 327A is attached with a member such as a rubber having an expansion, and the user is fitted at his neck. Instead of the rubber, a string, belt or face fastener are sufficient.

A pressure bath cover 32 is connected to the carbon dioxide gas mist supply pipe 119 and has an inlet port 328 for introducing the carbon dioxide gas mist into the inside. This inlet port 328 is equipped inside with a check valve for avoiding back-flow of the carbon dioxide gas mist. Further, the pressure bath cover 32 has an outlet port 329 for adjusting inside pressure or concentration of the carbon dioxide gas mist by issuing gas in the pressure bath cover 12. The outlet port 329 opens and closes based on an order of the control device 14.

Incidentally herein, a chair 330 is placed within the pressure bath cover 32 for the user to carry out the carbon dioxide gas mist pressure bath as seating on it. For this chair 330, preferably it may change a seating height meeting the user's sitting height.

For taking the carbon dioxide gas mist pressure bath, using the pressure bath cover 32 of the present embodiment, the user at first opens the gate 325 of the cover 32, enters into the cover main body 321, and adjusts the height of the chair 330 so that the head is in position as to the opening 326. Next, the seats on the chair 330 and passes the head through an opening 326, sets a leakage prevention means 327 around the neck to prevent leakage of the carbon dioxide gas mist. Then, the gate 325 is closed to make the inside of the cover 32 almost sealing. Under this condition, the carbon dioxide gas mist is supplied from the carbon dioxide gas mist generating and supplying means 11 to carry out the carbon dioxide gas mist pressure bath.

Figure 10:
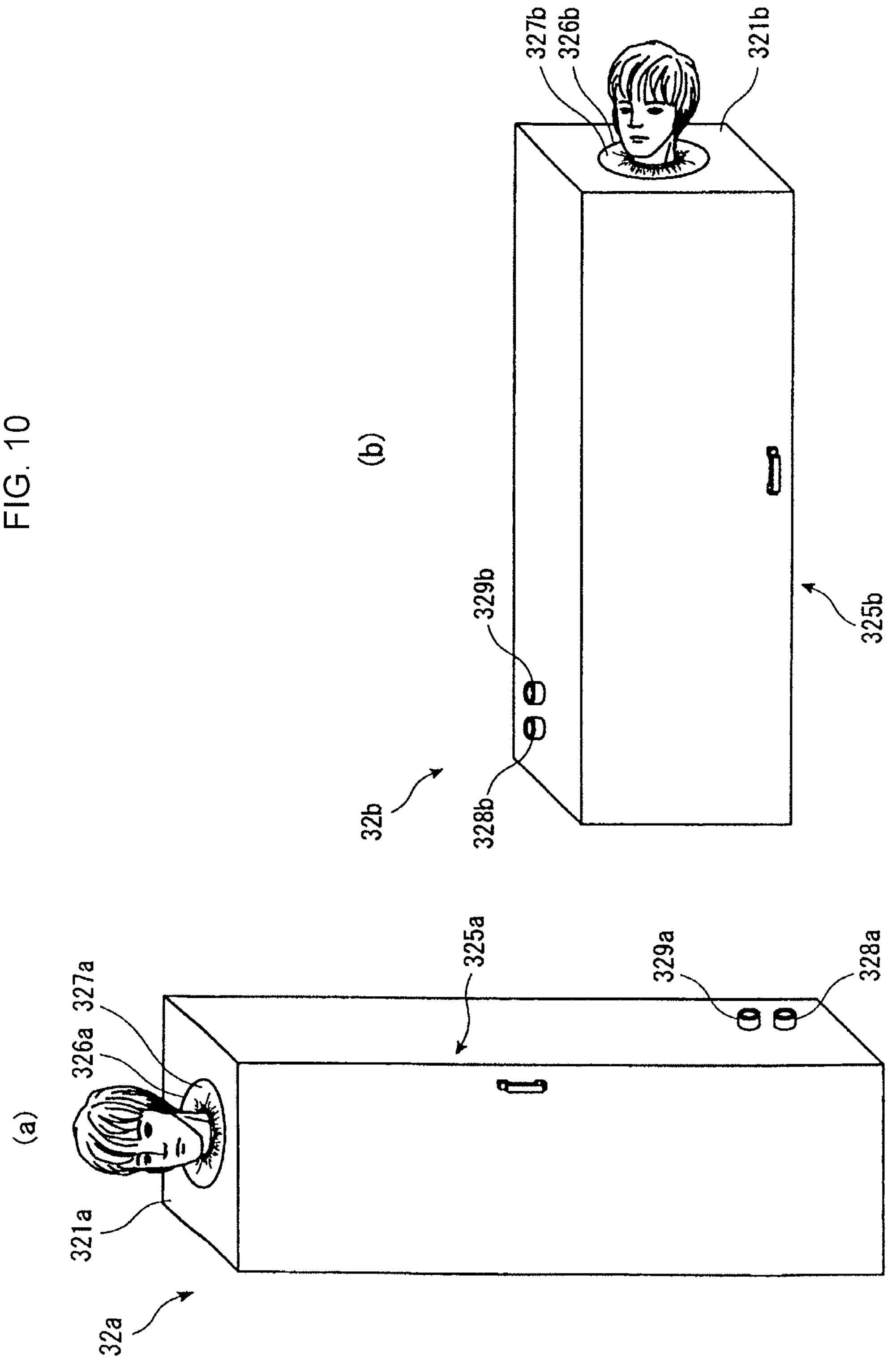
FIG. 10 Typical views showing other formed examples of the pressure bath covers of the carbon dioxide gas mist pressure bath apparatus shown in FIG. 7.

Up to here, the example has been shown that the chair 330 is prepared in the pressure bath cover 32 and the user takes the carbon dioxide gas mist pressure bath as seating, and the pressure bath cover 32 may be changed into such a shape for other postures. FIG. 10 shows the pressure bath covers 32 for taking the carbon dioxide gas mist pressure baths by other postures.

FIG. 10(*a*) shows a pressure bath cover 32*a* for a standing posture. As is seen, the pressure bath cover 32*a* for the standing posture is formed as vertically formed shape. The cover main body 321*a* is provided with an opening 326*a* and a leakage prevention means 327*a*. Further, there are provided an inlet port 328*a* of the carbon dioxide gas mist, an outlet port 329*a* and a gate 325*a* for going and out.

FIG. 10(*b*) shows a pressure bath cover 32*b* for a lying posture. As is seen, the pressure bath cover 32*b* for the lying posture is formed as horizontally formed shape. The cover main body 321*b* is provided with an opening 326*b* and a leakage prevention means 327*b*. Further, there are provided an inlet port 328*b* of the carbon dioxide gas mist, an outlet port 329*b* and a gate 325*b* for going and out.

By the way, similarly to the above mentioned first embodiment, the living body to be applied with the pressure bath cover 32 is not limited to the human body, but other animals (for example, racing horses, pets and others) may be applied with.

Figure 37:
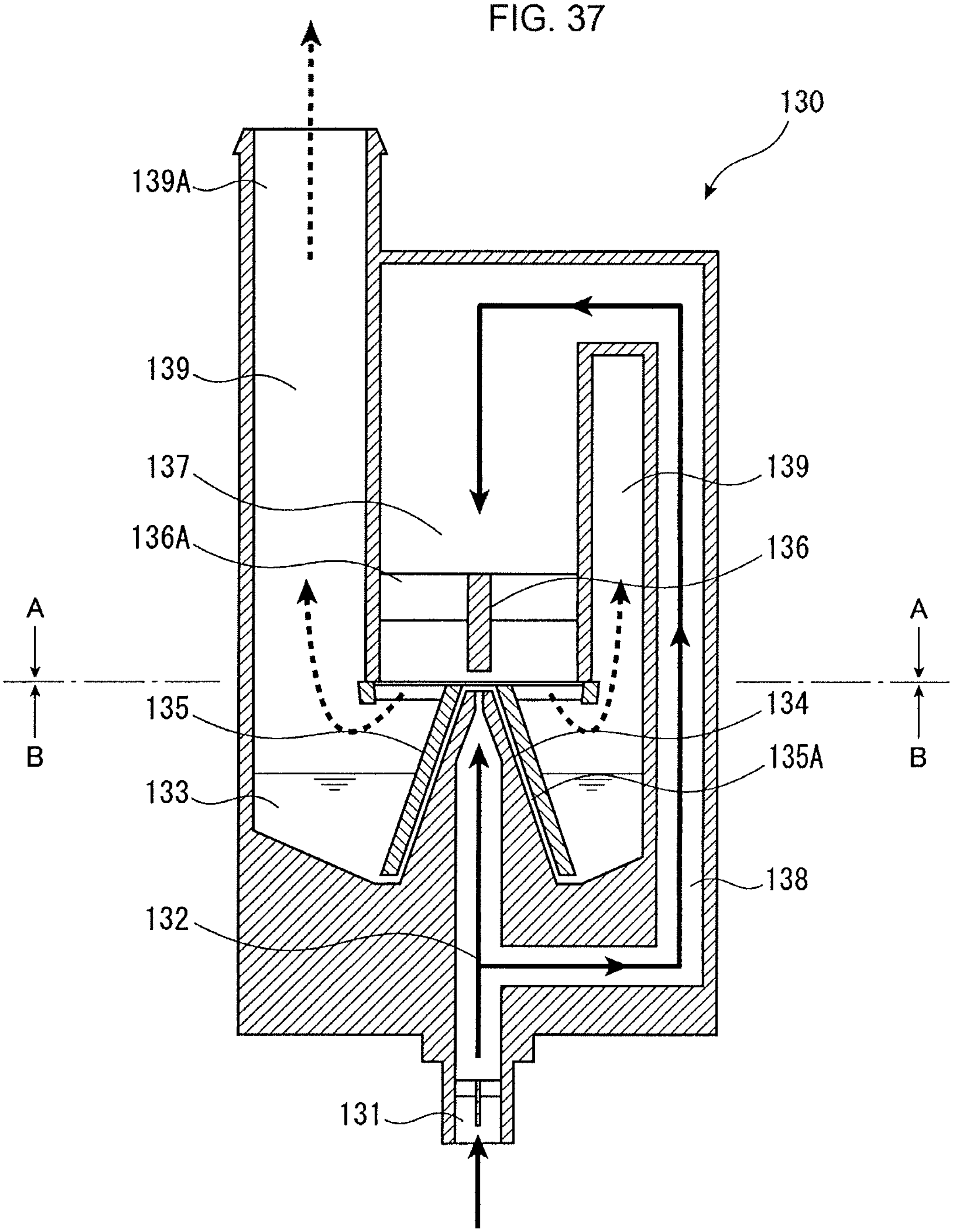
FIG. 37 A cross sectional and typical view showing the structure of another composing example of the carbon dioxide gas mist generating means.

FIG. 5 has shown the carbon dioxide generating means 113' as the concretely structured example of the carbon dioxide gas mist generating means 113 of FIG. 2, and further, while referring to FIG. 37, explanation will be made to a carbon dioxide generating means 130 of another structured example. FIG. 37 is the cross sectional and typical view showing the structure of the carbon dioxide generating means 130, and this carbon dioxide generating means 130 previously stores liquid inside, generates the gas mist prepared by pulverizing and dissolving liquid and gas by high speed flowing of gas supplied from the carbon dioxide supply means 111, further mixes gas, and supplies it to the pressure bath cover 12 shown in FIG. 2.

As shown in FIG. 37, the carbon dioxide gas mist generating means 130 is furnished with a connection part 131 connected with the gas supply means 111, a branch 132 of diverging gas flow from the connection part 131, a liquid storage 133 of storing liquid, a nozzle 134 of discharging one sided gas flow diverged at the branch 132, a liquid sending pipe 135A of sending liquid to the front end of the nozzle 134, a baffle 136 (a collision member) of colliding liquid blown up by gas flow jetted by the nozzle 134 and generating the gas mist, a confluent part 137 of making gas from an upward confluent with the gas mist, a gas introduction part 138 of guiding the other side gas flow diverged at the branch till the confluent part 137, and a gas mist discharging part 139 of collecting the gas mist to discharge, and these members are integrally formed as one body.

The connection part 131 is connected with the gas supply means 111 directly or via a gas code. The structure of the connection part 131 enables to connect a gas code communicating with the gas supply means 111, or directly connect the gas supply means 111, and depending on the gas supply means 111 to be connected, various forms may be applied.

The gas supplied from the gas 111 via the connection part 131 is branched into two at a branch. One of them directs to the nozzle 134 while the other goes to the gas introduction part 138. The gas directing to the nozzle 134 is exhausted from the nozzle front end 134A while the going to the gas introduction part 138 is guided until the confluent part 137.

The liquid storage 114 of the carbon dioxide gas mist generating means 113' shown in FIG. 5 has a structure of directly receiving the liquid from the liquid supply means 112, but in the carbon dioxide gas mist generating means 130 of FIG. 37, a predetermined liquid is previously stored at a manufacturing step and sealed. When using, it is opened to take the gas mist pressure bath. But the stored liquid is the same as that of the liquid storage 114 of the carbon dioxide gas mist generating means 113', and as above stated, water, ionic water, ozone water, physiological salt solution, purified water or sterilized and purified water are employed, and further it is also sufficient to contain medicines useful to users' diseases or symptom into these liquids.

At the central part of the liquid storage 133, a nozzle 134 is positioned. This nozzle 134 rises from the bottom of the liquid storage 133 and is formed almost conically toward the baffle 136. The nozzle 134 connects at its basic end to one of diverges 132 so that the gas can be exhausted from the nozzle front end 134A.

The liquid suction pipe 135A is formed between the outer circumference of the nozzle 134 and the inner circumference of the liquid suction pipe forming member 135 of the almost circular cone being larger by one turn than the nozzle 134. That is, as shown in FIG. 37, by positioning as covering the liquid suction pipe forming member 135 over the nozzle 134, the liquid suction pipe 135A is defined between the outer circumference of the nozzle 134 and the inner circumference of the liquid suction pipe forming member 135. Since a nail shaped projection (not showing) is provided at a base end (the lower portion of the almost circular cone) of the liquid suction pipe forming member 135, a space is formed at a base of the liquid suction pipe forming member 135 and the bottom of the liquid storage 133, so that the liquid stored in the liquid storage 133 is sucked up from this space by the liquid suction pipe 135A. In addition, the front end 135A of the liquid suction pipe forming member 135 opens nearly the front end open 135B of the nozzle 134, and the liquid sucked up by the liquid suction pipe 135A collides against the gas flow discharged from the nozzle 134.

The liquid sucked up by the liquid suction pipe 135A collides against the gas flow discharged from the nozzle 134 and is blown up, and collides against the baffle 136 disposed in opposition to the front end open 134A of the nozzle 134 and is pulverized so that the gas mist is generated. Herein, the baffle 136 is secured to the inside wall of the confluent part 137, but may be secured to the liquid suction pipe forming member 135.

On the other hand, the gas which is branched at the diverge 132 into a gas introducing part 138 goes along the gas introducing part 138 and reaches the confluent part 137. The gas introducing part 138 is a guide passage of the gas which directs upward the upper part passing through the inside side of the carbon dioxide gas mist generating means 130 from the diverge 132 provided at the lower part of the carbon dioxide gas mist generating means 130, and the gas introducing part 138 is formed integrally with the carbon dioxide gas mist generating means 130. Further, the confluent part 137 is composed of a cylindrical member disposed as encircling the baffle 136 above the front end open 134A of the nozzle 134, and communicates with the gas introducing part 138. Accordingly, the gas branched at the diverge 132 and guided into the gas introducing part 138 merges upward with the gas mist generated in the confluent part 137, and extrudes the gas mist toward a gas mist exhaust part 139.

The gas supplied from the gas introducing part 138 to the confluent part 137 can adjust supply pressure depending on sizes of diameters of a gas introducing part 138. By adjusting gas supply pressure, it is also possible to adjust the gas mist supply amount of the carbon dioxide gas mist generating means 130. In addition, it is possible to adjust the gas mist concentration (the mist concentration in the gas) and sizes of the mist by the gas introducing part 138.

The gas mist exhaust part 139 is a space defined in a periphery of the cylindrically shaped confluent part 137, collects the gas mist driven from the confluent part 137 by the gas from the gas introducing part 138, and exhausts it together with the gas. The gas mist driven by the gas mist exhaust part 139 is exhausted into the pressure bath cover 12 from a gas mist exhaust part 139A which is an exit positioned at the upper part of the carbon dioxide gas mist generating means 130. Between the gas mist exhaust part 139A and the pressure bath cover 12, the carbon dioxide gas mist supply pipe 119 connects.

The carbon dioxide gas mist generating means 130 may have such a structure where a part including the liquid storage 133 is made removable and replaceable with another new liquid storage 133. That is, the carbon dioxide gas mist generating means 130 is made fabricated, and by fabricating a replacing part including the liquid storage 133 with another part, the carbon dioxide gas mist generating means 130 becoming one body of the gas introducing part 138 is accomplished. Thus, by making the liquid storage 133 replaceable, the liquid storage 133 is made disposable, keeping hygienic. Further, by making the liquid storage 133 replaceable, the structure of supplying the liquid into the liquid suction pipe 135A is omitted. Preferably, the carbon dioxide gas mist generating means 130 has been sterilized during the producing stage.

In the above mentioned carbon dioxide gas mist generating means 130, the gas mist is generated as under. When the gas is supplied from the gas supply means 111 and since the nozzle 134 is reduced in diameter toward the front end, gas increases the flowing speed and is exhausted. The liquid in the liquid storage 133 is sucked up within the liquid suction pipe 135A owing to negative pressure caused by air flow at this time, is blown up by gas at the front end portion 135B of the liquid suction pump 135A, and collides against the baffle 136, so that the mist is generated. Desirably, the diameter of the mist generated by this collision is fine, and concretely, best is not larger than 10 μm. The thus finely pulverized mist can display effects of minus ion.

Gas passes through the branch 132 and is guided into the confluent part 137 from the gas introducing part 138, and it heightens exhausting pressure of the generated gas mist. The generated mist is mixed with gas from the branch 132 and discharged from the gas mist exhaust part 139. That is, explaining with FIG. 5, the gas mist is supplied into the pressure bath cover 12 via the carbon dioxide gas mist supply pipe 119.

Figure 38:
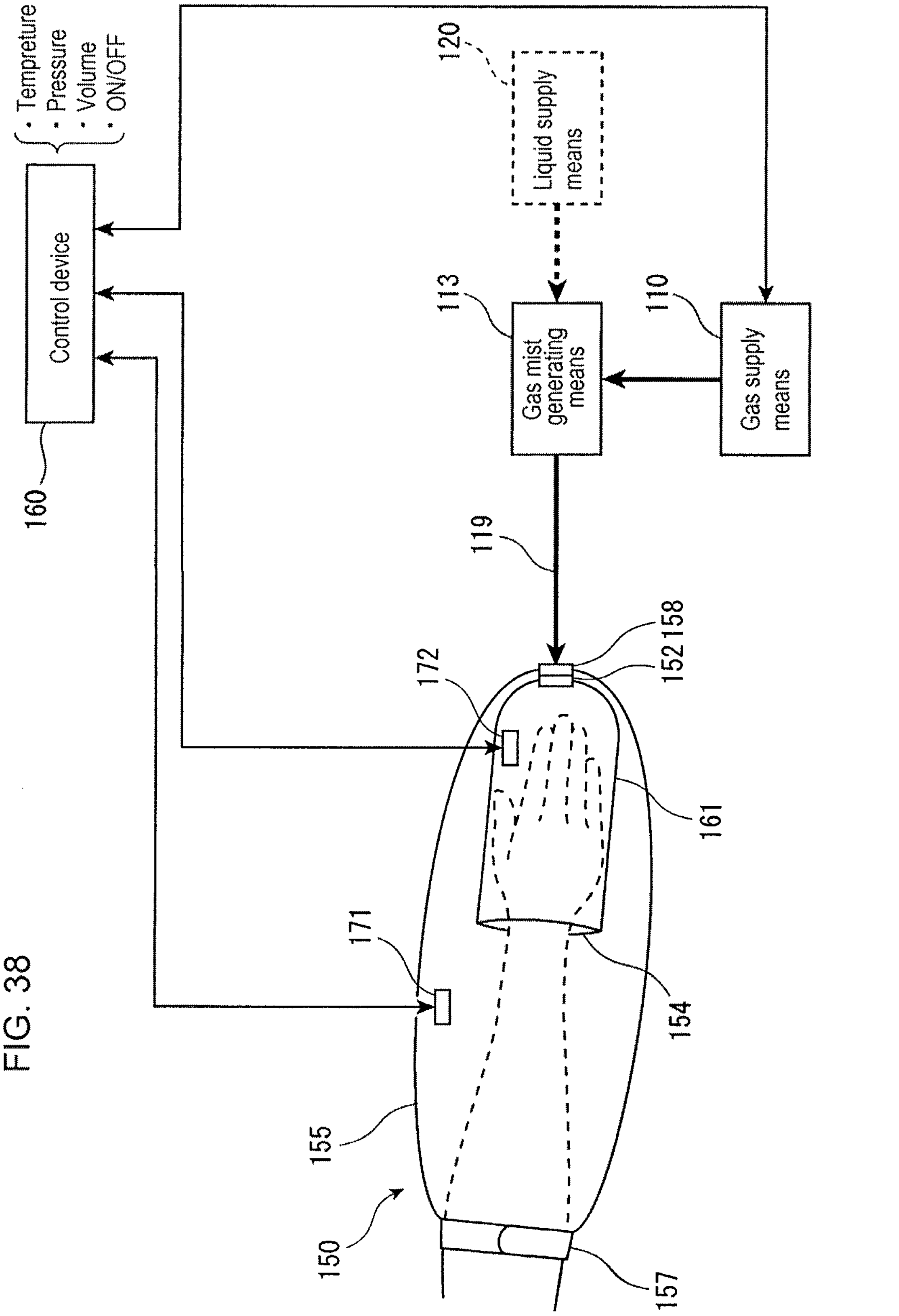
FIG. 38 A typical view showing the outline of Third Embodiment of the carbon dioxide gas mist pressure bath apparatus depending on the invention, using the pressure bath cover shielding the skin and the mucous membrane at parts of the body.

The pressure bath covers 12, 22, 32, 32*a* and 32*b* having been explained until now receive all of the living body excepting a head part, and those covering the skin and mucous membrane of local parts of the body are still sufficient. FIG. 38 is the typical view showing the outline of the third embodiment of the carbon dioxide gas mist pressure bath apparatus according to the present invention. The pressure bath cover 150 herein covers a local part of the living body (FIG. 38 shows, as an example, a forearm of the human body), and forms the space for sealing inside the gas mist and gas. The pressure bath cover 150 is composed of a first cover 161 (an inner cover) positioned inside and a second cover 155 (an outer cover) positioned outside and covering the whole of the first cover 161, almost enabling to close. The pressure bath cover 150 is suitably composed of a pressure resistant, non-air permeable and non-moisture permeable materials, and for example, a natural rubber, silicone rubber, polyethylene, poly-propylene, polyvinylidene, polystyrene, polyvinyl acetate, polyvinyl chloride, polyamide resin, polytetrafluoroethylene.

The inner cover 161 is an almost bag shaped cover for partially covering parts of high absorption rate of the gas mist, and concurrently serves as a cover of heat insulation. That is, temperature heightens in the pressure bath cover 150 as time passes, and then the gas mist of comparatively cool temperature generated at room temperature is supplied, but the inner cover 161 is preferably composed of a heat insulating material not to heighten temperature. By attaching the inner cover

161, the gas mist supplied during taking the gas mist pressure bath can be avoided from gasification. The inner cover 161 is higher in effects by attaching to parts requiring in particular the gas mist to be absorbed, palms, planters, or easily sweating in parts of many sweat glands.

The inner cover 161 has an inlet port 152 connected to the gas mist supply pipe 119 for introducing inside the gas mist and gas. The inlet port 152 is, though not shown, provided inside with a check valve for avoiding back flow of the gas mist and gas. The inner cover 161 is an open 154 in this embodiment. Accordingly, the gas mist and gas supplied in the inner cover 161 are also concurrently supplied to an outer cover 155 through the open 154.

The outer cover 155 is larger than the inner cover 161, enables to cover the skin and mucous membrane of the living organism and the whole of the inner cover 161, and is formed as an almost bag shaped cover. The outer cover 155 is provided at its opening part with a stopper 157 which enables to attach to and detach from the living organism and prevents leakage of the gas mist and gas. The stopper 157 is preferably composed of a face fastener having, e.g., stretchability. Otherwise, a string or rubber or the like may be used solely or in combination. Since the outer cover 155 necessitates sealing property, the stopper 157 may have inside such a material adhering to the skin of the living organism. This adhesive material is desirably a visco-elastic gel made of polyurethane or silicone rubber. In addition, this visco-elastic material is detachably furnished, and can be desirably exchanged if viscosity becomes lower.

Further, the outer cover 155 has a connecting part 158 which is connected to the inlet port 152 of the inner cover 161 and connects the inner cover 161 and the carbon dioxide gas mist supply pipe 119 while sealing the outer cover 155. Desirably, the outer cover 155 is, though not shown, provided with a gas mist exhaust port for getting out the gas mist and gas from the inside of the cover, and with a valve for adjusting pressure of the inside of the cover. The adjustment of pressure within the cover may depend on manual operation, but desirably it depends on automatic operation by a control device 160 together with supply control of the gas mist. Further, there is desirably provided a safety valve (dischargeable valve) which opens automatically when the inside of the outer cover 155 exceeds a predetermined pressure value.

The example herein is that the connecting part 158 is connected to the inlet port 152, and any embodiments are applicable, as far as being such a structure enabling to supply the gas mist into the inner cover 161 while closing the inside of the outer cover 155.

Inside of the outer cover 155, a manometer 171 is placed for measuring its inside pressure. The control device 160 controls generation and supply of the gas mist based on the measuring values of the manometer 171 for keeping the pressure value inside the outer cover 155 to be 1 air pressure or higher (to be more preferably, 1.01 to 2.5 air pressure). For example, the supply of gas from a gas supply means 110 is controlled or stopped, and the gas mist and gas are discharged from the inner cover 161 or the outer cover 155. By the way, since this embodiment uses the pressure bath cover 150 of the inner cover 161 opening by an open 154, the manometer 171 is enough with one provided in the outer cover 155. Within the inner cover 161 or within the outer cover 155 (herein, within the inner cover 161), a thermometer 172 may be installed for measuring temperature. The control device 160 performs “ON-OFF” of supplying the gas mist.

As to others, within the pressure bath cover 150, there may be installed sensors for measuring the concentrations of oxygen, of carbon dioxide or of moisture in order to control the circumstances in the covers to be within predetermined ranges of respective values by a control device 160.

The control device 160 is composed of a computer having CPU, memory and display, and performs each of controls such as gas pressure control or ON-OFF switch, or ON-OFF switch of the gas mist supply for taking the gas mist pressure bath under optimum conditions. In particular, the control device 160 adjusts each of several means from measuring values of the manometer 171 or thermometer 172 installed in the pressure bath cover 150 in order to maintain optimum conditions for taking the gas mist pressure bath. It is suitable to make such a structure that, if the pressure value in the pressure bath cover 150 becomes higher than the predetermined value, the gas supply of the gas supply means 110 is stopped by the control device 160. The above control may be manual, not using the control device 160.

As to many animal tests showing improvements of myocardial infarction diseases by the carbon dioxide pressure bath treatment depending on the invention, explanations will be made, referring to Tables and Figures (graphs).

Figure 11:
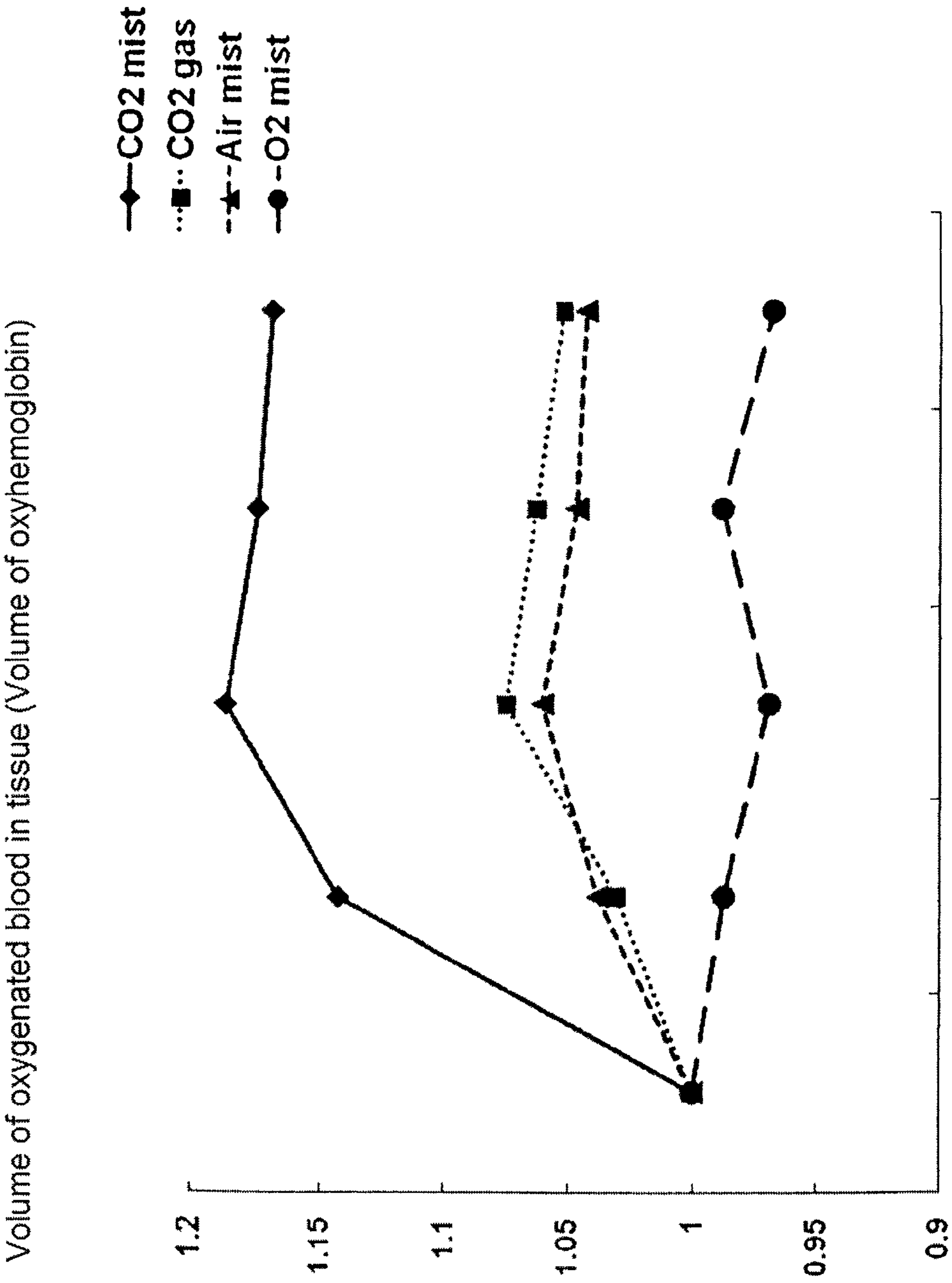
FIG. 11 A view explaining comparison among the four groups of the volume of oxygenerated blood (the volume of oxyhemoglobin) in the tissue.

(1) Comparison Among Four Groups of Oxygenerated Blood Volume (Volume of Oxyhemoglobin) in the Tissue (Table 1 and FIG. 11)

The compositions of gases sealed under pressure in the carbon dioxide gas mist pressure bath means were subjected to the experiments using the four kinds of air mist (AM), $CO_2$ gas (CG), $CO_2$ mist (CM) and 100% oxygen mist (OM). Each of gases was sealed under pressure in the carbon dioxide gas mist pressure bath means, and the treatments were practiced. The numbers of the individuals were 13, 14, 15 and 11 pieces, respectively. Each of the individuals was intubated into male wistar rats aged of 8 weeks under the pentobarbital anesthesia, subjected to the thoracotomy, and was ligated at the coronary left-front rami descendens for making models of myocardial infarction.

As to the treatments to these individuals by the four kinds of gases, the laser tissue blood oxygen monitor carried out measures on the pre-treatment (pre), the respective conditions at 10 min, 20 min and 30 min after starting the treatments, and the volume of oxygenated blood (volume of oxyhemoglobin) in the tissue of the individuals under the conditions (post) after finishing the treatments, and the measured results are shown in Table 1.

TABLE 1

Basic Statistics: oxyHb
Effects: Category oxyHb * group
Exclusion of Line: oxyHb.svd

| | Number of Examples | Average Value | Standard Deviation | Standard Error |
|---|---|---|---|---|
| AM, pre | 13 | 1.000 | 0.000 | 0.000 |
| AM, oxyHb 10 min | 13 | 1.038 | .064 | .018 |
| AM, oxyHb 20 min | 13 | 1.060 | .089 | .025 |
| AM, oxyHb 30 min | 13 | 1.046 | .109 | .030 |
| AM, post | 13 | 1.042 | .117 | .032 |
| CG, pre | 14 | 1.000 | 0.000 | 0.000 |
| CG, oxyHb 10 min | 14 | 1.030 | .076 | .020 |
| CG, oxyHb 20 min | 14 | 1.074 | .109 | .029 |
| CG, oxyHb 30 min | 14 | 1.062 | .142 | .038 |
| CG, post | 14 | 1.051 | .179 | .048 |
| CM, pre | 15 | 1.000 | 0.000 | 0.000 |
| CM, oxyHb 10 min | 15 | 1.142 | .197 | .051 |
| CM, oxyHb 20 min | 15 | 1.187 | .211 | .054 |
| CM, oxyHb 30 min | 15 | 1.174 | .181 | .047 |
| CM, post | 15 | 1.168 | .177 | .046 |
| OM, pre | 11 | 1.000 | 0.000 | 0.000 |
| OM, oxyHb 10 min | 11 | .987 | .068 | .021 |
| OM, oxyHb 20 min | 11 | .969 | .072 | .022 |

TABLE 1-continued

| Basic Statistics: oxyHb<br>Effects: Category oxyHb * group<br>Exclusion of Line: oxyHb.svd | Number of Examples | Average Value | Standard Deviation | Standard Error |
|---|---|---|---|---|
| OM, oxyHb 30 min | 11 | .987 | .118 | .036 |
| OM, post | 11 | .967 | .134 | .040 |

To concretely explain Table 1, the air mist (AM) was experimented on the 13 individuals, and the laser tissue blood oxygen monitor carried out measures on the pre-treatment (pre), the conditions at 10 min, 20 min and 30 min after the treatments and the volumes of oxyhemoglobin of the respective individuals under the conditions (post) after the treatments. Then, "reference values" were made from values when having calculated the average values of the volume of oxyhemoglobin of the 13 individuals measured with the blood flow meter before the treatments, and Table expresses this average values as "1.000".

The average values calculated from the amount of oxyhemoglobin of 13 individuals measured when passing 10 minutes after starting the treatments, were compared with the above mentioned reference values. In this case, the average values of the volume of oxyhemoglobin of the 13 individuals increased and showed 1.038. The cases at 20 min, 30 min after starting the treatments and the post were also similar, and all of the average values of the volume of oxyhemoglobin exceeded 1.000.

Similarly, also concerning the respective treatments of the three kinds of $CO_2$ gas (CG), $CO_2$ mist (CM) and 100% oxygen mist (CM), the "reference values" were made from values when having calculated the average values of the volume of oxyhemoglobin of the individuals measured, at the pre-treatment (pre), by the laser tissue blood oxygen monitor, and Table 1 showed this as the average value of 1.000. With respect to the average values of the volume of oxyhemoglobin of the respective individuals at 20 min, 30 min after starting the treatments and at the case of post, the above mentioned reference value made the division calculation on the value when having calculated the reference value of the volumes of oxyhemoglobin of the respective individuals, and the values calculated by the division are shown as the average values.

Table 1 is shown with the bending lines of interaction in FIG. 11. It shows that the amount of oxyhemoglobin increases by the treatment of CO mist (CM), in short, hemoglobin combined with oxygen increases. On the other hand, also in the cases of the treatments by the air mist (AM) or by $CO_2$ gas (CG), though not significant, increase of the amount of oxyhemoglobin was recognized. As to the air mist, since $CO_2$ is contained in air, a tendency was similar to the treatment with $CO_2$ mist (CM). However, by the treatment of $CO_2$ mist (CM), the amount of oxyhemoglobin most increased.

On the other hand, in the case of 100% oxygen mist (OM), it is shown that the amount of oxyhemoglobin did not increase in spite of the treatment, and the blood circulation was not improved.

Figure 12:
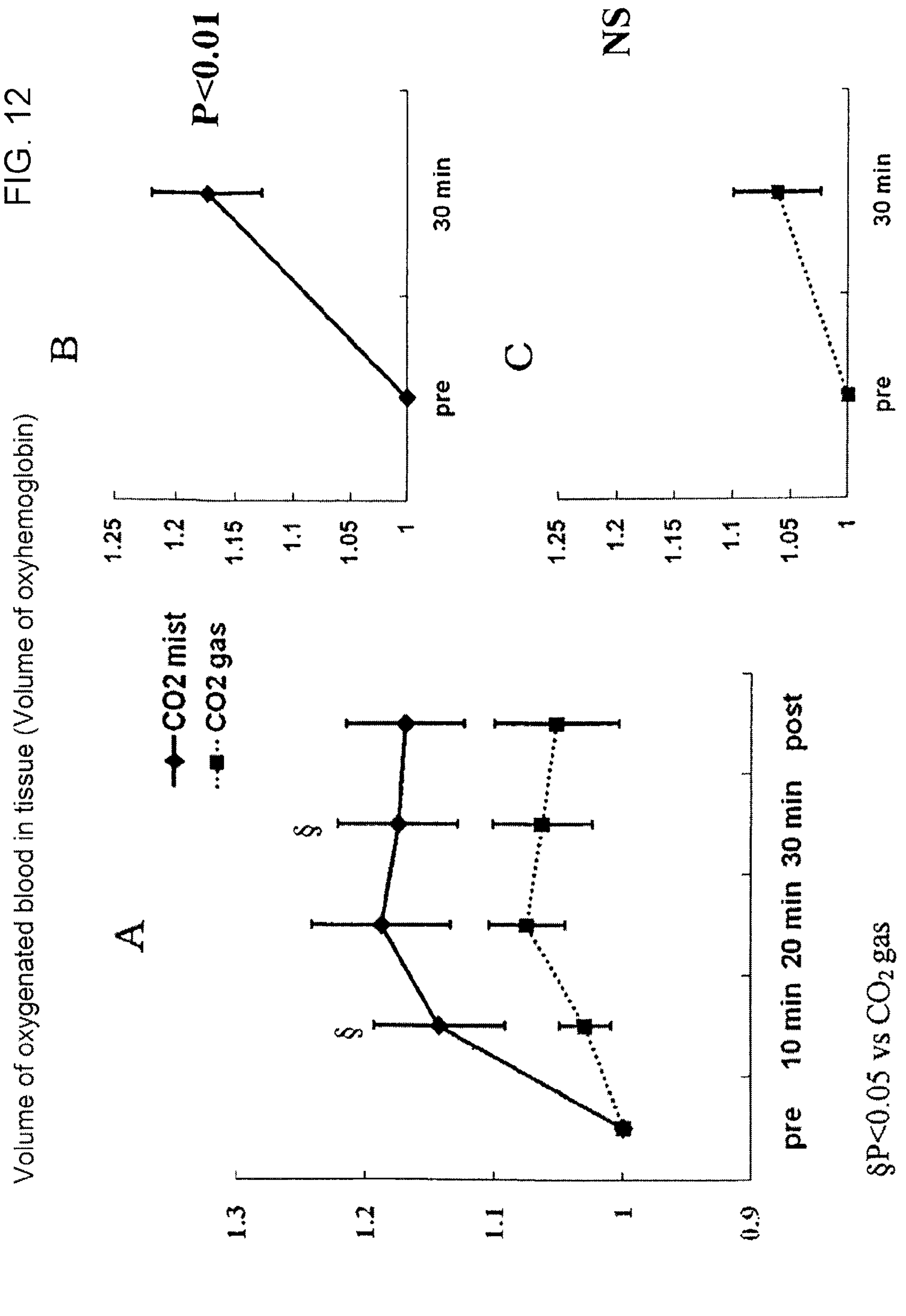
FIG. 12 Views explaining comparison between the two groups of the volume of oxygenerated blood (the volume of oxyhemoglobin) in the tissue.

(2) Comparison (FIG. 12) Between Two Groups of Oxygenerated Blood Volume (the Volume of Oxyhemoglobin) in the Tissue FIG. 12 shows, in A part, changes in time sequence of the volume of oxyhemoglobin in the respective treatments between two groups of $CO_2$ gas (CG) and $CO_2$ mist (CM) with the bending lines of interaction, and B and C parts of FIG. 12 show, with the bending lines, the increases in the averages of the volume of oxyhemoglobin under the condition 30 minutes passing after the treatment started. The volume of oxyhemoglobin after 10 minutes of the treatment of $CO_2$ mist (CM) recognized the increase, and recognized the significant difference, comparing the increasing amount with $CO_2$ gas (CG). Also after 20 minutes, the increase in the volume of oxyhemoglobin continued. In the comparison at the point of 30 minutes of the treatments, while $CO_2$ mist (CM) increased significantly the volume of oxyhemoglobin (B part of FIG. 12), $CO_2$ gas (CG) did not recognize the significant increase of the volume of oxyhemoglobin (C part of FIG. 12) This fact shows that the treatment by $CO_2$ mist (CM) containing $CO_2$ in the mist had the increasing effect of the volume of oxyhemoglobin than the treatment of $CO_2$ gas (CG).

(3) Comparison (Table 2 and FIG. 13) Among Four Groups of Deoxygenerated Blood Volume (the Volume of Deoxyhemoglobin) in the tissue

TABLE 2

| Basic Statistics: deoxyHb<br>Effects: Category deoxyHb * group<br>Exclusion of Line: deoxyHb.svd | Number of Examples | Average Value | Standard Deviation | Standard Error |
|---|---|---|---|---|
| AM, pre | 13 | 1.000 | 0.000 | 0.000 |
| AM, deoxyHb 10 min | 13 | .992 | .038 | .011 |
| AM, deoxyHb 20 min | 13 | .968 | .049 | .013 |
| AM, deoxyHb 30 min | 13 | .951 | .054 | .015 |
| AM, post | 13 | .944 | .056 | .016 |
| CG, pre | 14 | 1.000 | 0.000 | 0.000 |
| CG, deoxyHb 10 min | 14 | .974 | .029 | .008 |
| CG, deoxyHb 20 min | 14 | .942 | .044 | .012 |
| CG, deoxyHb 30 min | 14 | .930 | .047 | .012 |
| CG, post | 14 | .915 | .056 | .015 |
| CM, pre | 15 | 1.000 | 0.000 | 0.000 |
| CM, deoxyHb 10 min | 15 | .958 | .042 | .011 |
| CM, deoxyHb 20 min | 15 | .912 | .063 | .016 |
| CM, deoxyHb 30 min | 15 | .892 | .066 | .017 |
| CM, post | 15 | .870 | .059 | .015 |
| OM, pre | 11 | 1.000 | 0.000 | 0.000 |
| OM, deoxyHb 10 min | 11 | .998 | .057 | .017 |
| OM, deoxyHb 20 min | 11 | .986 | .097 | .029 |
| OM, deoxyHb 30 min | 11 | .961 | .096 | .029 |
| OM, post | 11 | .957 | .100 | .030 |

Table 2 shows the results of measuring the deoxygenated blood volume (the volume of deoxyhemoglobin) in the tissue with a blood flow meter when sealing under pressure the same four kinds of gases to the same individual groups as those of Table 1 into the carbon dioxide gas mist pressure bath means. The measures at this time also performed in each of the treatments as the pre-treatment (pre), the respective conditions of passing 10 min, 20 min and 30 min after starting the treatments, under the conditions (post) after finishing the treatments. In the results of measuring the treatments of the respective gases, "reference values" were made from values when calculating the average values of the volume of deoxyhemoglobin, the average value was expressed with "1.000" in this Table. The above mentioned reference values made the division calculation on the values when calculating the average values of the amount of deoxyhemoglobin of the respective individuals measured by the laser tissue blood oxygen monitor in the pre-treatment (pre) in the respective individuals of the cases of passing 20 min, 30 min and the condition (post) after finishing the treatments, and the values calculated by the division are shown as the average values.

Figure 13:
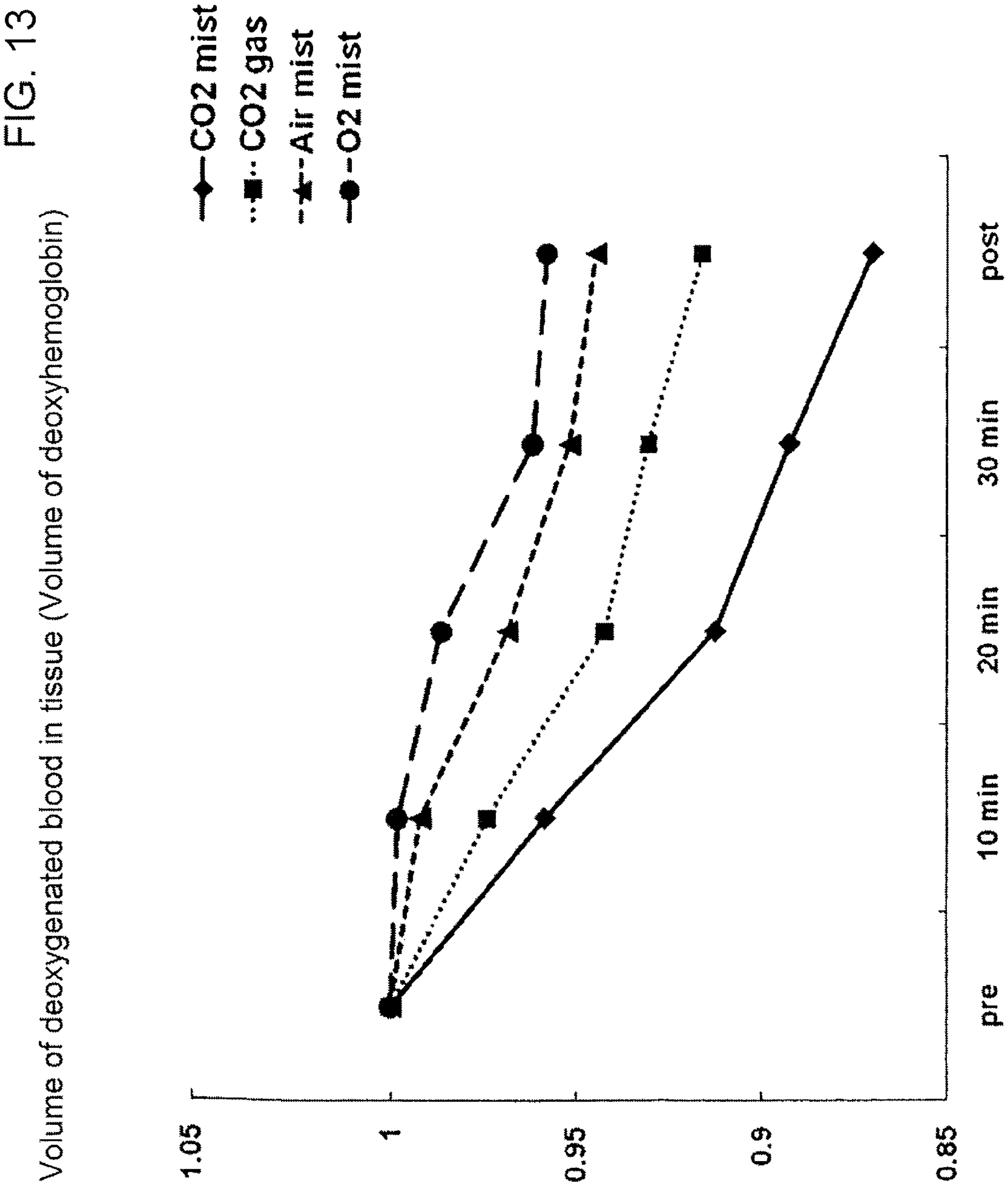
FIG. 13 A view explaining comparison among the four groups of the volume of deoxygenerated blood (the volume of deoxyhemoglobin) in the tissue.

Table 2 is shown with the bending lines of interaction in FIG. 13. The volume of deoxyhemoglobin also decreased in each of all the gas treatments of the four kinds of the pre-treatment (pre), at 10 min, 20 min, 30 min passing after starting the treatments and the condition (post) after finishing the treatments. This fact shows that since hemoglobin combines oxygen by the treatment and increases oxyhemoglobin, hemoglobin relatively not combining oxygen (in short, deoxyhemoglobin) decreases. Each of the treatments shows the tendency of deoxyhemoglobin decreasing, in particular, decrease of deoxyhemoglobin in the treatment by $CO_2$ mist (CM) is remarkable in comparison with other gases.

Figure 14:
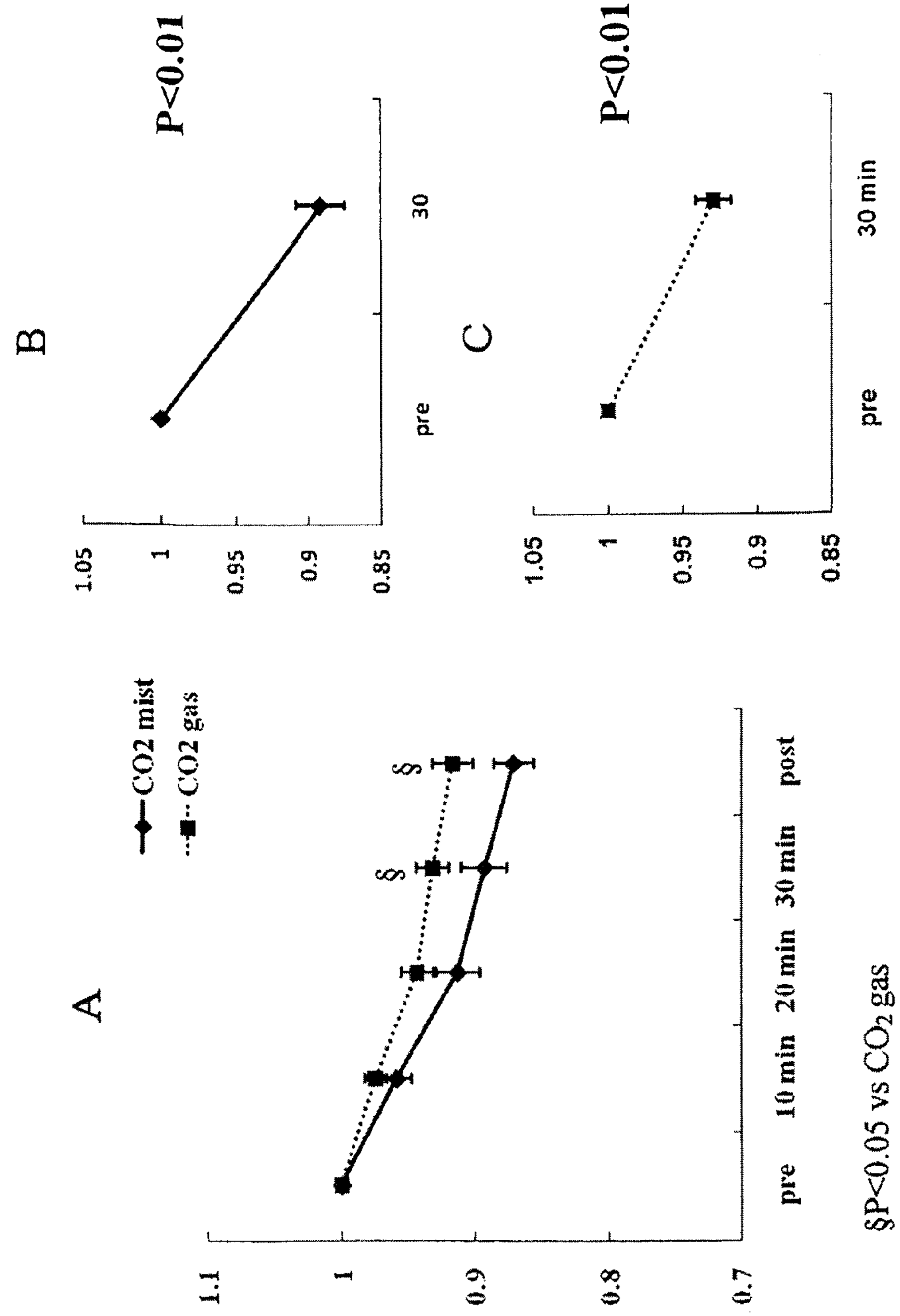
FIG. 14 Views explaining comparison between the two groups of the volume of deoxygenerated blood (the volume deoxyhemoglobin) in the tissue.

(4) Comparison (FIG. 14) Between Two Groups of Deoxygenerated Blood Volume (the Volume of Deoxyhemoglobin) in the Tissue FIG. 14 shows, in A part, the changes in time sequence of the volume of deoxyhemoglobin in the respective treatments between two groups of $CO_2$ gas (CG) and $CO_2$ mist (CM) with the bending lines of interaction, and B and C parts of FIG. 14 show, with the bending lines, the increases of the averages of the volume of deoxyhemoglobin under the condition 30 minutes passing after the treatment. As FIG. 14 showing, in A part, both of $CO_2$ gas (CG) and $CO_2$ mist (CM) recognize the decreasing tendencies at 10 minutes after the treatment, and after 30 minutes, $CO_2$ mist recognizes the significant decrease of the volume of deoxyhemoglobin in comparison with $CO_2$ gas. In comparison at the point of 30 minutes of the treatments, the volumes of deoxyhemoglobin of both groups decrease significantly, and as showing in B and C parts of FIG. 14, the lowering rate is remarkable in $CO_2$ mist (CM) than $CO_2$ gas (CG). This fact says that the treatment by $CO_2$ mist (CM) containing $CO_2$ in the mist shows that hemoglobin not combining with oxygen (in short, the volume of oxyhemoglobin) has the decreasing effect of the volume of oxyhemoglobin than the treatment of $CO_2$ gas (CG).

(5) Comparison Among Four Groups (Table 3 and FIG. 15) of Volume of Total Blood (the Volume of Total Hemoglobin) in the Tissue

TABLE 3

Basic Statistics: total Hb
Effects: Category total Hb * group
Exclusion of Line: total Hb.svd

| | Number of Examples | Average Value | Standard Deviation | Standard Error |
|---|---|---|---|---|
| AM, pre | 13 | 1.000 | 0.000 | 0.000 |
| AM, total Hb 10 min | 13 | 1.013 | .036 | .010 |
| AM, total Hb 20 min | 13 | 1.010 | .054 | .015 |
| AM, total Hb 30 min | 13 | .993 | .066 | .018 |
| AM, post | 13 | .987 | .073 | .020 |
| CG, pre | 14 | 1.000 | 0.000 | 0.000 |
| CG, total Hb 10 min | 14 | 1.002 | .032 | .009 |
| CG, total Hb 20 min | 14 | 1.010 | .048 | .013 |
| CG, total Hb 30 min | 14 | .995 | .064 | .017 |
| CG, post | 14 | .981 | .077 | .021 |
| CM, pre | 15 | 1.000 | 0.000 | 0.000 |
| CM, total Hb 10 min | 15 | 1.047 | .080 | .021 |
| CM, total Hb 20 min | 15 | 1.046 | .083 | .021 |
| CM, total Hb 30 min | 15 | 1.031 | .079 | .020 |
| CM, post | 15 | 1.018 | .085 | .022 |
| OM, pre | 11 | 1.000 | 0.000 | 0.000 |
| OM, total Hb 10 min | 11 | .995 | .049 | .015 |
| OM, total Hb 20 min | 11 | .979 | .064 | .019 |
| OM, total Hb 30 min | 11 | .975 | .089 | .027 |
| OM, post | 11 | .962 | .101 | .031 |

Table 3 shows the results of measuring the volume of total hemoglobin with the laser tissue blood oxygen monitor when sealing under pressure the same four kinds of gases into the carbon dioxide gas mist pressure bath means with respect to the same individual groups as those of Table 1. The measures performed, also at this time, in each of the gas treatments of the pre-treatment (pre), the respective conditions of 10 min, 20 min, 30 min after starting the treatment, and under the conditions (post) after finishing the treatments. In the results of measuring the treatments of the respective gases, making "reference values" from values when having calculated the average values of the volume of total hemoglobin, the average value is expressed with "1.000" in this Table. The above mentioned reference values made the division calculation on the values when having calculated the average values of the amount of total hemoglobin of the respective individuals measured by the blood flow meter in the pre-treatment (pre) in the respective individuals of the cases of passing 10 min, 20 min, 30 min and the post after starting the treatment, and the values calculated by the division are shown as the average values.

Figure 15:
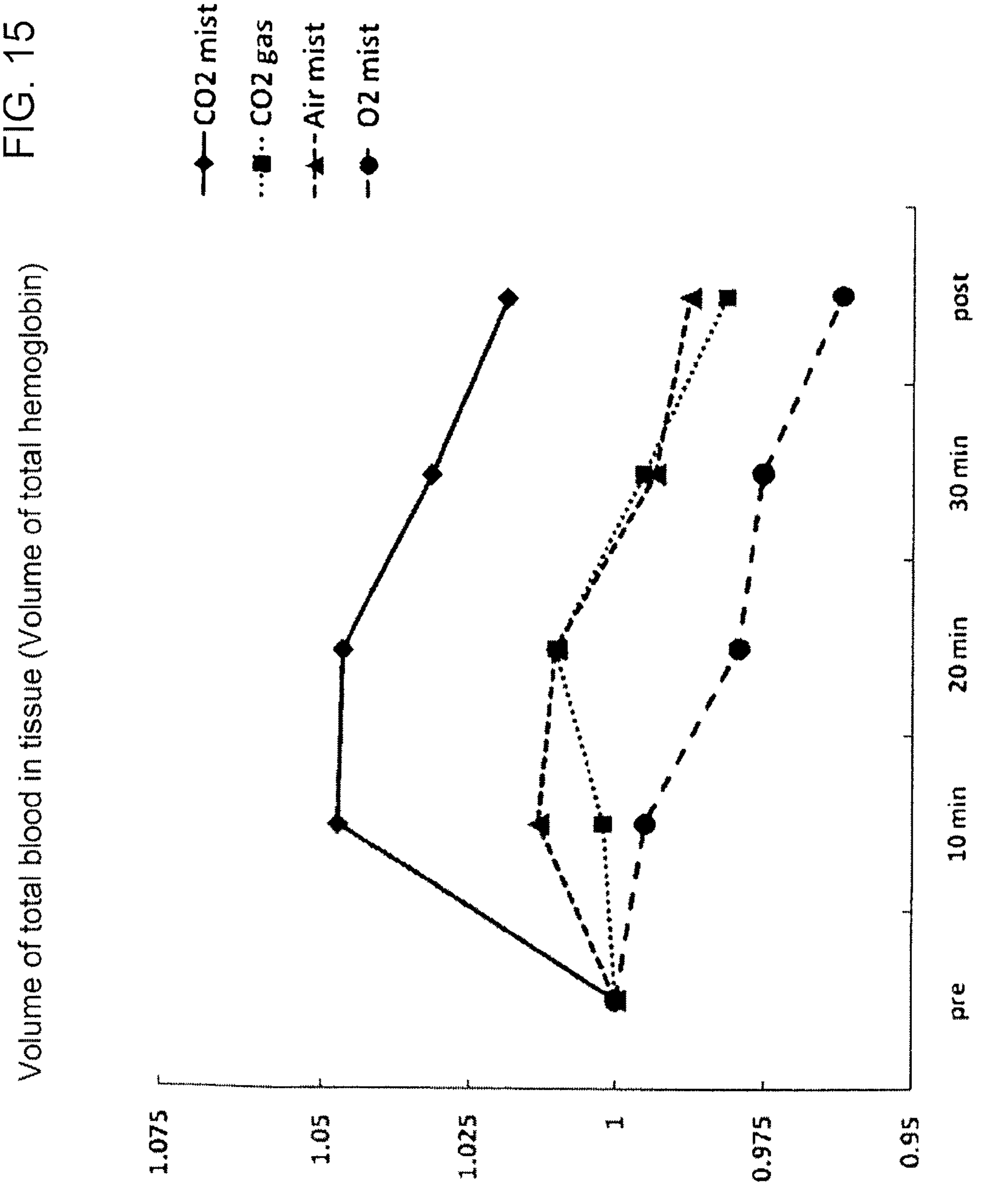
FIG. 15 A view explaining comparison among the four groups of the volume of total blood (the volume of total hemoglobin) in the tissue.

Table 3 is shown with the bending lines of interaction in FIG. 15. $CO_2$ mist (CM) and the air mist (AM) show the maximum value of the volumes of total hemoglobin, and after then show the decreasing tendencies. In spite of them, $CO_2$ mist (CM) shows the higher numerical value than that of the pre-treatment (pre), but in the air mist (AM), the numerical value is lower at 30 minutes after starting the treatment than that of the pre-treatment (pre). In $CO_2$ gas (CG) at 20 minutes after starting the treatment, the maximum value of the volume of total hemoglobin appears, and after then, the decreasing tendency is shown, and at 30 minutes after starting the treatment, the numerical value becomes lower. In short, in the treatments of $CO_2$ mist (CM), the air mist (AM) and $CO_2$ (CG), the total hemoglobin once increases and after then decreases, but only $CO_2$ mist (CM) exceeds the volume of total hemoglobin, and the improving effect of the blood circulation is recognized. Nevertheless, in the case of 100% oxygen mist (OM), the volume of total hemoglobin decreases in spite of the treatment, the blood circulation is not improved.

Figure 16:
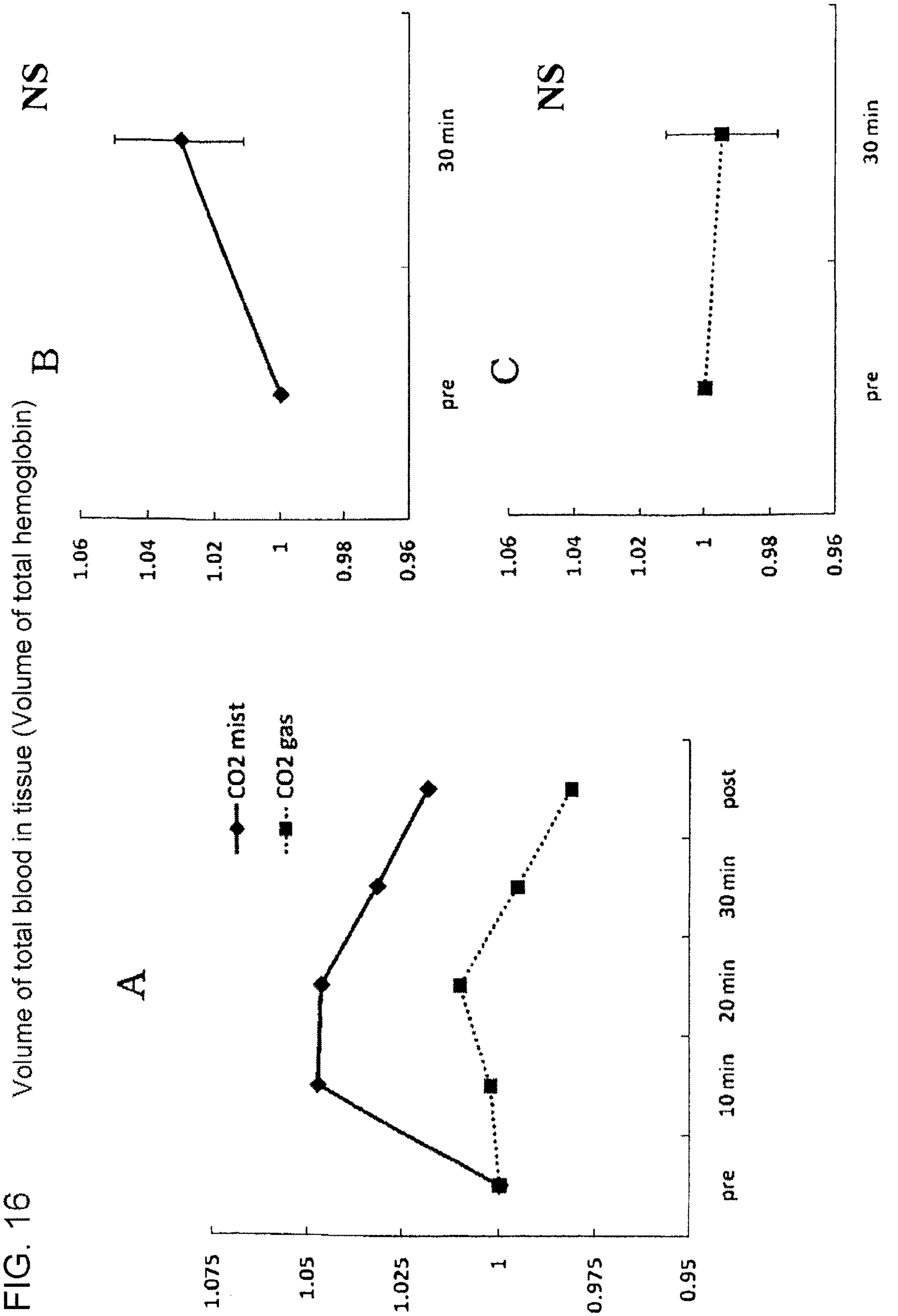
FIG. 16 Views explaining comparison between the two groups of the volume of total blood (the volume of total hemoglobin) in the tissue.

(6) Comparison Between Two Groups of Volume of Total Blood (Volume of Total Hemoglobin) in the Tissue FIG. 16 shows, with the bending lines of interaction, in A part, changes in time sequence of the volumes of total hemoglobin in the respective treatments between two groups of $CO_2$ gas (CG) and $CO_2$ mist (CM), and B and C parts of FIG. 16 show, with the bending lines, the increases of the averages of the volume of oxyhemoglobin under the condition at 30 minutes after starting the treatment. As shown in A part of FIG. 16, as to $CO_2$ mist (CM), the maximum value of the volume of total hemoglobin appears at 10 minutes after starting the treatment, and after then, decreases. Nevertheless, $CO_2$ mist (CM) shows high values in comparison with the pre-treatment (pre). On the other hand, as shown in B part and C part of FIG. 16, in $CO_2$ gas (CG), the volume of total hemoglobin shows the maximum value, and after then, shows the decreasing tendency, and at 30 minutes after starting the treatment, the values become lower than that of the pre-treatment (pre). This fact says that the treatment by $CO_2$ mist (CM) containing $CO_2$ in the mist has increase of the volume of total hemoglobin, that is, the improving effect of the blood circulation than the treatment of $CO_2$ gas (CG).

(7) Comparison Among Four Groups (Table 4 and FIG. 17) of Degrees of Oxygen Saturation in Blood (StO2) in the Tissue

TABLE 4

Basic Statistics: StO2
Effects: Category StO2 * group
Exclusion of Line: StO2.svd

| | Number of Examples | Average Value | Standard Deviation | Standard Error |
|---|---|---|---|---|
| AM, pre | 13 | 1.000 | 0.000 | 0.000 |
| AM, StO2 10 min | 13 | 1.024 | .039 | .011 |
| AM, StO2 20 min | 13 | 1.049 | .045 | .012 |
| AM, StO2 30 min | 13 | 1.051 | .055 | .015 |
| AM, post | 13 | 1.053 | .056 | .016 |
| CG, pre | 14 | 1.000 | 0.000 | 0.000 |
| CG, StO2 10 min | 14 | 1.027 | .045 | .012 |
| CG, StO2 20 min | 14 | 1.061 | .063 | .017 |
| CG, StO2 30 min | 14 | 1.063 | .079 | .021 |
| CG, post | 14 | 1.065 | .107 | .029 |
| CM, pre | 15 | 1.000 | 0.000 | 0.000 |
| CM, StO2 10 min | 15 | 1.086 | .099 | .026 |
| CM, StO2 20 min | 15 | 1.128 | .114 | .030 |
| CM, StO2 30 min | 15 | 1.134 | .100 | .026 |
| CM, post | 15 | 1.143 | .094 | .024 |
| OM, pre | 11 | 1.000 | 0.000 | 0.000 |
| OM, StO2 10 min | 11 | .991 | .038 | .011 |
| OM, StO2 20 min | 11 | .990 | .058 | .017 |
| OM, StO2 30 min | 11 | 1.011 | .051 | .015 |
| OM, post | 11 | 1.003 | .053 | .016 |

Table 4 shows the results of measuring the degree of oxygen saturation in blood in the tissue with the blood flow meter when sealing under pressure the same four kinds of gases into the carbon dioxide gas mist pressure bath means with respect to the same individual groups as those of Table 1. The measures at this time also performed in each of the gas treatments as the pre-treatment (pre), the respective conditions at 10 min, 20 min and 30 min after starting the treatments, under the conditions (post) after finishing the treatments. In the results of measuring the treatments of the respective gases, making "reference values" from values when having calculated the average values of StO2, the average value is expressed with "1.000" in this Table, and the above mentioned reference values make the division calculation on the average values of StO2 in the respective individuals of the cases of passing 20 min, 30 min and the post after starting the treatments by respective gases, and the average values are thus made. StO2 increases in any of the respective conditions of passing 10 min, 20 min, 30 min after starting the treatments, and in the conditions (post) after finishing the treatments. This shows that the blood circulation is improved by the procedures, and StO2 increases. Each of the procedures shows the tendency after passing of the treatment times, and in particular, the treatment by $CO_2$ mist (CM) shows the increase of StO2 is larger than other gases. On the other hand, as to the air mist (AM) and $CO_2$ gas (CG), in any of the respective conditions at 20, 30 minute after starting the treatments and the condition (post) after the treatments, StO2 shows the tendency of saturation.

On the other hand, in the case of 100% oxygen mist (OM), StO2 increases a little at 30 minutes after the treatment begins, but under other conditions, it decreases or shows an average value.

Figure 17:
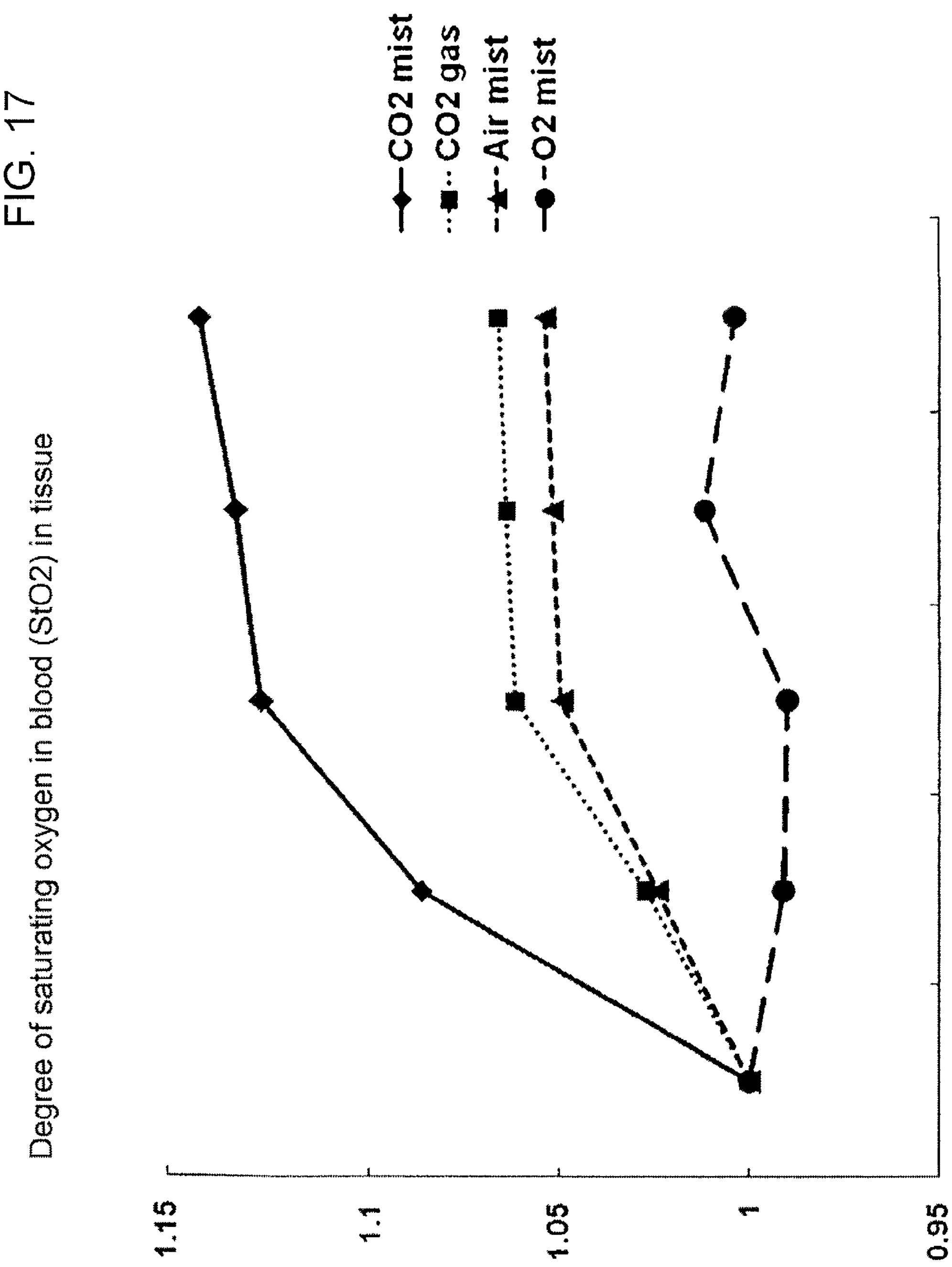
FIG. 17 A view explaining comparison among the four groups of the degree of saturated oxygen of blood (StO2) in the tissue.

Table 4 is shown with the interaction bending lines in FIG. 17. StO2 increases remarkably in the case of $CO_2$ mist (CM), and StO2 increases until 20 minutes after the treatment starts in the cases of the air mist (AM) and $CO_2$ gas (CG) but after then it is under saturation.

In the case of 100% oxygen mist (OM), StO2 increases a little after 30 minutes after the treatment begins, but under other conditions, it decreases or shows an average value.

Figure 18:
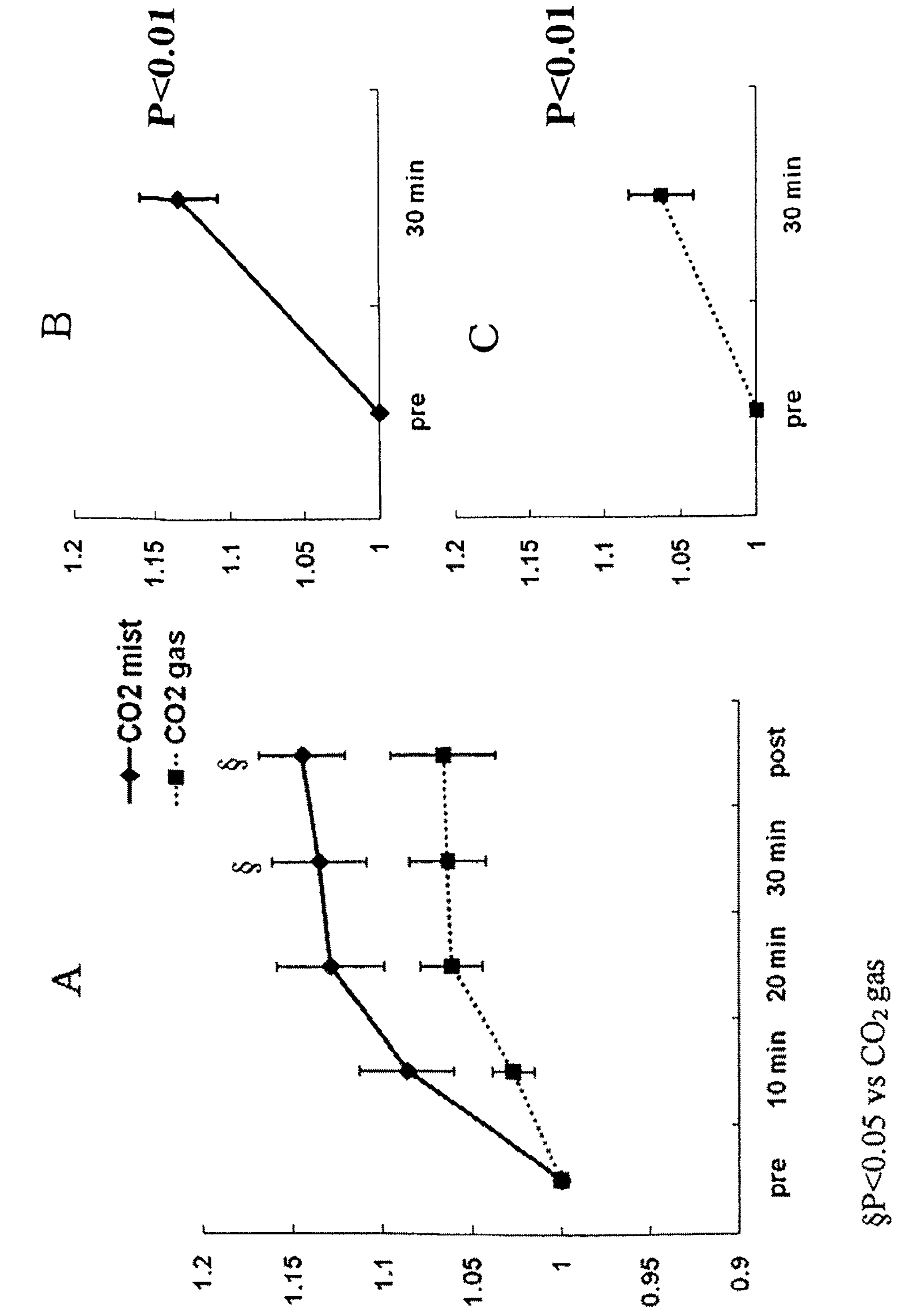
FIG. 18 Views explaining comparison between the two groups of the degree of saturated oxygen of blood (StO2) in the tissue.

(8) Comparison Between Two Groups of the Degree of Saturated Oxygen in Blood (StO2) in the Tissue (FIG. 18)

FIG. 18 shows, in A part, with the interaction bending lines the changes in time sequence of the degree of saturated oxygen of blood (StO2) in the tissue by the treatments between the two groups, while FIG. 18 shows in B and C parts with the bending lines the average values of the degree of saturated oxygen of blood (StO2) in the tissue at the time point of 30 minutes after starting the treatments. As to $CO_2$ mist (CM), at 10 minutes after starting the treatments, the degree of saturated oxygen of blood (StO2) in tissue increases, the significant difference from $CO_2$ gas (CG) is recognized at 20 minutes after starting the treatment. Also, as to $CO_2$ gas (CG), at 10 minutes after starting the treatment, but at 30 minutes after starting the treatment, the degree of saturated oxygen of blood (StO2) in the tissue shows the saturating tendency, and thereafter, increase is not recognized. In the comparison at 30 minutes after starting the treatment, as showing in B and C parts of FIG. 12, the degree of saturated oxygen of blood (StO2) in the tissue increases in both parts, but the increasing rate is remarkable in $CO_2$ mist (CM) than $CO_2$ gas (CG).

This fact shows that the treatment by $CO_2$ mist (CM) containing $CO_2$ in the mist is higher in the increasing effect of the degree of saturated oxygen of blood (StO2) in the tissue than the treatment of $CO_2$ gas (CG), and the effect by $CO_2$ (CM) is higher than that of $CO_2$ gas (CG).

Figure 19:
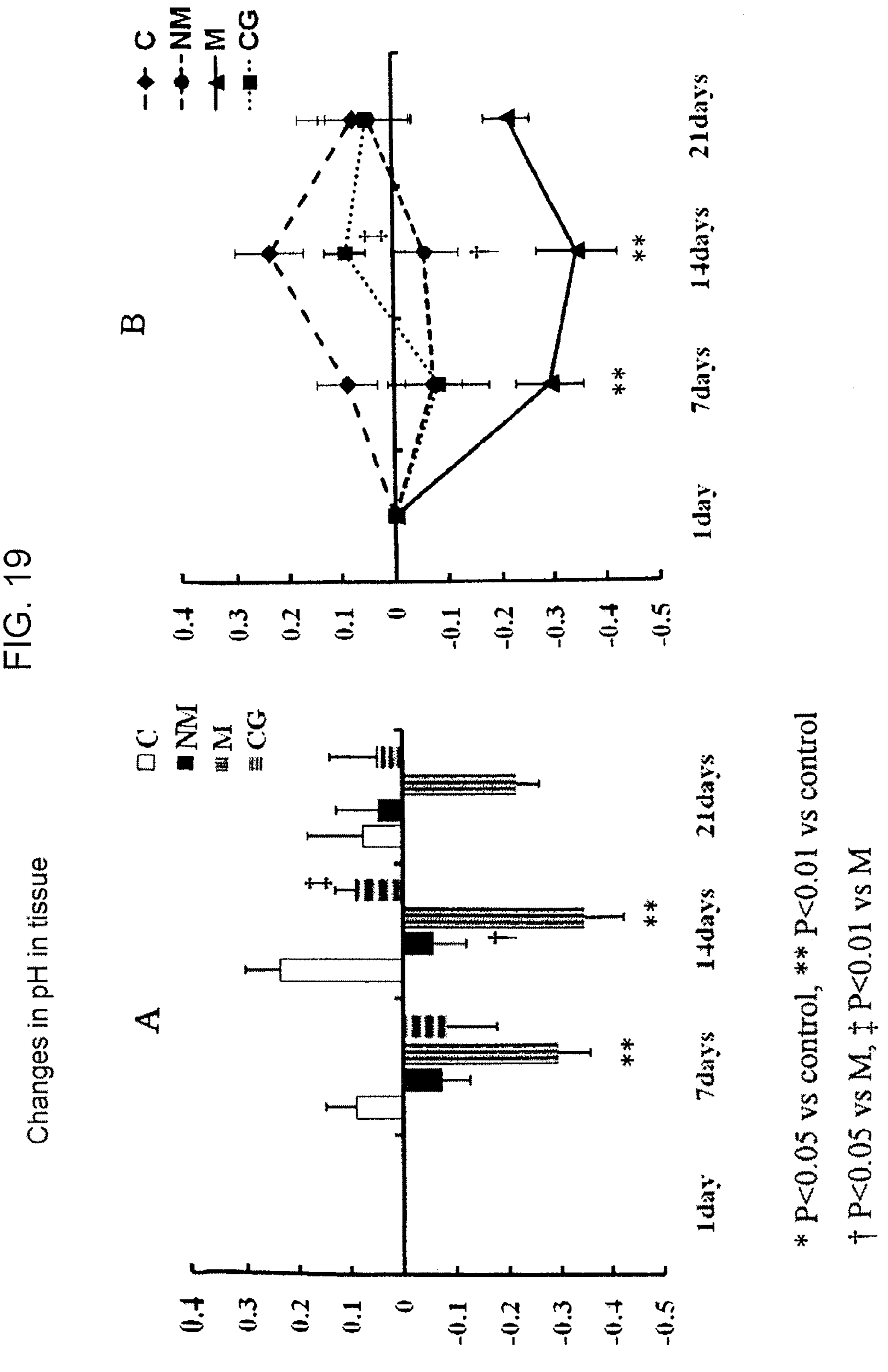
FIG. 19 Views showing the changes of average values of pH in the tissues of the individuals by progress of number of weeks after treatment.

(9) Comparison Among Four Groups of Measuring the Tissue pH (Table 5, FIG. 19)

The composition to be sealed under pressure into the carbon dioxide gas mist pressure bath means was experimented in the four kinds of the control (C), non-treated myocardial infarction (NM), $CO_2$ mist (M) and $CO_2$ gas. The number practiced by each of the gases is 8, 9, 8 and 5 individuals. In each of treatments, the pH changes of the individuals are measured in the pre-treatment (Δ1 day), one week after the treatment (Δ1 wks), two week after the treatment (Δ2 wks), and three week after the treatment (Δ3 wks).

TABLE 5

Basic Statistics: ⊿pH
Effects: Category ⊿pH * group
Exclusion of Line: pH new.svd

| | Number of Examples | Average Value | Standard Deviation | Standard Error |
|---|---|---|---|---|
| C, ⊿1 day | 8 | 0.000 | 0.000 | 0.000 |
| C, ⊿1 wks | 8 | .088 | .160 | .057 |
| C, ⊿2 wks | 8 | .234 | .183 | .065 |
| C, ⊿3 wks | 8 | .075 | .298 | .105 |
| CG, ⊿1 day | 5 | 0.000 | 0.000 | 0.000 |
| CG, ⊿1 wks | 5 | −.084 | .211 | .094 |
| CG, ⊿2 wks | 5 | .090 | .086 | .038 |
| CG, ⊿3 wks | 5 | .050 | .196 | .088 |
| CM, ⊿1 day | 8 | 0.000 | 0.000 | 0.000 |
| CM, ⊿1 wks | 8 | −.295 | .181 | .064 |
| CM, ⊿2 wks | 8 | −.347 | .215 | .076 |
| CM, ⊿3 wks | 8 | −.216 | .123 | .044 |
| V, ⊿1 day | 9 | 0.000 | 0.000 | 0.000 |
| V, ⊿1 wks | 9 | −.074 | .163 | .054 |
| V, ⊿2 wks | 9 | −.058 | .189 | .063 |
| V, ⊿3 wks | 9 | .046 | .238 | .079 |

To explain Table 5 concretely, the control (C) was experimented to 8 individuals, as to the values of pH of the respective individuals are measured 1 week (Δ1 wks) after the treatment, 2 weeks (Δ2 wks) after the treatment, and (Δ3 wks)

after the treatment. As to the changing values of pH of the respective individuals, making the reference values of the values when having calculated the average values of pH of 8 individuals measured before the treatment (Δ1 day), Table 5 expresses this reference value as "0.000".

Comparing the average values calculated from the changing values of the 8 individuals measured 1 week (Δ1 wks) after the treatment with the above mentioned reference value, this case shows that the average value increases in the changing values of pH of the 8 individuals, and shows it "0.088". 2 weeks (Δ2 wks) after the treatment, the average value further increases and shows it "0.234", but 3 weeks (Δ3 wks) after the treatment, the average value decreases and show "0.075".

Similarly, also as to three kinds of gases of the non treated myocardial infarction (NM), $CO_2$ mist and $CO_2$ gas (CG), making the reference values of the values when having calculated the average values of the changing values in pH before the treatment (Δ1 day), Table 5 expresses this reference value as "0.000". The average values of the changing values of pH in the respective individuals measured at 1 week (Δ1 wks) after the treatment, 2 weeks (Δ2 wks) after the treatment and (Δ3 wks) after the treatment are shown with the respective changing amounts from the respective reference values.

FIG. 19 shows Table 5 with the graphs of A part of the bar graph and B part of the bending line of interaction. The case of the control (C) does not show "acid" in the average values of the changing values of pH in the respective individuals till 1 week (Δ1 wks) after the treatment, 2 weeks (Δ2 wks) after the treatment and 3 weeks after the treatment, but the average value is above 0.000. In the case of the non-treated myocardial infarction (NM), acid is below 0.000 until 2 weeks (Δ2 wks) passes, and it is above 0.000 3 weeks (Δ3 wks) after the treatment.

On the other hand, as to $CO_2$ mist (M), the average values of pH in the respective individuals 1 week (Δ1 wks) after the treatment, 2 weeks (Δ2 wks) after the treatment and 3 weeks after the treatment are 0.000, and as seen therein pH of the tissue inclines to acid.

FIG. 19 shows that $CO_2$ mist (M) is large in the change of the pH value in comparison with the other gases, and pH of the tissue inclines toward "acid" through the period of 1 week (Δ1 wks) to (Δ3 wks) after the treatment.

Figure 20:
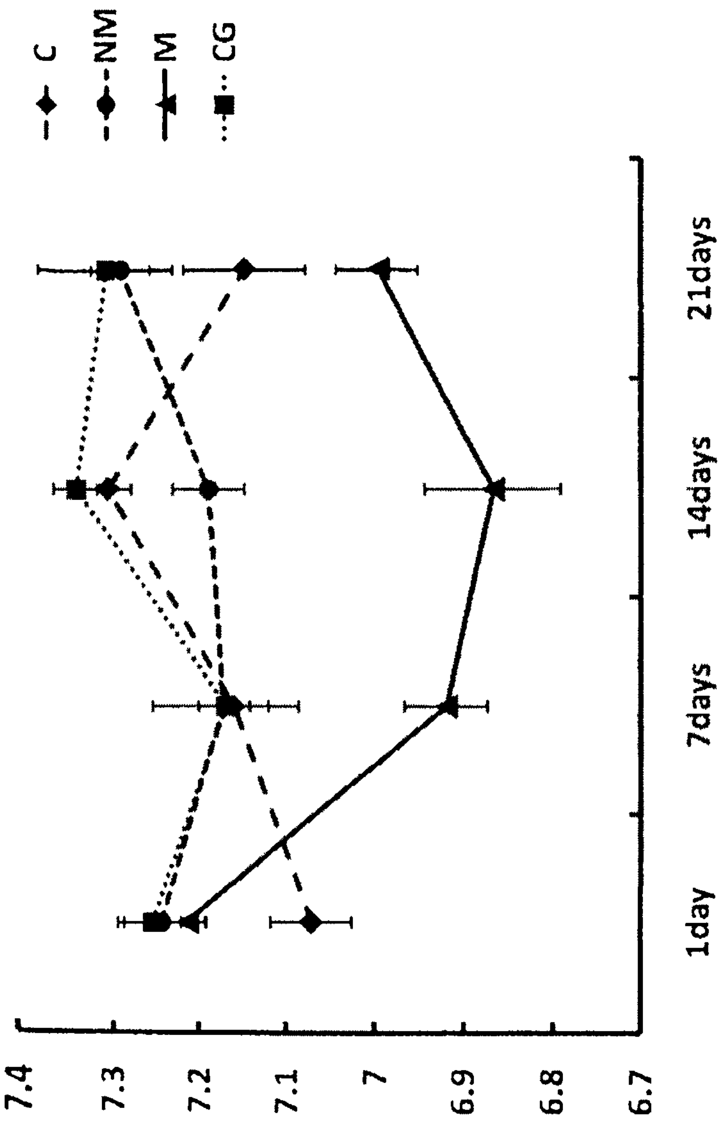
FIG. 20 A view showing the changes of average values of pH in the tissues of the individuals by progress of number of weeks after treatment.

(10) Measuring the Tissue pH (Table 6, FIG. 20)

TABLE 6

Basic Statistics: pH
Effects: Category pH * group
Exclusion of Line: pH new. svd

| | Number of Examples | Average Value | Standard Deviation | Standard Error |
|---|---|---|---|---|
| C, day 1 | 8 | 7.071 | .131 | .046 |
| C, 1 wks | 8 | 7.159 | .114 | .040 |
| C, 2 wks | 8 | 7.304 | .077 | .027 |
| C, 3 wks | 8 | 7.146 | .198 | .070 |
| CG, day 1 | 5 | 7.254 | .074 | .033 |
| CG, 1 wks | 5 | 7.168 | .189 | .084 |
| CG, 2 wks | 5 | 7.340 | .056 | .025 |
| CG, 3 wks | 5 | 7.306 | .170 | .076 |
| CM, day 1 | 8 | 7.214 | .064 | .023 |
| CM, 1 wks | 8 | 6.919 | .133 | .047 |
| CM, 2 wks | 8 | 6.866 | .217 | .077 |
| CM, 3 wks | 8 | 6.996 | .130 | .046 |
| V, day 1 | 9 | 7.243 | .153 | .051 |
| V, 1 wks | 9 | 7.170 | .087 | .029 |
| V, 2 wks | 9 | 7.188 | .127 | .042 |
| V, 3 wks | 9 | 7.289 | .101 | .034 |

Table 6 shows similarly to Table 5 that the gas compositions sealed under pressure into the carbon dioxide gas mist pressure bath means were experimented with the four kinds of the control (C), the non treated myocardial infarction (NM), $CO_2$ mist (M) and $CO_2$ gas (CG). The numbers of the individuals practiced with the gases are 8, 9, 8 and 5 pieces, respectively, providing that the average values of pH are shown as they are pre-treatment (day 1), 1 week (Δ1 wks) after the treatment, 2 weeks (Δ2 wks) after the treatment, and (Δ3 wks) after the treatment.

FIG. 20 is the banding line of interaction showing, in the pre-treatment (day 1), the higher pH value than those of the non-treated myocardial infarction (NM), $CO_2$ mist (M), $CO_2$ gas (CG) and the control (C). But, in the pH value of only $CO_2$ (M), the pH value decreases 2 weeks (Δ2 wks) after the treatment, and the other gases do not change. Concerning the changes of the respective gases, $CO_2$ mist (M) keeps the lower pH than those of the other gases, and as shown in FIG. 20, the changes are large, and for decreasing pH of the individuals, this gas is optimum for sealing under pressure into the carbon dioxide gas mist pressure bath means.

Figure 21:
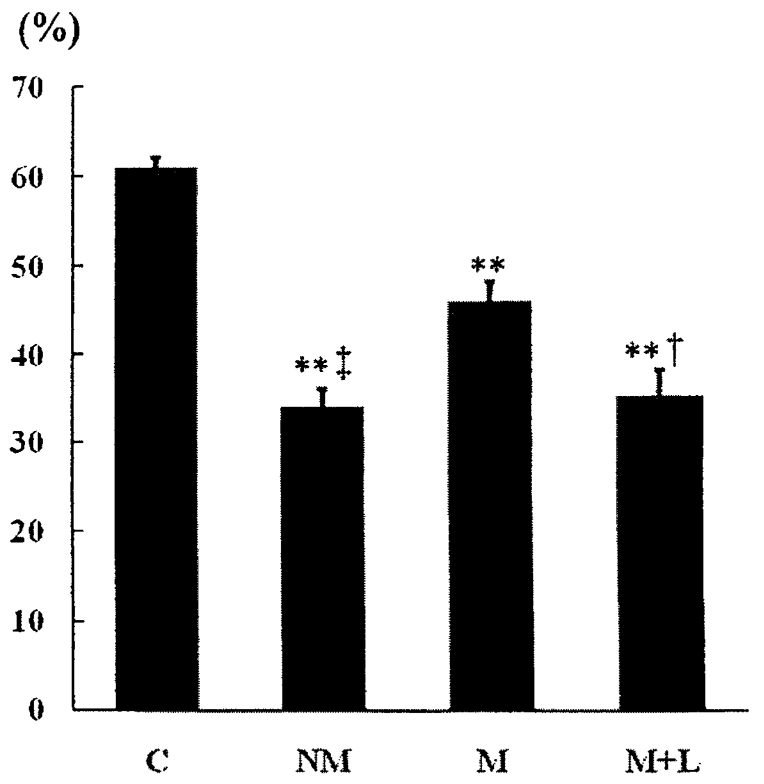
FIG. 21 A view showing the average values of the individual groups when measuring the ejection rates (EF) of the left ventricle of the heart.

(11) Ejection Rate (EF) of Left Ventricle of Heart (Table 7, FIG. 21)

TABLE 7

Basic Statistics: EF
Effects: group
Exclusion of Line: TTE 4W.2.svd

| | Number of Examples | Average Value | Standard Deviation | Standard Error |
|---|---|---|---|---|
| C | 14 | 60.922 | 3.313 | .886 |
| CM | 14 | 45.714 | 9.287 | 2.482 |
| L | 12 | 34.717 | 8.729 | 2.520 |
| V | 18 | 33.992 | 8.828 | 2.081 |

The male wistar rat aged of 8 weeks was intubated under the pentobarbital anesthesia, subjected to the thoracotomy, and ligated at the coronary left-front rami descendens to stop blood, and the myocardial infarction model was made, and Table 7 shows the average values prepared when measuring the ejection rate of left ventricle of the heart (EF) by the ultra sound cardiograph with respect to the 14 individual groups (C group) subjected to the apparent operations; the 14 individual groups (M group) of the carbon dioxide gas mist therapy; the $CO_2$ gas mist therapy+nitrogen monoxide (NO); the 12 individual groups (M+L group) of medication of enzymes for synthesis-inhibitor (L-NAME); and the non-cured 18 individual groups of ejection rate of left ventricle of heart (NM group). FIG. 21 shows the bar graph of Table 7. It is shown that the CM individual group is largely improved in EF than NM individual group.

The improving effect of EF receives restraint at the M+L group. From this fact, the participation of NO is suggested to the improving effect of the left ventricle contractile power by the carbon dioxide gas mist therapy.

Figure 22:
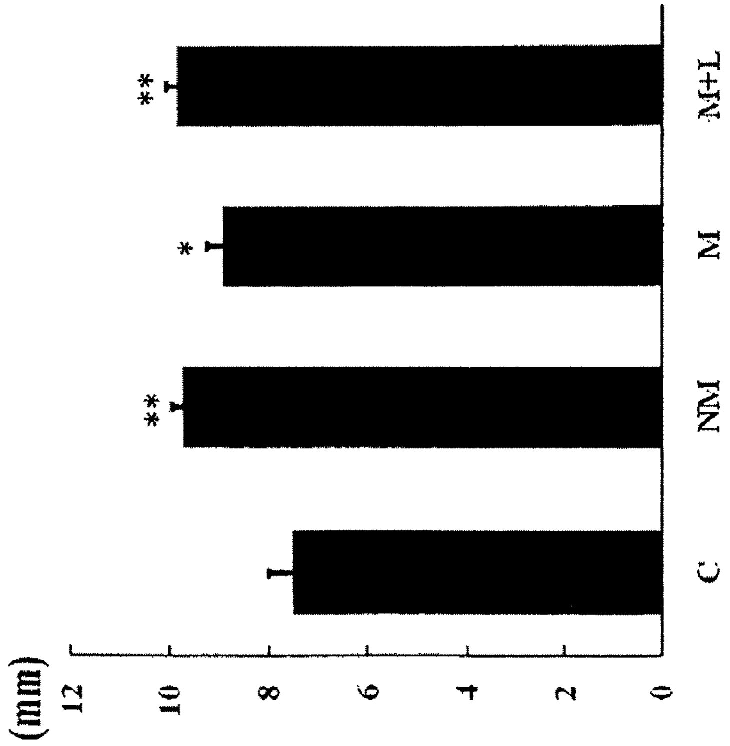
FIG. 22 A view showing the average values of individual groups when measuring the terminal diameters (LVDd) of expansion of the left ventricle of the heart.

(12) Terminal Diameter (LVDd) of Diastole of Left Ventricle of Heart (Table 8, FIG. 22)

TABLE 8

Basic Statistics: Dd
Effects: group
Exclusion of Line: TTE 4W.2.svd

| | Number of Examples | Average Value | Standard Deviation | Standard Error |
|---|---|---|---|---|
| C | 14 | 8.087 | .698 | .186 |
| CM | 14 | 9.279 | 1.186 | .317 |
| L | 12 | 10.036 | .738 | .213 |
| V | 19 | 9.842 | 1.094 | .251 |

With respect to the C group, M group, M+L group and NM group, Table 8 shows the average values of the individual groups when measuring the terminal diameters (LVDs) of diastole of left ventricle of the heart, and FIG. 22 shows them with the bar graph. The M individual group shows the lower value in comparison with the NM individual group, and the enlargement of the terminal diameters of diastole of left ventricle of the heart is restrained. That is, the heart re-modeling is restrained by the carbon dioxide gas mist therapy, and the effect by the carbon dioxide gas mist therapy is restrained by dosage of L-NAME, and the participation of NO is suggested.

Figure 23:
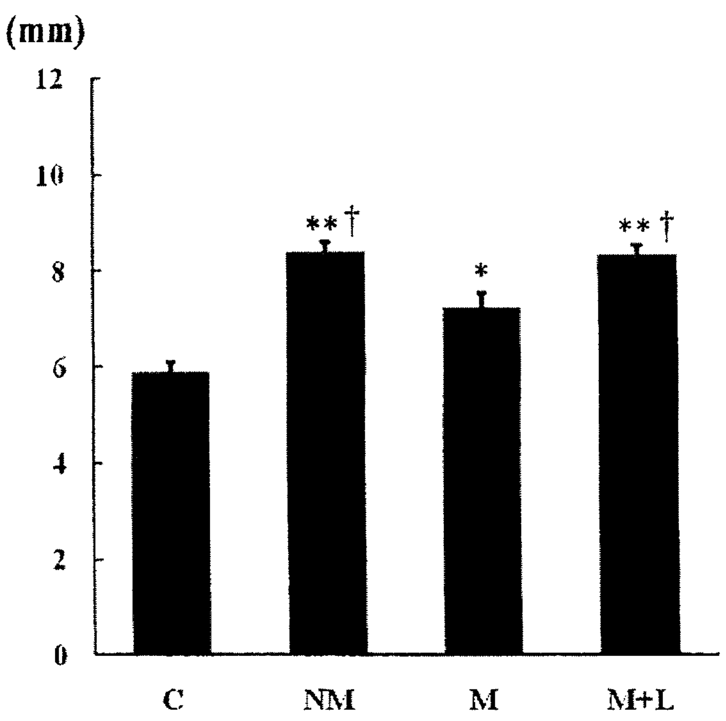
FIG. 23 A view showing average values of individual groups when measuring the terminal diameters (LVDs) of contraction of the left ventricle of the heart.

(13) Terminal Diameter (LVDs) of Contraction of Left Ventricle of Heart (Table 9, FIG. 23)

TABLE 9

Basic Statistics: Ds
Effects: group
Exclusion of Line: TTE 4W.2.svd

| | Number of Examples | Average Value | Standard Deviation | Standard Error |
|---|---|---|---|---|
| C | 14 | 5.934 | .502 | .134 |
| CM | 14 | 7.562 | 1.296 | .346 |
| L | 12 | 8.616 | 1.146 | .331 |
| V | 19 | 8.336 | 1.332 | .306 |

With respect to the C group, M group, M+L group and NM group, Table 9 shows the average values of the individual groups when measuring the terminal diameters (LVDs) of contraction of left ventricle of the heart, and FIG. 23 shows them with the bar graph. The M individual group shows that diastole of the terminal diameters of contraction of the left ventricle of the heart is restrained in comparison with the NM individual group. That is, the heart re-modeling is restrained by the carbon dioxide gas mist therapy, and the effect by the carbon dioxide gas mist therapy is restrained by dosage of L-NAME, and the participation of NO is suggested.

Figure 24:
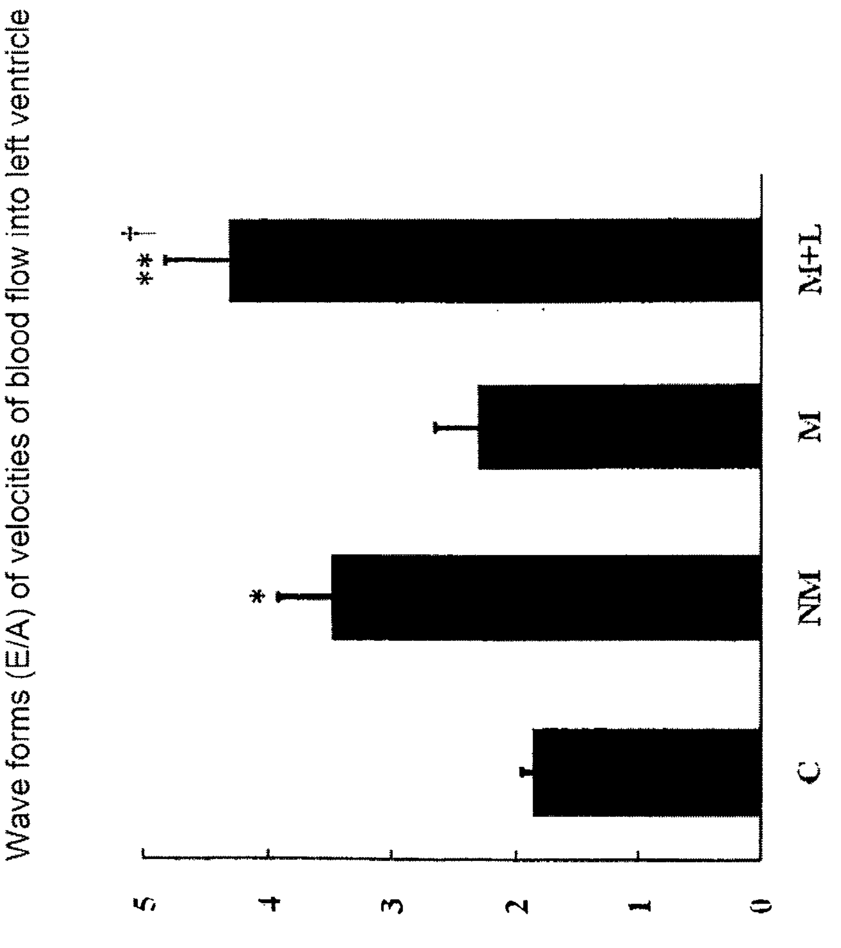
FIG. 24 A view showing the average values of the individual groups when calculating the wave forms (E/A) of velocities of blood flow into the left ventricle of the heart.

(14) Wave Forms (E/A) of Velocities of Blood Flow into Cardiac Left Ventricle (Table 10, FIG. 24)

TABLE 10

Basic Statistics: E/A
Effects: group
Exclusion of Line: TTE 4W.2.svd

| | Number of Examples | Average Value | Standard Deviation | Standard Error |
|---|---|---|---|---|
| C | 14 | 1.857 | .362 | .097 |
| CM | 14 | 2.301 | 1.283 | .343 |
| L | 12 | 4.301 | 1.789 | .516 |
| V | 18 | 3.477 | 1.833 | .432 |

With respect to the C, M, M+L and NM groups, the E and A waves were measured to calculate the ratios, and Table 10 shows the average values of the respective individual groups, and FIG. 24 shows them with the bar graph. In regard to the NM group, the M group recognizes the improvement of diastolic ability of the left ventricle, and its improving effect is restrained by dosage of L-NAME. That is, diastolic ability of the left ventricle is improved by the carbon dioxide gas mist therapy, while the improving effect of diastole of the left ventricle by the carbon dioxide gas mist therapy is restrained by dosage of L-NAME, and the participation of NO is suggested.

Figure 25:
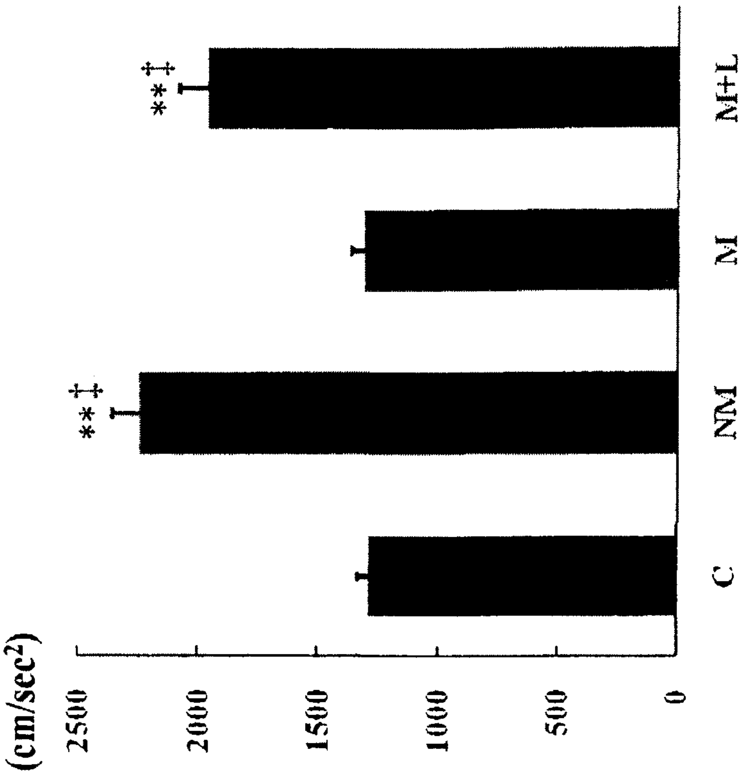
FIG. 25 A view showing the average values of the individual groups when calculating attenuation times of E waves.

(15) Attenuation Times of E Wave (Table 11, FIG. 25)

TABLE 11

Basic Statistics: Dct
Effects: group
Exclusion of Line: TTE 4W.2.svd

| | Number of Examples | Average Value | Standard Deviation | Standard Error |
|---|---|---|---|---|
| C | 14 | 1287.429 | 161.720 | 43.222 |
| CM | 14 | 1302.214 | 208.588 | 55.748 |
| L | 12 | 1955.000 | 398.850 | 115.138 |
| V | 18 | 2240.556 | 466.520 | 109.960 |

With respect to the C, M, M+L and NM groups, Dct was measured, and Table 11 shows the average values of the respective individual groups, and FIG. 25 shows them with the bar graph. In regard to the NM group, the M group recognizes the improvement of diastolic ability of the left ventricle, and its improving effect is restrained by dosage of L-NAME. That is, the diastolic ability of the left ventricle is improved by the carbon dioxide gas mist therapy, while the improving effect of diastole of the left ventricle by the carbon dioxide gas mist therapy is restrained by dosage of L-NAME, and the participation of NO is suggested.

Figure 26:
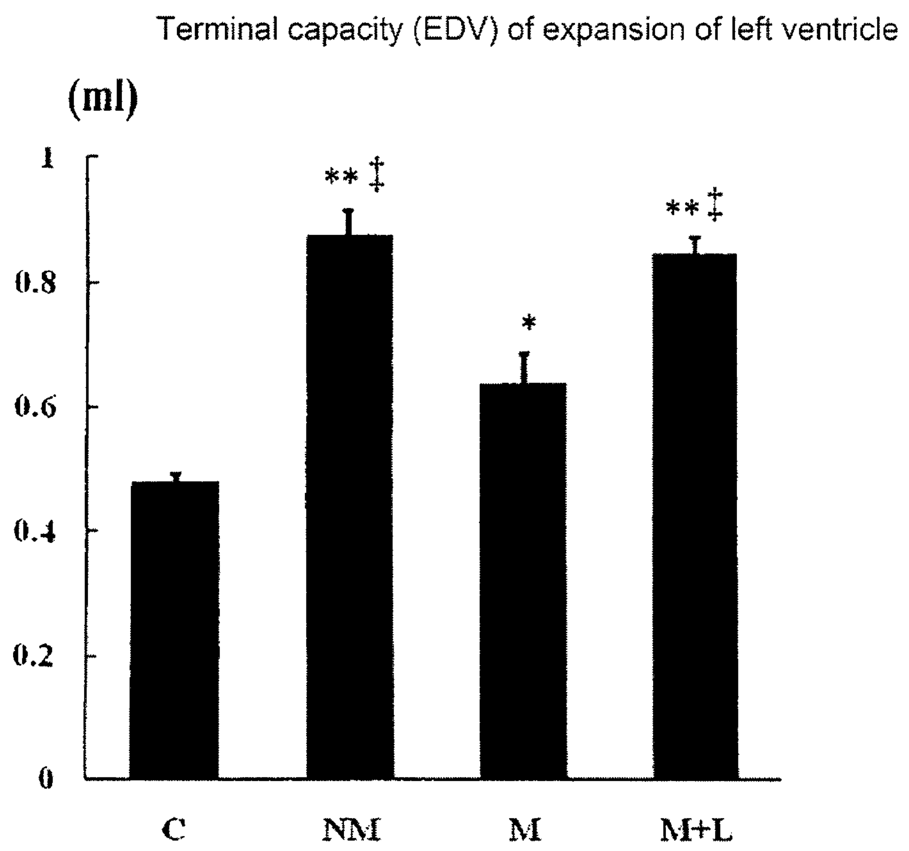
FIG. 26 A view showing the average values of the individual groups when calculating the terminal capacity (EDV) of expansion of the left ventricle of the heart.

(16) Terminal Capacity (EDV) of Expansion of Left Ventricle of Heart (Table 12, FIG. 26)

TABLE 12

Basic Statistics: EDV
Effects: group
Exclusion of Line: TTE 4W.2.svd

| | Number of Examples | Average Value | Standard Deviation | Standard Error |
|---|---|---|---|---|
| C | 14 | .480 | .042 | .011 |
| CM | 14 | .633 | .178 | .048 |
| L | 12 | .839 | .094 | .027 |
| V | 18 | .872 | .162 | .038 |

With respect to the C, M, M+L and NM groups, the terminal capacity (EDV) of expansion of the left ventricle was measured, and Table 12 shows the average values of the respective individual groups, and FIG. 26 shows the bar graph. In regard to the NM group, the M group recognizes the reduction of the terminal capacity of expansion of the left ventricle, and its reduction effect is restrained by dosage of L-NAME. That is, the heart re-modeling is restrained by the carbon dioxide gas mist therapy, while the effect of the carbon dioxide gas mist therapy is restrained by dosage of L-NAME, and the participation of NO is suggested.

Figure 27:
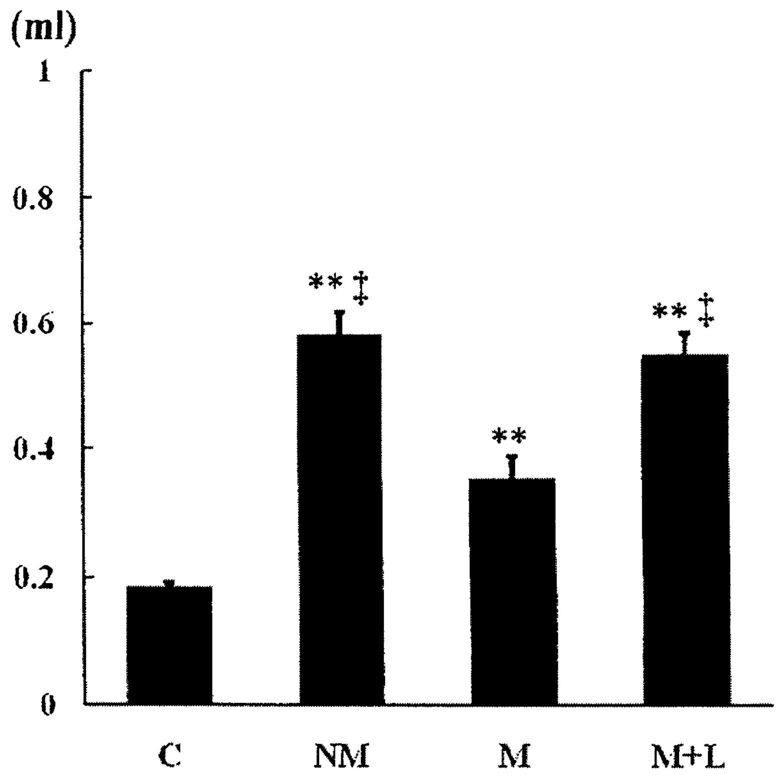
FIG. 27 A view showing the average values of the individual groups when calculating the terminal capacity (ESV) of contraction of the left ventricle of the heart.

(17) Terminal Capacity (ESV) of Contraction of Left Ventricle of Heart (Table 13, FIG. 27)

TABLE 13

Basic Statistics: ESV
Effects: group
Exclusion of Line: TTE 4W.2.svd

| | Number of Examples | Average Value | Standard Deviation | Standard Error |
|---|---|---|---|---|
| C | 14 | .187 | .019 | .005 |
| CM | 14 | .350 | .129 | .035 |
| L | 12 | .549 | .106 | .031 |
| V | 18 | .581 | .147 | .035 |

With respect to the C, M, M+L and NM groups, the terminal capacity (EDV) of contraction of left ventricle was measured, and Table 13 shows the average values of the respective individual groups, and FIG. 27 shows them with the bar graph. In regard to the NM group, the M group recognizes the reduction of the terminal capacity of contraction of the left ventricle, and its reduction effect is restrained by dosage of L-NAME. That is, the heart re-modeling is restrained by the carbon dioxide gas mist therapy, while the effect of the carbon dioxide gas mist therapy is restrained by dosage of L-NAME, and the participation of NO is suggested.

Figure 28:
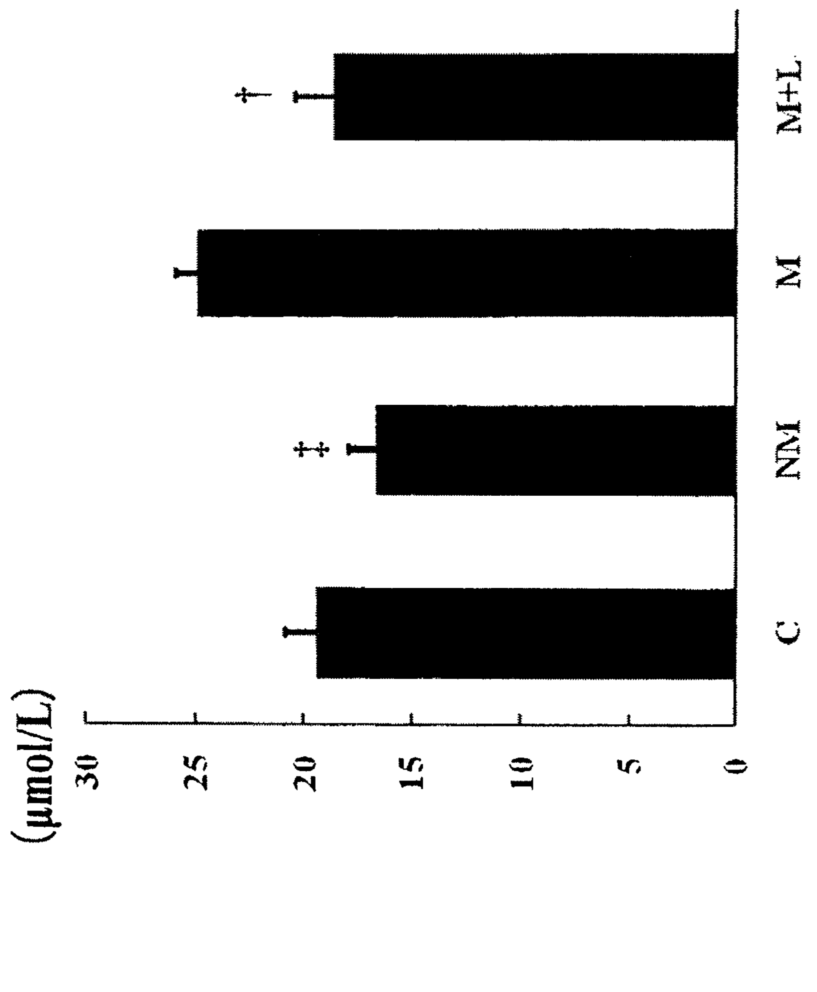
FIG. 28 A view showing the average values of the individual groups when calculating the nitrate ion ($NO_3^-$) of blood serum.

(18) Nitrate Ion ($NO_3^-$) of Blood Serum (Table 14, FIG. 28)

TABLE 14

Basic Statistics: $NO_3^-$
Effects: group
Exclusion of Line: Blood-Collecting Item 2.svd

| | Number of Examples | Average Value | Standard Deviation | Standard Error |
|---|---|---|---|---|
| C | 14 | 19.429 | 5.774 | 1.543 |
| CM | 16 | 24.750 | 3.890 | .973 |
| L | 12 | 18.500 | 6.098 | 1.760 |
| V | 18 | 16.556 | 4.731 | 1.115 |

With respect to the C, M, M+L and NM groups, blood-gathering was performed, and Table 14 shows the average values of the respective individual groups when measuring the nitrate ion of blood serum ($NO_3^-$), and FIG. 28 shows them with the bar graph. The highest nitrate ion of blood serum in the M individual group was detected, and the increase of nitrate ion of blood serum is restrained by dosage of L-NAME. The blood serum ($NO_3^-$) is determined to be an essence of an endothelial cell derived relaxation factor (EDRF) in blood, and it is a comparatively stable oxide metabolic product derived from NO. Its value increased significantly by the carbon dioxide gas mist therapy. Its increase was restrained by L-NAME. That is, the NO production effect exists owing to the carbon dioxide gas mist therapy, and the carbon dioxide gas mist therapy is restrained by the L-NAME dosage.

Figure 29:
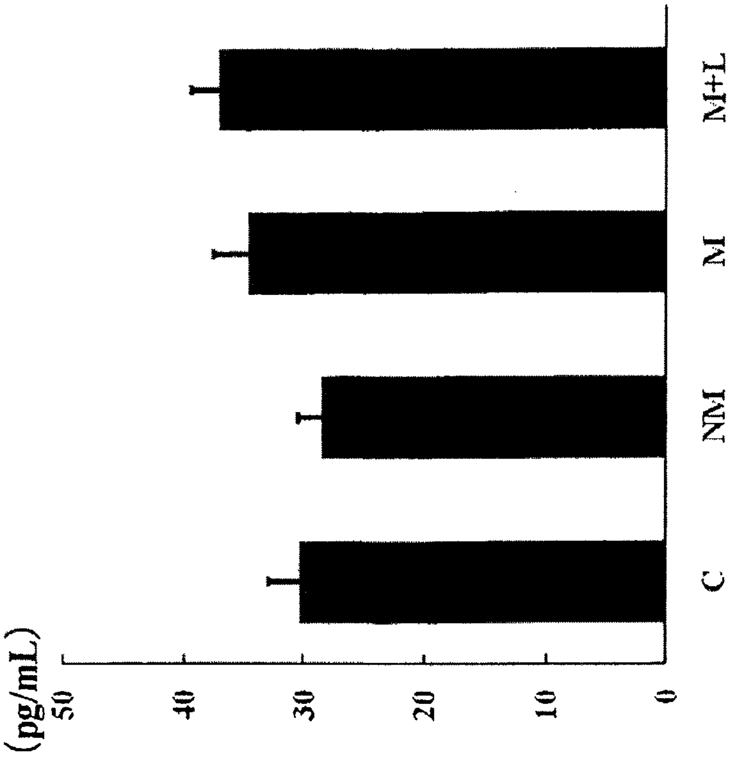
FIG. 29 A view showing the average values of the individual groups when calculating the skin growth factors (VEGF) in vessel of blood serum.

(19) Skin Growth Factor (VEGF) in Vessel of Blood Serum (Table 15, FIG. 29)

TABLE 15

Basic Statistics: VEGF
Effects: group
Exclusion of Line: Blood-Collecting Item 2.svd

| | Number of Examples | Average Value | Standard Deviation | Standard Error |
|---|---|---|---|---|
| C | 14 | 30.279 | 9.605 | 2.567 |
| CM | 16 | 34.456 | 11.586 | 2.896 |
| L | 12 | 36.975 | 7.955 | 2.297 |
| V | 18 | 28.411 | 8.649 | 2.039 |

With respect to the C, M, M+L and NM groups, Table 15 shows the average values of the respective individual groups when measuring the skin growth factors (VEGF) in vessel of blood serum, and FIG. 29 shows them with the bar graph. No difference was recognized among the respective groups of the skin growth factors in vessel of blood serum.

Figure 30:
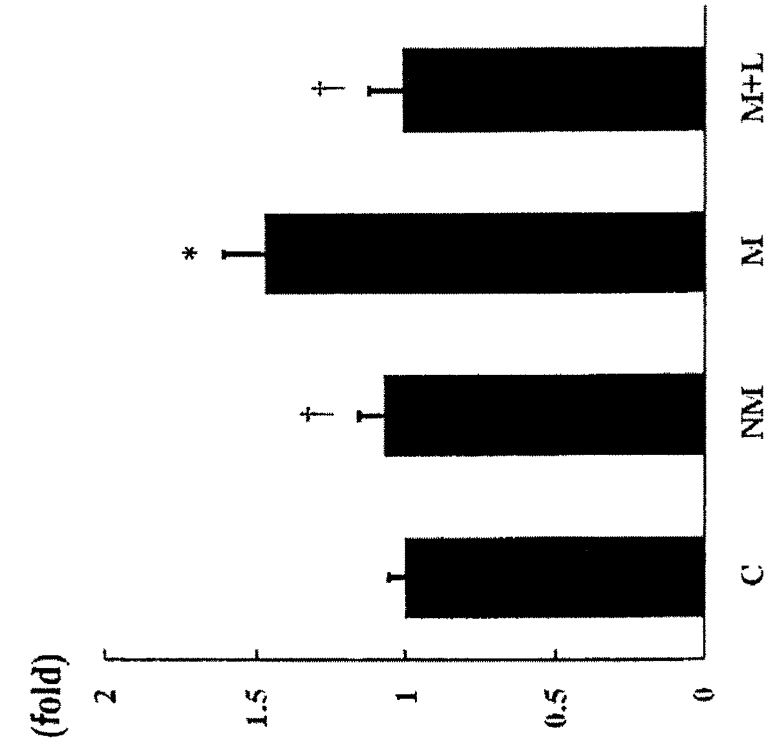
FIG. 30 A view showing the average values of the individual groups when calculating the skin growth factors (VEGF) in blood vessel of myocardium.

(20) Skin Growth Factor (VEGF) in Vessel of Myocardium (Table 16, FIG. 30)

TABLE 16

Basic Statistics: VEGF
Effects: group

| | Number of Examples | Average Value | Standard Deviation | Standard Error |
|---|---|---|---|---|
| C | 13 | 1.000 | .195 | .054 |
| CM | 14 | 1.465 | .518 | .139 |
| L | 12 | 1.005 | .370 | .107 |
| V | 19 | 1.070 | .343 | .079 |

With respect to the C, M, M+L and NM groups, Table 16 shows the average values of the respective individual groups when measuring the skin growth factors (VEGF) in vessel of myocardium, and FIG. 30 shows the bar graph. In regard to MN group, myocardium VEGF significantly recognized the manifesting increase in the M group, and the manifesting increase was restrained by the dosage of L-NAME. That is, by carbon dioxide gas mist therapy, the new formation of blood tube was accelerated, and by the dosage of L-NAME, the effect of carbon dioxide gas mist therapy was restrained.

(21) Sizes of Myocardial Infarction

TABLE 17

Basic Statistics: MI size
Effects: group
Exclusion of Line: MI size. svd

| | Number of Examples | Average Value | Standard Deviation | Standard Error |
|---|---|---|---|---|
| CM | 7 | 31.429 | 11.443 | 4.325 |
| L | 9 | 32.778 | 7.546 | 2.515 |
| V | 9 | 34.444 | 9.167 | 3.056 |

Figure 31:
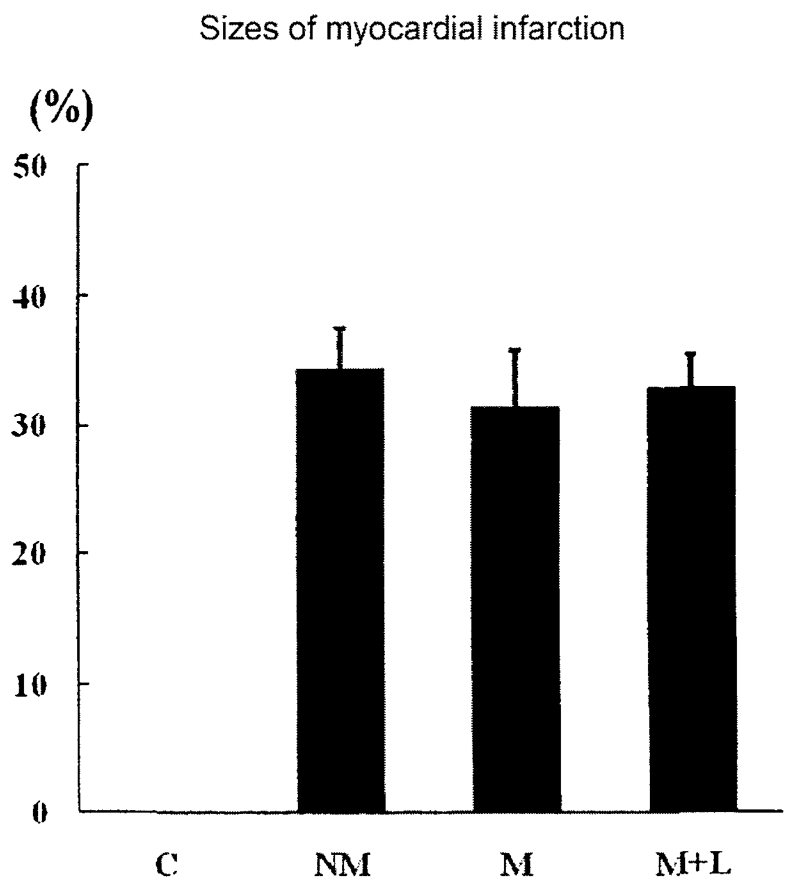
FIG. 31 A view showing average values of individual groups when calculating sizes of myocardial infarction.

With respect to the M, M+L and NM groups, Table 17 shows the average values of the respective individual groups when measuring the sizes of myocardial infarction, and FIG. 31 shows them with the bar graph. Among the three groups, no significant difference was recognized in the sizes of myocardial infarction. This fact proves that the size of myocardial infarction is constant in each of the groups, and that the models of myocardial infarction depending on the present study are constant. The improving effect in the cardiac function does not depend on the difference of the model size of myocardial infarction, but depends on the effect of the carbon dioxide gas mist.

Figure 32:
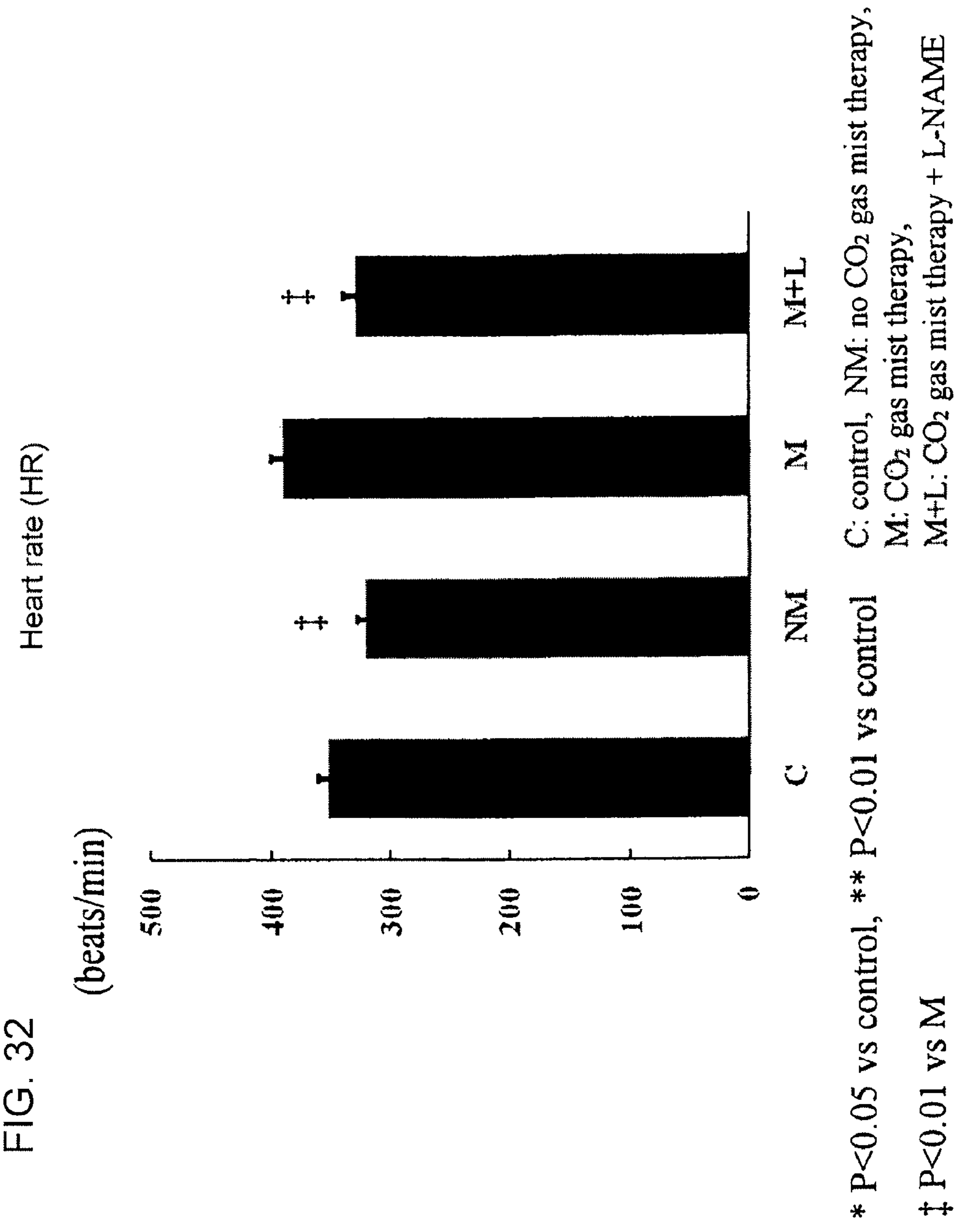
FIG. 32 A view showing average values of individual groups when measuring heart rates.

(22) Heart Rate (HR) (Table 18, FIG. 32)

Basic Statistics: HR
Effects: group
Exclusion of Line: Hemodynamics, weight.svd

| | Number of Examples | Average Value | Standard Deviation | Standard Error |
|---|---|---|---|---|
| C | 14 | 352.321 | 34.224 | 9.147 |
| CM | 14 | 388.571 | 35.800 | 9.568 |
| L | 12 | 327.800 | 33.866 | 9.776 |
| V | 19 | 321.458 | 31.670 | 7.266 |

With respect to the C, M, M+L and NM groups, Table 18 shows the average values of the respective individual groups when measuring the heart rates, and FIG. 32 shows them with the bar graph. Comparing with the C group, the heart rates lower in the M+L and NM groups, but lowering in the M group is not recognized.

Figure 33:
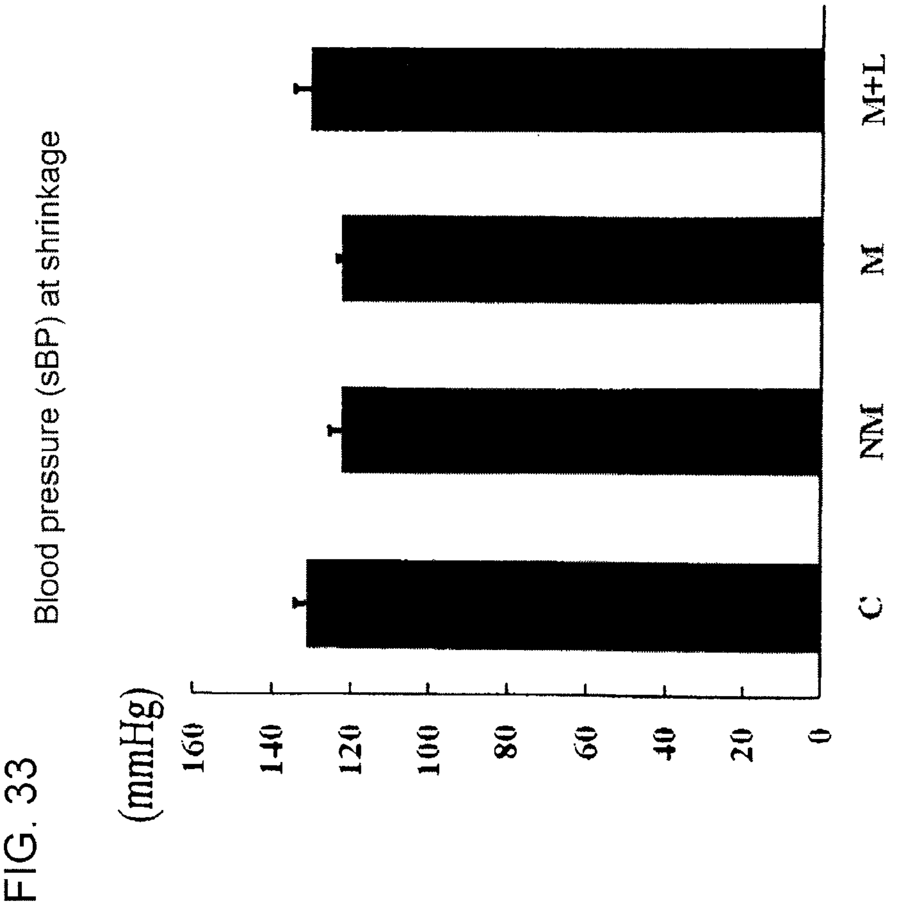
FIG. 33 A view showing average values of individual groups when measuring blood pressure when shrinking.

(23) Blood Pressure at Shrinkage (sBP) (Table 19, FIG. 33)

TABLE 19

Basic Statistics: sBP
Effects: group
Exclusion of Line: Hemodynamics, weight.svd

| | Number of Examples | Average Value | Standard Deviation | Standard Error |
|---|---|---|---|---|
| C | 14 | 131.021 | 9.949 | 2.659 |
| CM | 14 | 122.086 | 5.604 | 1.498 |
| L | 12 | 129.692 | 14.453 | 4.172 |
| V | 19 | 121.974 | 11.063 | 2.538 |

With respect to the C, M, M+L and NM groups, Table 19 shows the average values of the respective individual groups when measuring blood pressure at shrinkage, and FIG. 33 shows them with the bar graph. Among the respective groups, no difference was recognized. That is, the carbon dioxide gas mist therapy gave no influence to blood pressure at shrinkage.

Figure 34:
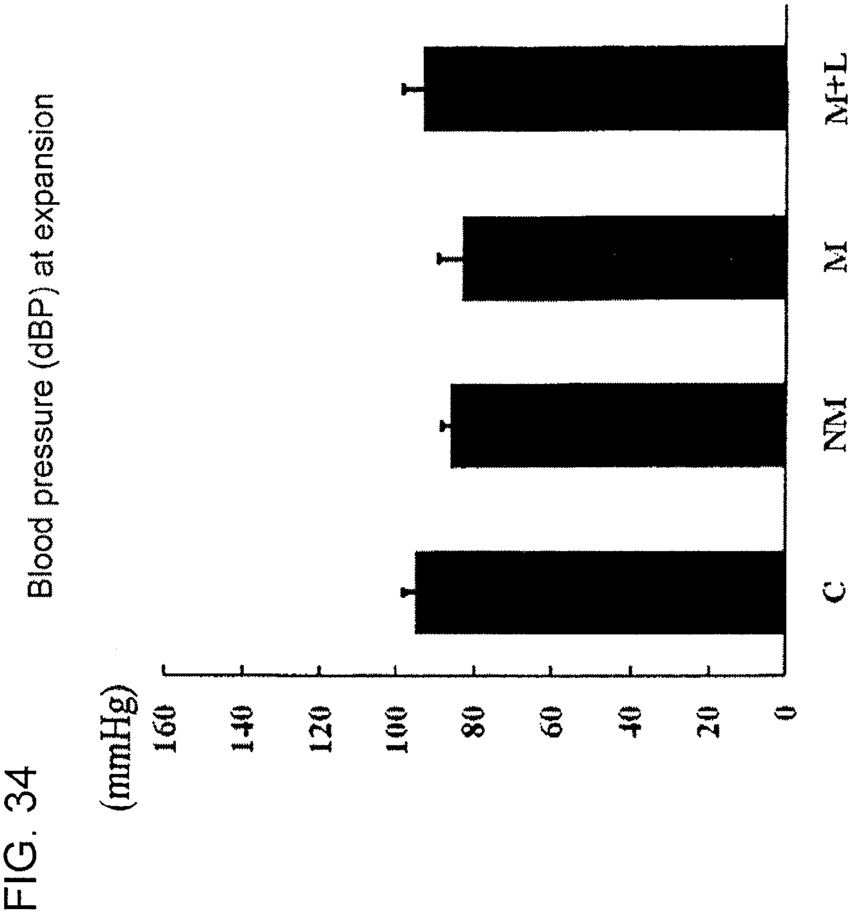
FIG. 34 A view showing average values of individual groups when measuring blood pressure when expanding.

(24) Blood Pressure at Expansion (dBP) (Table 20, FIG. 34)

TABLE 20

Basic Statistics: dBP
Effects: group
Exclusion of Line: Hemodynamics, weight.svd

| | Number of Examples | Average Value | Standard Deviation | Standard Error |
|---|---|---|---|---|
| C | 14 | 94.786 | 11.834 | 3.163 |
| CM | 14 | 83.214 | 9.677 | 2.586 |
| L | 11 | 93.136 | 15.552 | 4.689 |
| V | 19 | 85.611 | 10.545 | 2.419 |

With respect to the C, M, M+L and NM groups, Table 20 shows the average values of the respective individual groups when measuring blood pressure at expansion, and FIG. 34 shows them with the bar graph. Among the respective groups, no difference is recognized in blood pressure at expansion. That is, the carbon dioxide gas mist therapy gives no influence to blood pressure at expansion.

Figure 35:
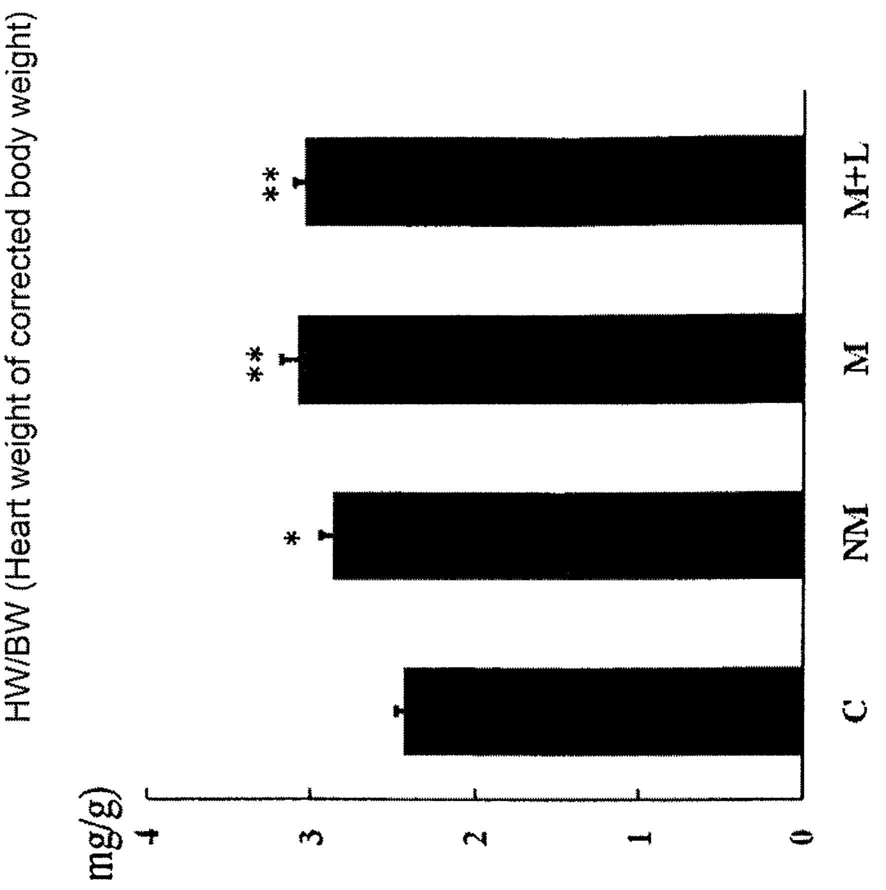
FIG. 35 A view showing average values of individual groups when measuring the heart weight of a corrected body weight.

(25) HW/BW (Weight of Heart of Corrected Body Weight) (Table 21, FIG. 35)

TABLE 21

Basic Statistics: HW/BW*1000
Effects: group
Exclusion of Line: Hemodynamics, weight.svd

| | Number of Examples | Average Value | Standard Deviation | Standard Error |
|---|---|---|---|---|
| C | 14 | 2.442 | .159 | .042 |
| CM | 14 | 3.079 | .355 | .095 |
| L | 12 | 3.032 | .214 | .062 |
| V | 19 | 2.865 | .317 | .073 |

With respect to the C, M, M+L and NM groups, Table 21 shows the average values of the respective individual groups when measuring weight of the heart of the corrected body weight, and FIG. 35 shows them with the bar graph. Comparing with the C group, increase of weight of the heart is recognized, but no significant difference is recognized among the 3 groups being the myocardial infarction.

The high absorption effect of carbon dioxide by the carbon dioxide gas mist pressure bath treatment depending on the present invention is proved with the various results through the animal tests. In the following, explanation will be made to the experiments, referring to Tables and the graphs.

At the outset, almost all (abundance ratio 98.93%) of carbon existing on the earth is 12 ($^{12}C$) in the atomic weight, but carbon ($^{13}C$) of the atomic weight 13 as the stable isotope exists 1.07%. The stable isotope $^{13}C$ has no radioactivity and is a half-permanently stable isotope. $CO_2$ existing in the living body is also almost $^{12}CO_2$ similarly in atmospheric air.

Then, artificially produced $^{13}CO_2$ of high concentration (99%) was caused to carry out dermal desperation in rats having myocardial infarction with the carbon dioxide gas mist pressure bath apparatus of this invention, and quantitative analyses were performed on $^{12}CO_2$ derived from respiration of an isotope of two kinds of carbon dioxide $CO_2$ as well as on $^{13}CO_2$ derived from dermal respiration, so that it could be proved whether or not dermal respiration was made effectively. In this way, the experiments were divided into the group treated with the $^{13}CO_2$ mist depending on the carbon dioxide gas mist pressure bath apparatus of this invention and the non-treated group, and the experiments analyzed a distribution of $^{13}CO_2$ absorbed from the skin into an internal organ.

The analyses used the specimens of 16 pieces in total of the frozen tissues of plasmas, hearts, livers and muscles of the two kinds of rats No. 1 and No. 2 which had not been subjected to the carbon dioxide gas mist pressure bath treatment by $^{13}CO_2$ (called as "non-treated No. 1" and "non-treated No. 2" hereafter) as well as the specimens of plasmas, hearts, livers and muscles of the two kinds of rats No. 1 and No. 2 which had been subjected to the carbon dioxide gas mist pressure bath treatment by $^{13}CO_2$ (called as "$^{13}CO_2$ mist treated No. 1" and "$^{13}CO_2$ mist treated No. 2" hereafter), and the analyses detected carbonic acids ($^{12}CO_2$ and $^{13}CO_2$) from the 16 specimens. In the following, explanation will be made to the procedures and results of the analyses and tests in order.

(1) Analyzing and Testing Ways (1.1) Setting of Measuring Conditions (1.1.1) Preparation of Standard Solution Sodium carbonate was dissolved in water to prepare a solution of an arbitrary concentration, and its fixed amount was collected in a measuring vial, added with sulfuric acid and sealed. Amounts of carbonic acid in the measuring vial were 5 levels of 10, 50, 100, 250 and 500 μg, and their controls were performed in the glove box of in a nitrogen gas atmosphere.

(1.1.2) Measure

The gas phase of the measuring vial was measured by a gas chromatogram mass analysis under the following conditions.

<Measuring Condition>

Column: Pora BOND Q length 25 m·inner diameter 25 mm·film thickness 3 μmm

Column temperature: 40° C. (8 minutes)

Carrier gas: He

Sample injection: Head space (60° C., 1 minute heating)

Ionization: Electron ionization (EI method: 70 eV)

Measuring mode: Selection ion monitoring (SIM)

Monitor ion: Quantitative ion m/z44 ($^{12}CO_2$), m/z45 $^{13}CO_2$ (1.1.3) Preparation of Analytical Curve The standard solution was measured, the concentration (μg/vial) was plotted on the vertical axis, the peak area of $CO_2$ detected from the chromatograph of the extracted ion current (EIC) of m/z44 was plotted on the lateral axis, and the analytical curve was prepared.

(1.2) Analyses of Rat Tissue (1.2.1) Pre-Treatment

The aqueous sodium hydroxide solution was added to the sample, defrosted and uniformed in a mortar, and its determined amount was collected in the measuring vial into which sulfuric acid was added and sealed. These operations were performed in a glove box under nitrogen gas atmosphere. The operation after making uniform in the mortar was repeated one to three times per one sample.

(1.2.2) Calculation of Analyzed Values

After measuring the samples in the measuring vial after the pre-treatment, $CO_2$ of measured m/z44 and m/z45 was determined with the $CO_2$ analytical curve of m/z44. The detected amount of $CO_2$ was divided by the sample amount, and the amounts of $^{12}CO_2$ and $^{13}CO_2$ per sample mass were found.

Further, for correcting effects of the natural isotope (m/z45) existing in $CO_2$ derived from respiration, the amount of $^{13}CO_2$ found from the amount of $^{12}CO_2$ was deducted from the detected amount of $^{13}CO_2$ and the amount of $^{13}CO_2$ derived from the dermal respiration was calculated.

Figure 39:
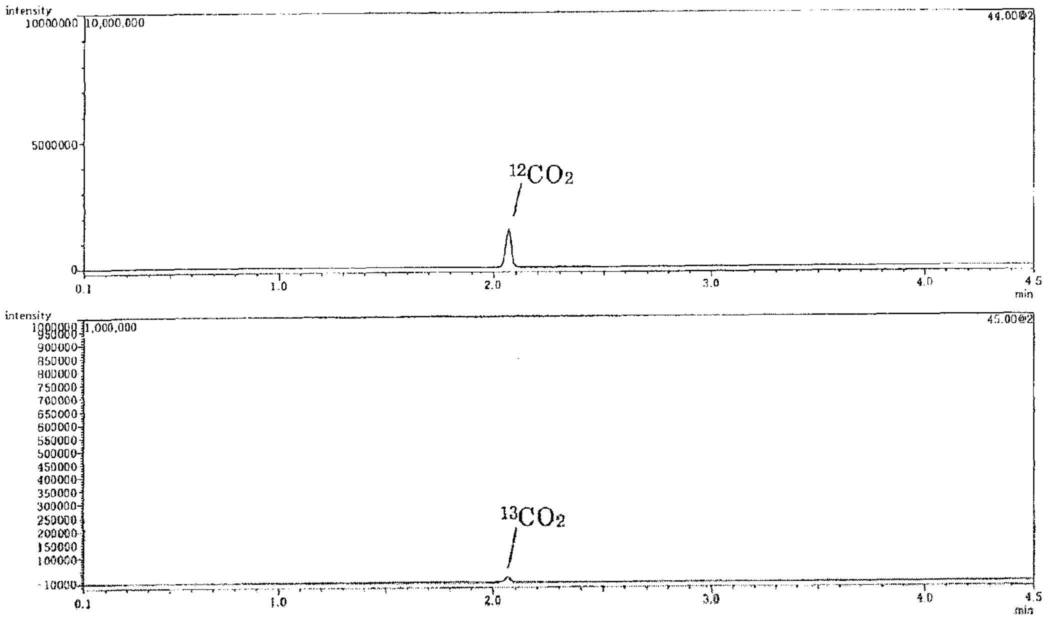
FIG. 39 Views showing the measured results by EIC chromatographs of $^{12}CO_2$ and $^{13}CO_2$ of standard carbonic acid solution.
Figure 40:
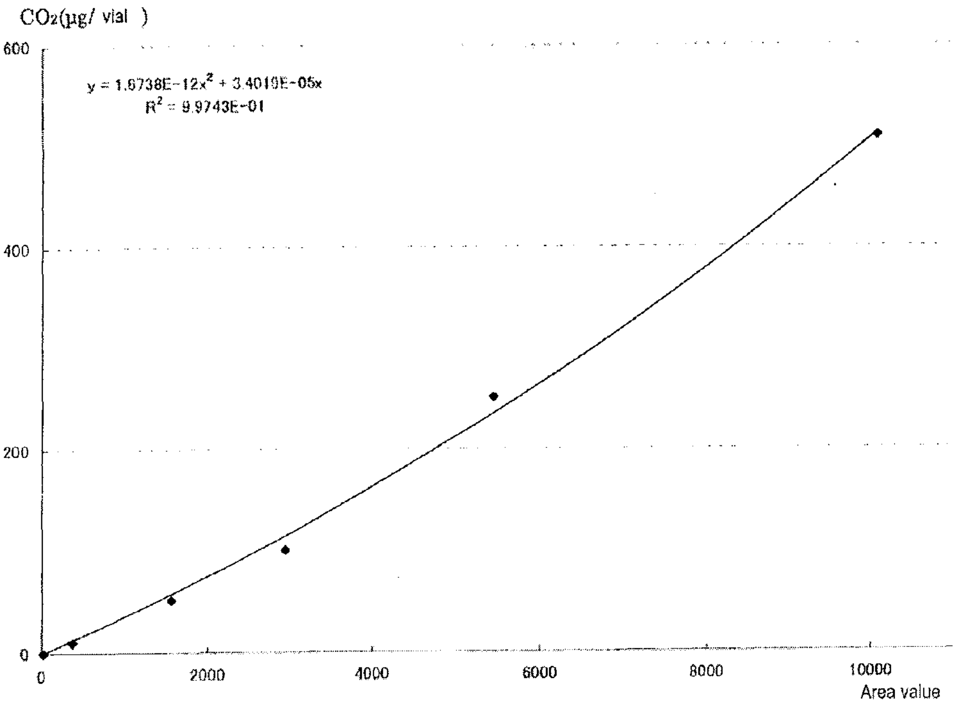
FIG. 40 A view showing the analytical curve of $^{12}CO_2$ prepared on the basis of measured results by EIC chromatograph of standard carbonic acid solution.

(2) Analyses and Test Results (2.1) Validity of Measuring Conditions (2.1.1) Linearity of Analytical Curve FIG. 39 is the measured EIC chromatogram where the upper is the volume of $^{12}CO_2$ and the lower is the volume of $^{13}CO_2$. The chromatogram shows the holding time on the lateral axis and the concentration on the vertical axis, and the area (peak area) of a triangular part of a normal distribution is the measured volume of $^{12}CO_2$. FIG. 40 shows the analytical curve of a prepared $^{12}CO_2$, where the coefficient (R) of correlation is a quadratic curve being a straight line approximate as 0.9987.

(2.1.2) Reproducibility of Repeated Measures

As a result of repeating measurements of standard solution of carbonic acid being 500 μg, reproducibility within day was 3 to 5% of the relative standard deviation (RSD), and reproducibility within a period (10 days) of measuring the specimens was 11% of RSD.

As a result of repeating the specimens uniformed in the mortar from the pre-treatment of sampling into the measuring vial to measuring, RSD showed the high reproducibility of less than 20% in all the specimens. By the way, while RSD of the standard solution was 3 to 5%, RSD of the specimens was less than 20%, and the causes therefor may be considered as shortage of uniforming the specimens or time lag per adding or sealing reagents, but such causes are considered no problem as a reproducibility level.

(2.2) Results of Analyzing Issues of Rats

FIGS. 41 to 56 show the measured results by the EIC chromatograph in each sample of 16 pieces. In each of them, the upper is the chromatograph of $^{12}CO_2$ and the lower is the chromatograph of $^{13}CO_2$.

The volumes of $CO_2$ were measured in the peak area of each chromatographs, showing the lateral axis was the holding times and the vertical axis was the concentrations, and the values of $CO_2$ of the measured m/z44 (the upper) and m/z45 (the lower) were determined by the analytical curves.

Table 22 shows the determined results of $^{12}CO_2$ and $^{13}CO_2$ of each of the samples.

TABLE 22

Unit: μg/g

| Processing | Samples | Plasma $^{12}CO_2$ | Plasma $^{13}CO_2$ | Heart $^{12}CO_2$ | Heart $^{13}CO_2$ | Liver $^{12}CO_2$ | Liver $^{13}CO_2$ | Muscle $^{12}CO_2$ | Muscle $^{13}CO_2$ |
|---|---|---|---|---|---|---|---|---|---|
| Non-Processing | No. 1 | 860 | 7.6 | 290 | 3.3 | 450 | 4.7 | 150 | <2.5 |
| | No. 2 | 960 | 8.4 | 270 | 3.1 | 280 | 3.1 | 320 | 3.5 |
| $^{13}CO_2$ | No. 1 | 960 | 59 | 660 | 29 | 710 | 29 | 210 | 8.9 |
| Mist-Treating | No. 2 | 1300 | 70 | 600 | 23 | 550 | 20 | 330 | 12 |
| Minimum Limit of Determination | | 50 | 2.5 | 50 | 2.5 | 50 | 2.5 | 50 | 2.5 |

Figure 41:
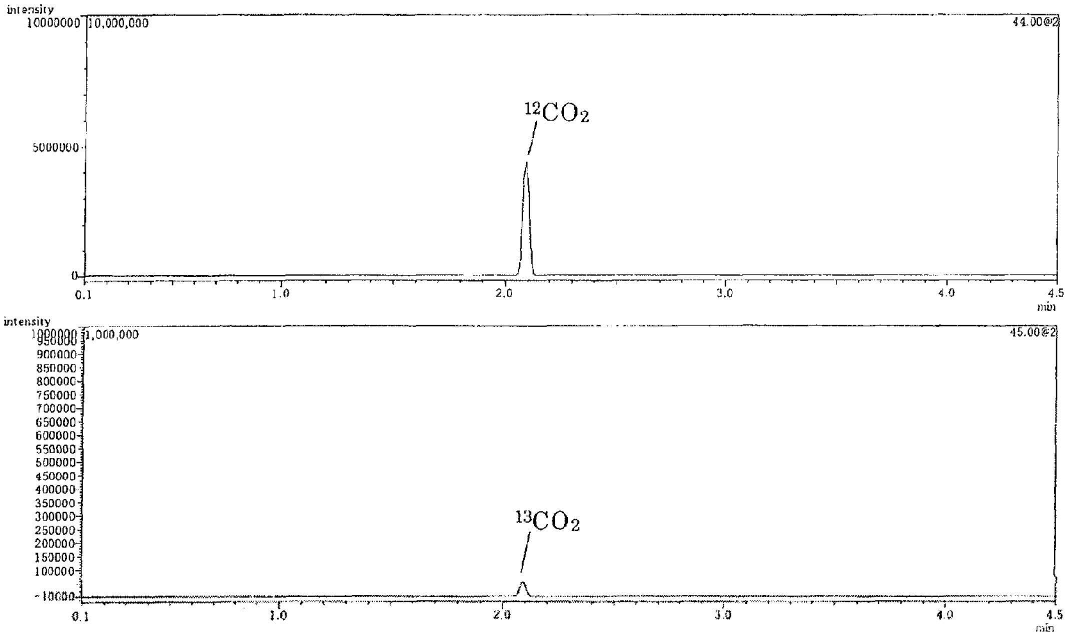
FIG. 41 Views showing the measured results by EIC chromatograph of $^{12}CO_2$ and $^{13}CO_2$ in the plasma of non-treated No. 1 rats.
Figure 42:
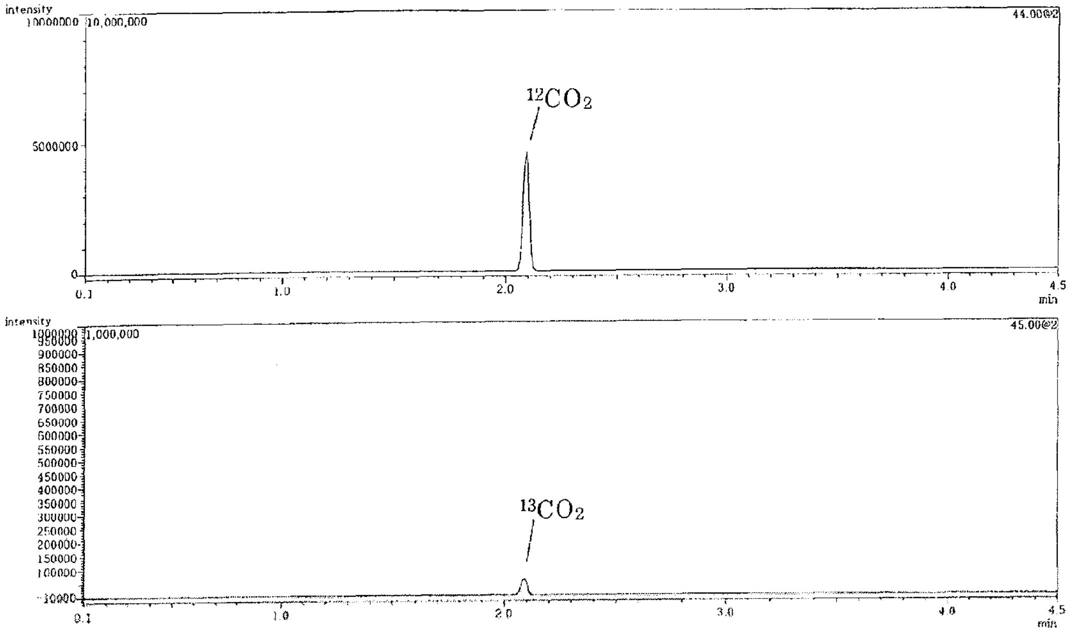
FIG. 42 Views showing the measured results by EIC chromatograph of $^{12}CO_2$ and $^{13}CO_2$ in the plasma of non-treated No. 4 rats.

For example, the chromatograph of FIG. 41 shows the volume of $^{12}CO_2$ in the plasma of the non-treated No. 1 on the upper stage and the volume of $^{13}CO_2$ in the plasma on the lower stage, and these determined results are divided (÷) by the volume of the plasma. Table 22 shows that the volume of $^{12}CO_2$ per mass of the found plasma is 860 μg/g and the volume of $^{13}CO_2$ is 7.6 μg/g.

Figure 43:
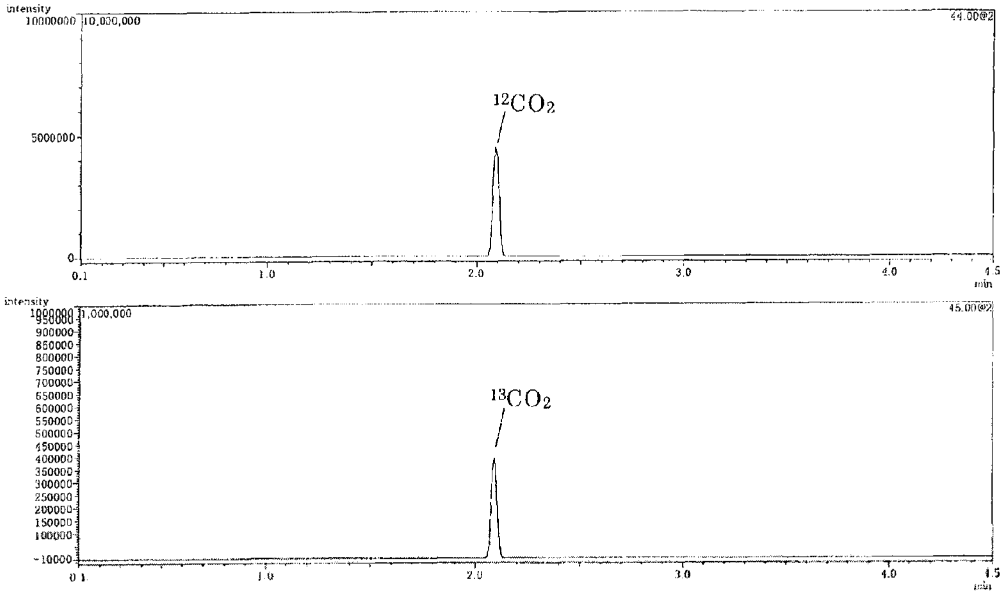
FIG. 43 Views showing the measured results by EIC chromatograph of $^{12}CO_2$ and $^{13}CO_2$ in the plasma of No. 1 rats treated with $^{13}CO_2$ mist.
Figure 44:
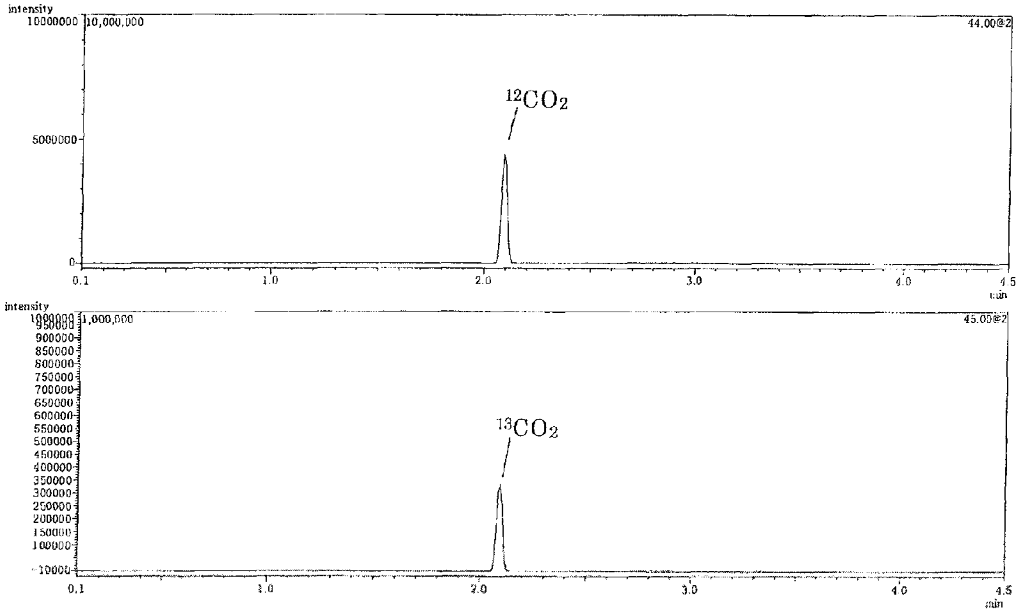
FIG. 44 Views showing the measured results by EIC chromatograph of $^{12}CO_2$ and $^{13}CO_2$ in the plasma of No. 4 rats treated with $^{13}CO_2$ mist.
Figure 45:
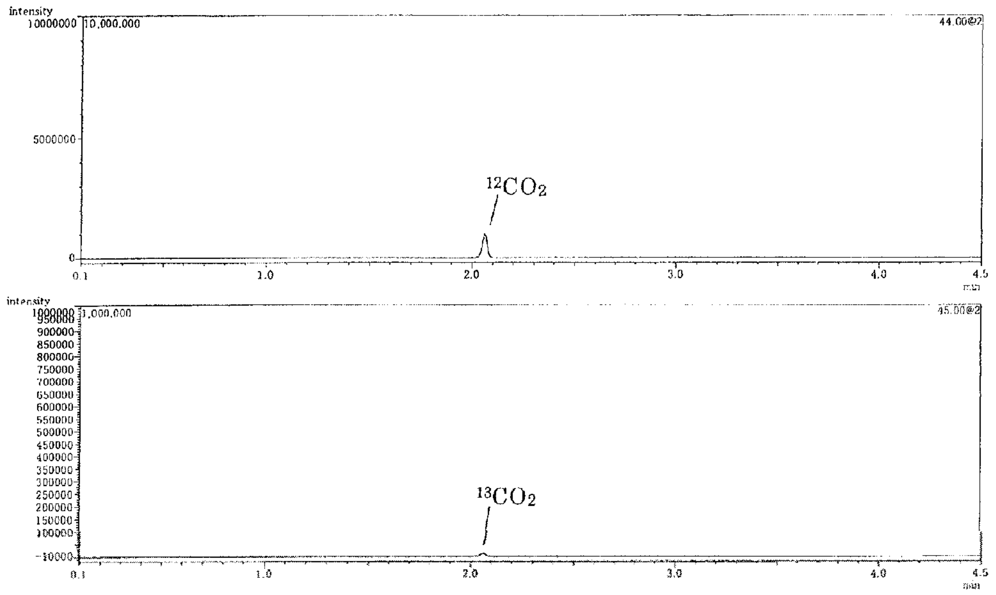
FIG. 45 Views showing the measured results by EIC chromatograph of $^{12}CO_2$ and $^{13}CO_2$ in the heart of non-treated No. 1 rats.
Figure 46:
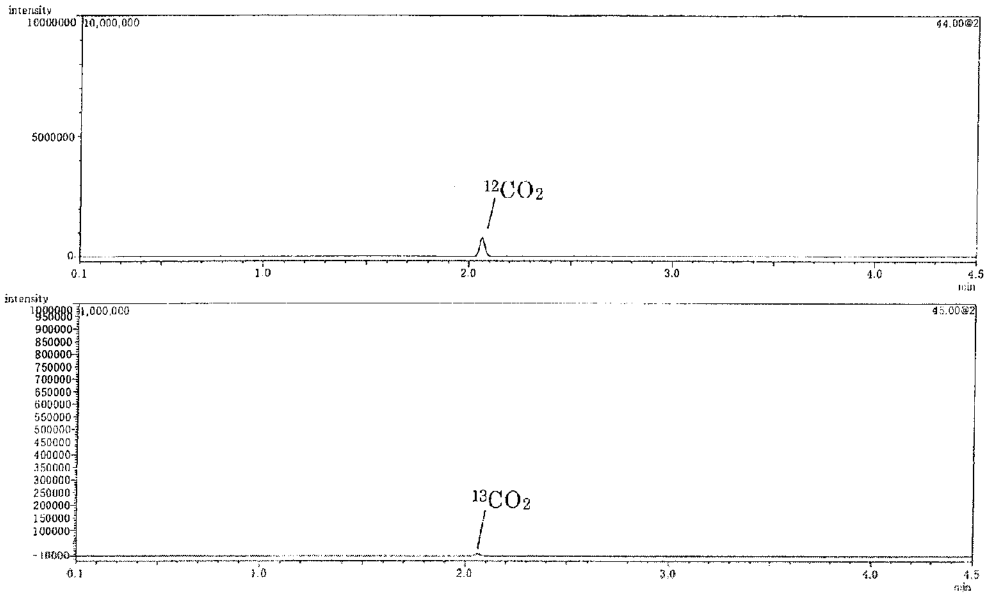
FIG. 46 Views showing the measured results by EIC chromatograph of $^{12}CO_2$ and $^{13}CO_2$ in the heart of non-treated No. 4 rats.
Figure 47:
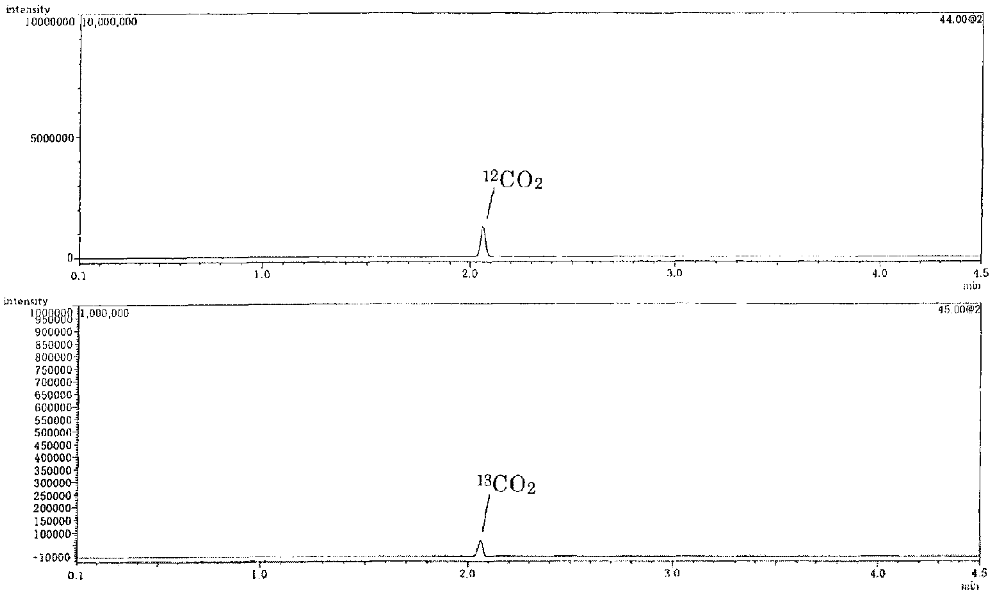
FIG. 47 Views showing the measured results by EIC chromatograph of $^{12}CO_2$ and $^{13}CO_2$ in the heart of No. 1 rats treated with $^{13}CO_2$ mist.
Figure 48:
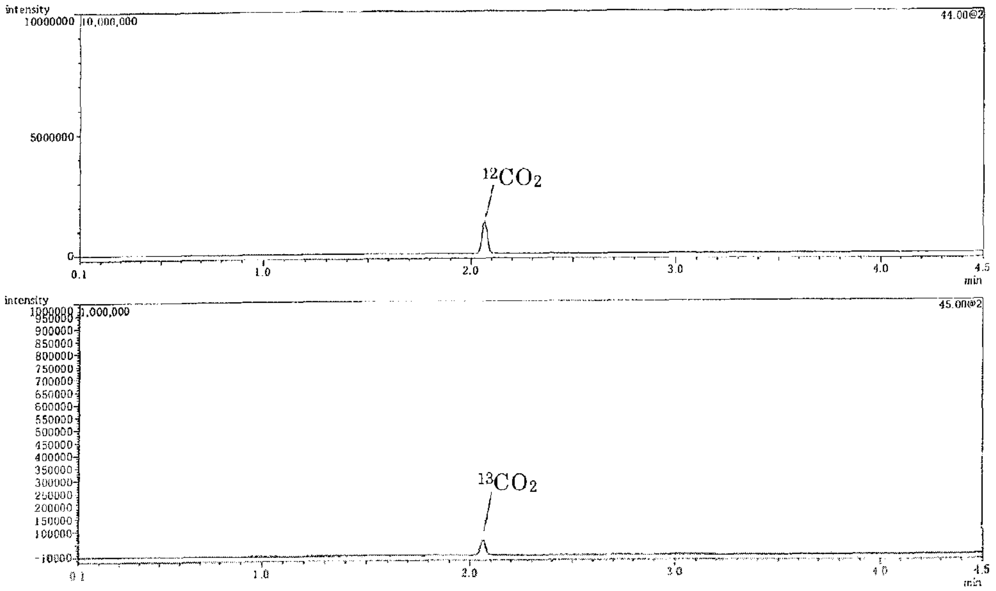
FIG. 48 Views showing the measured results by EIC chromatograph of $^{12}CO_2$ and $^{13}CO_2$ in the heart of No. 4 rats treated with $^{13}CO_2$ mist.
Figure 49:
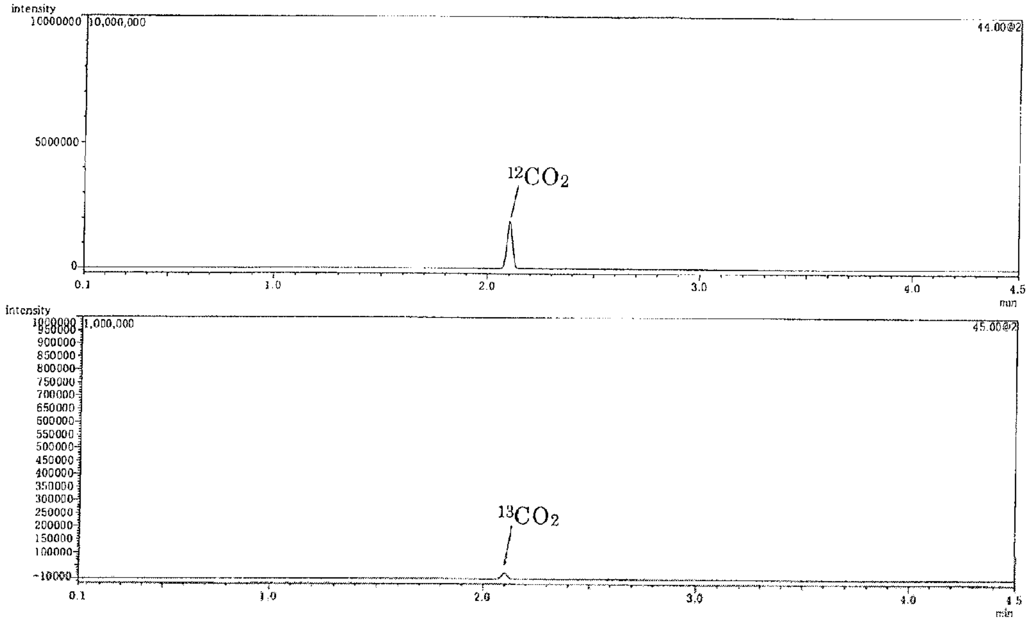
FIG. 49 Views showing the measured results by EIC chromatograph of $^{12}CO_2$ and $^{13}CO_2$ in the livers of non-treated No. 1 rats.
Figure 50:
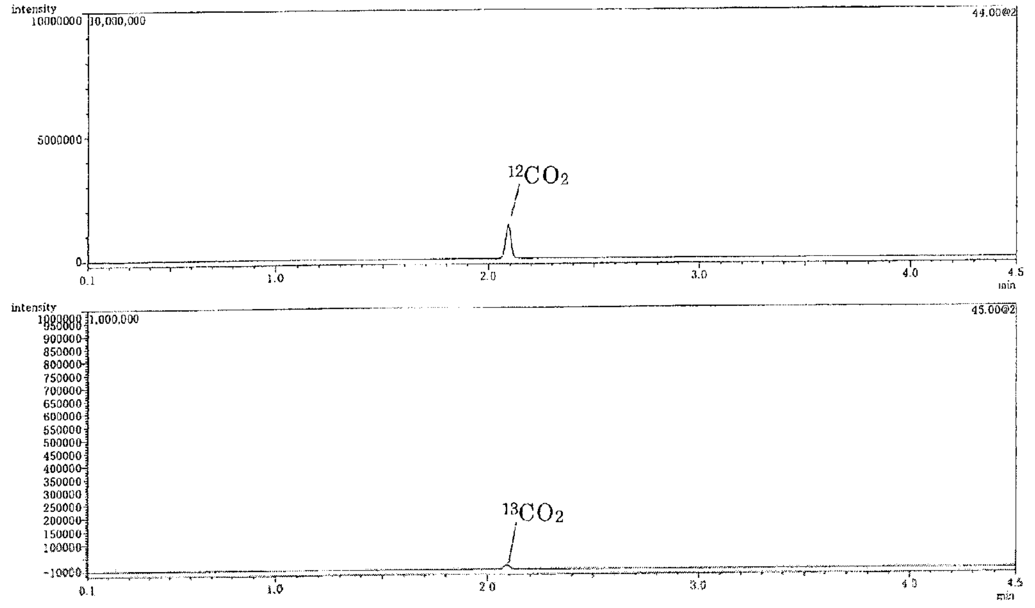
FIG. 50 Views showing the measured results by EIC chromatograph of $^{12}CO_2$ and $^{13}CO_2$ in the livers of non-treated No. 4 rats.
Figure 51:
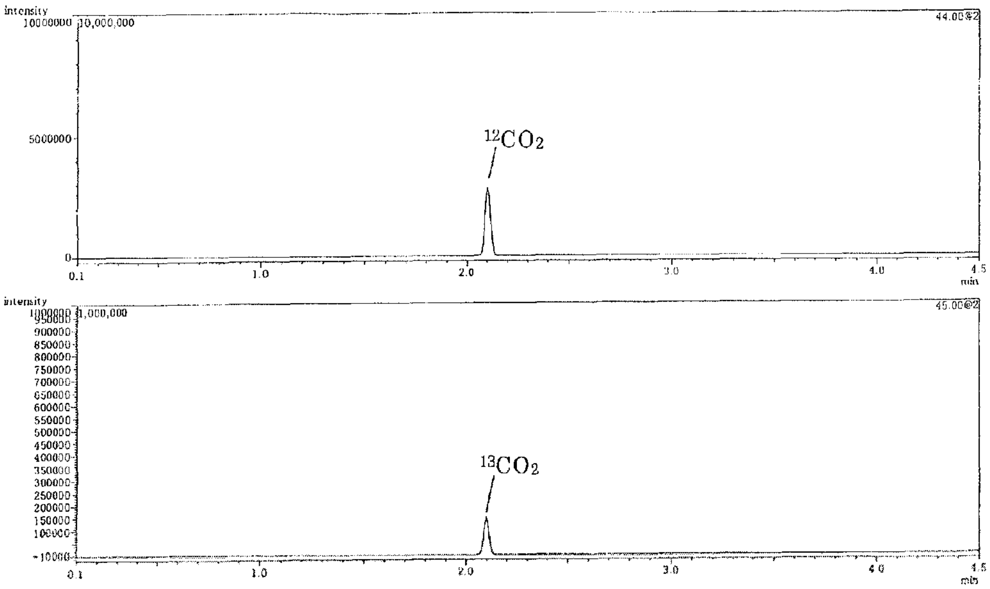
FIG. 51 Views showing the measured results by EIC chromatograph of $^{12}CO_2$ and $^{13}CO_2$ in the livers of No. 1 rats treated with $^{13}CO_2$ mist.
Figure 52:
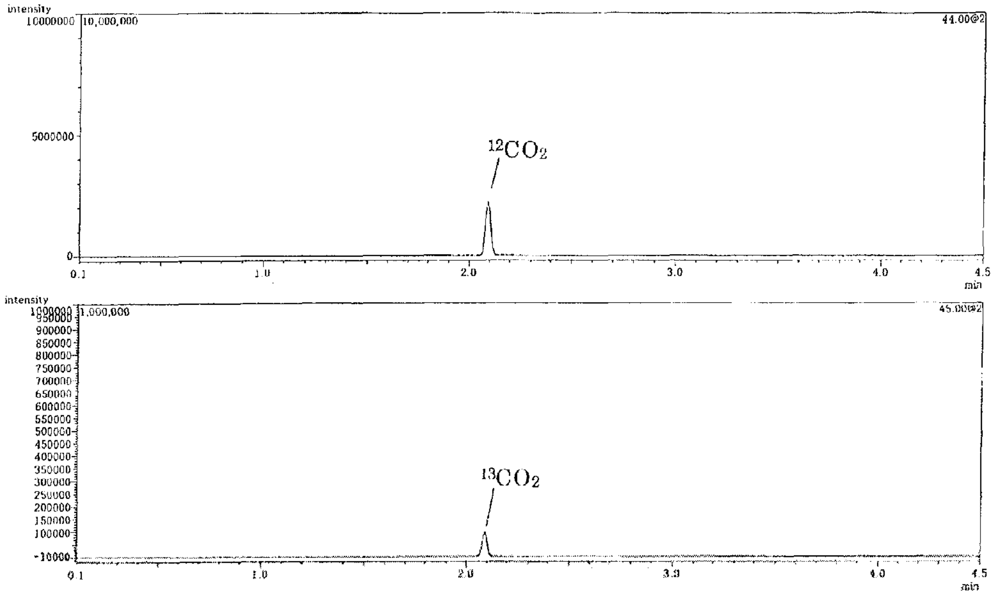
FIG. 52 Views showing the measured results by EIC chromatograph of $^{12}CO_2$ and $^{13}CO_2$ in the livers of No. 4 rats treated with $^{13}CO_2$ mist.
Figure 53:
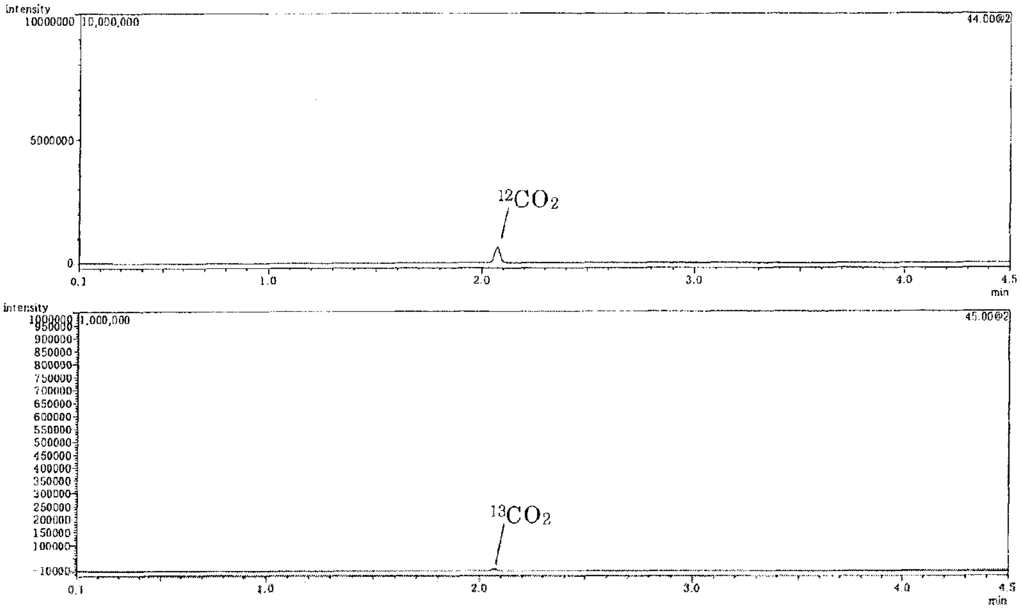
FIG. 53 Views showing the measured results by EIC chromatograph of $^{12}CO_2$ and $^{13}CO_2$ in the muscles of non-treated No. 1 rats.
Figure 54:
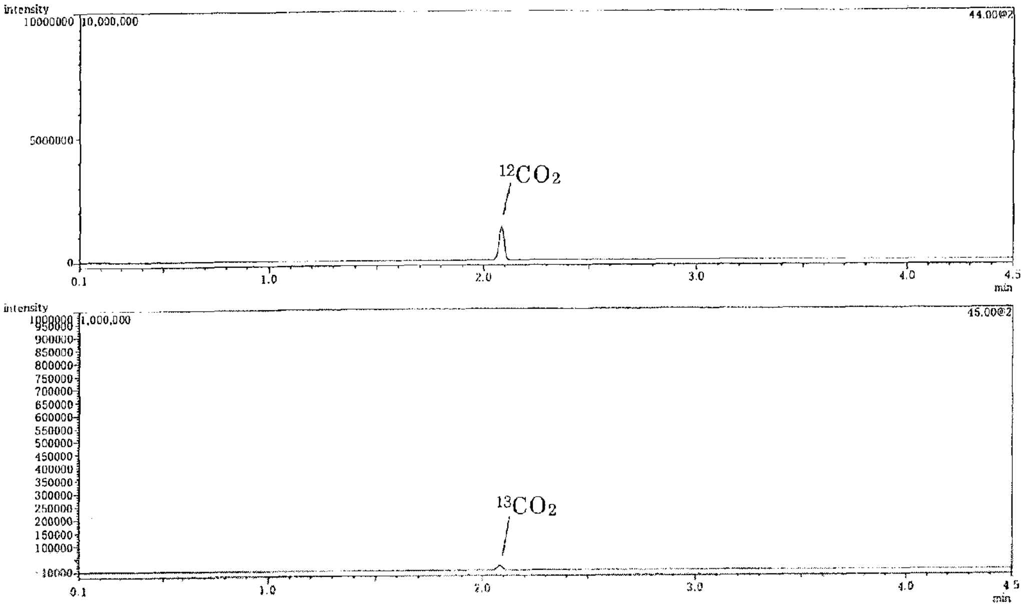
FIG. 54 Views showing the measured results by EIC chromatograph of $^{12}CO_2$ and $^{13}CO_2$ in the muscles of non-treated No. 4 rats.
Figure 55:
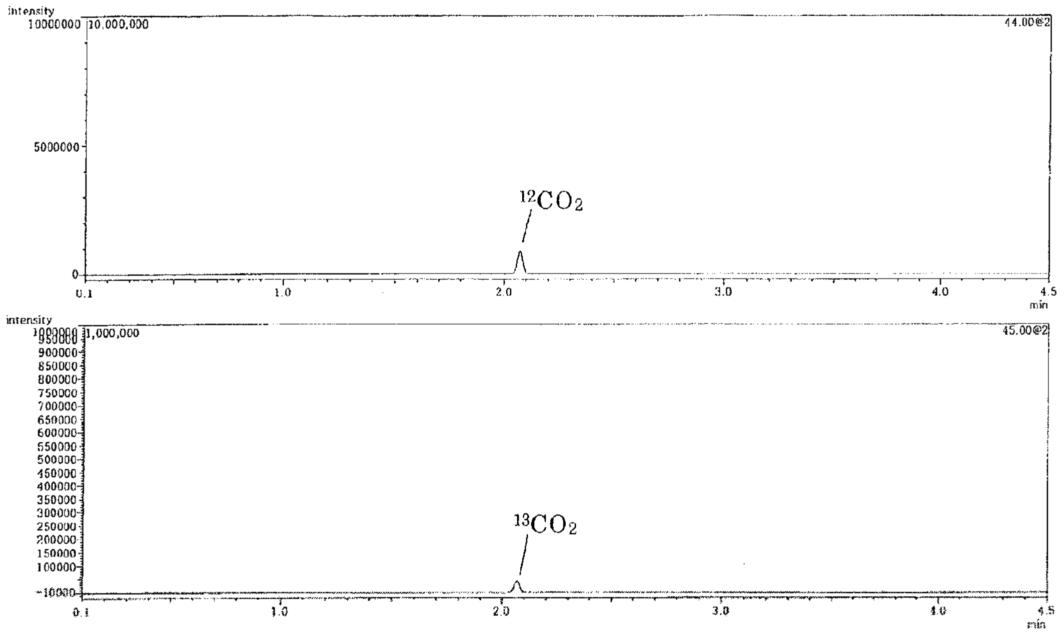
FIG. 55 Views showing the measured results by EIC chromatograph of $^{12}CO_2$ and $^{13}CO_2$ in the muscles of No. 1 rats treated with $^{13}CO_2$ mist.
Figure 56:
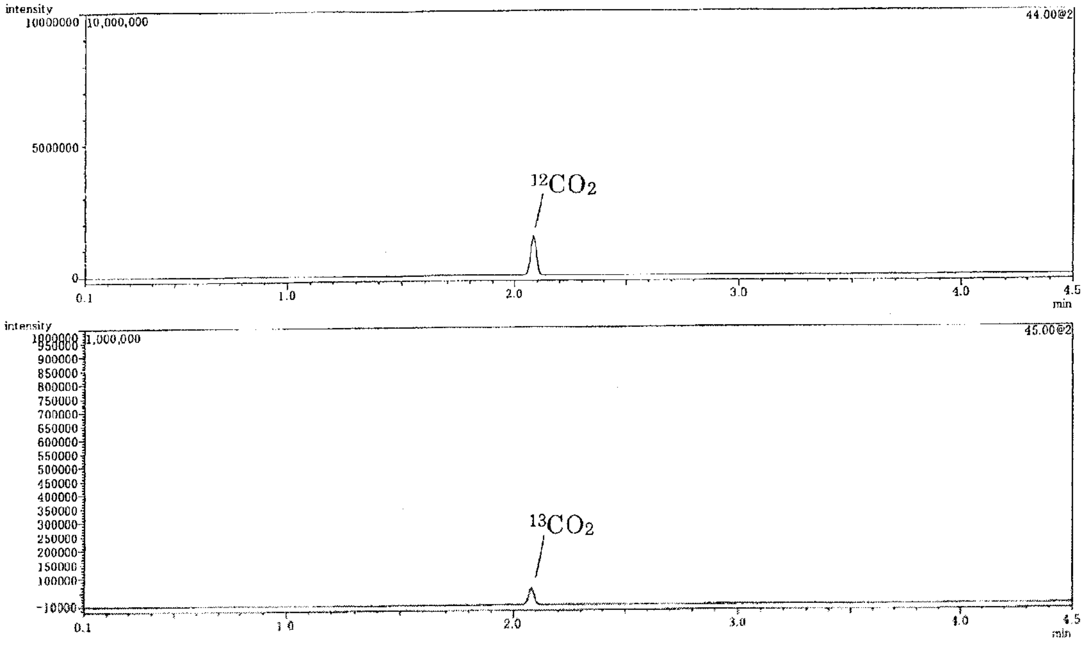
FIG. 56 Views showing the measured results by EIC chromatograph of $^{12}CO_2$ and $^{13}CO_2$ in the muscles of No. 4 rats treated with $^{13}CO_2$ mist.

To give another example, the chromatograph of FIG. 43 shows the volume of $^{12}CO_2$ in the plasma of the $^{13}CO_2$ mist-treated No. 1 on the upper stage and the volume of $^{13}CO_2$ in the plasma on the lower stage, and these determined results are divided by the volume of the plasma. Table 22 shows that the volume of $^{12}CO_2$ per mass of the found plasma is 960 (μg/g) and the volume of $^{13}CO_2$ is 59 (μg/g).

Thus, with respect to Table 22, the measured results of $^{12}CO_2$ and $^{13}CO_2$ in the chromatograph of the plasmas, hearts, livers and muscles of the non-treated and $^{13}CO_2$ mist-treated rats, were determined with the $CO_2$ analytical curve of m/z44, and the determined results were divided with the volume of the plasma, and Table 22 shows the volumes of $^{12}CO_2$ and $^{13}CO_2$ per mass of the found plasma.

By the way, the determined results shown in Table 22 are the values calculated by using the $CO_2$ analytical curve of m/z44, and concerning $^{13}CO_2$, the values contain the natural isotope (m/z45) existing in $CO_2$ derived from respiration. Therefore, Table 23 shows the detected values of $^{13}CO_2$ corrected by deducting the natural isotope (m/z45) existing in $CO_2$ derived from respiration from $^{13}CO_2$ based on the results shown in Table 22.

TABLE 23

Unit: μg/g

| Processing | | Samples: Plasma $^{13}CO_2$ | Heart $^{13}CO_2$ | Liver $^{13}CO_2$ | Muscle $^{13}CO_2$ |
|---|---|---|---|---|---|
| Non-Processing | No. 1 | <2.5 | <2.5 | <2.5 | <2.5 |
| | No. 2 | <2.5 | <2.5 | <2.5 | <2.5 |
| $^{13}CO_2$ | No. 1 | 48 | 22 | 21 | 6.5 |
| Mist-Treating | No. 2 | 55 | 16 | 14 | 8.0 |
| Minimum Limit of Determination | | 2.5 | 2.5 | 2.5 | 2.5 |

The calculating expression at this time is shown by a following formula, since the natural isotopic ratio (m/z44:m/z45) of $CO_2$ is 0.984:0.0113.

$$^{13}CO_2 \text{ detecting volume(collection value)} = {}^{13}CO_2 \text{ detecting value} - {}^{12}CO_2 \text{ detecting value} \times 0.0113/0.984.$$

Table 23 shows "less 2.5 μg/g" in the determined lower limits of the detected values of $^{13}CO_2$ of the plasmas, hearts, livers and muscles of the No. 1 and No. 2 rats not having been treated with the carbon dioxide gas mist pressure bath treatment, and this "less 2.5 μg/g" is lower by far than the detected values of $^{13}CO_2$ of the same tissues of the of the No. 1 and No. 2 treated rats.

FIGS. 57 to 62 show the graphs of gathering $^{12}CO_2$ detecting volumes and $^{13}CO_2$ detecting volumes (corrected values) classifying the samples and the treating ways.

Figure 57:
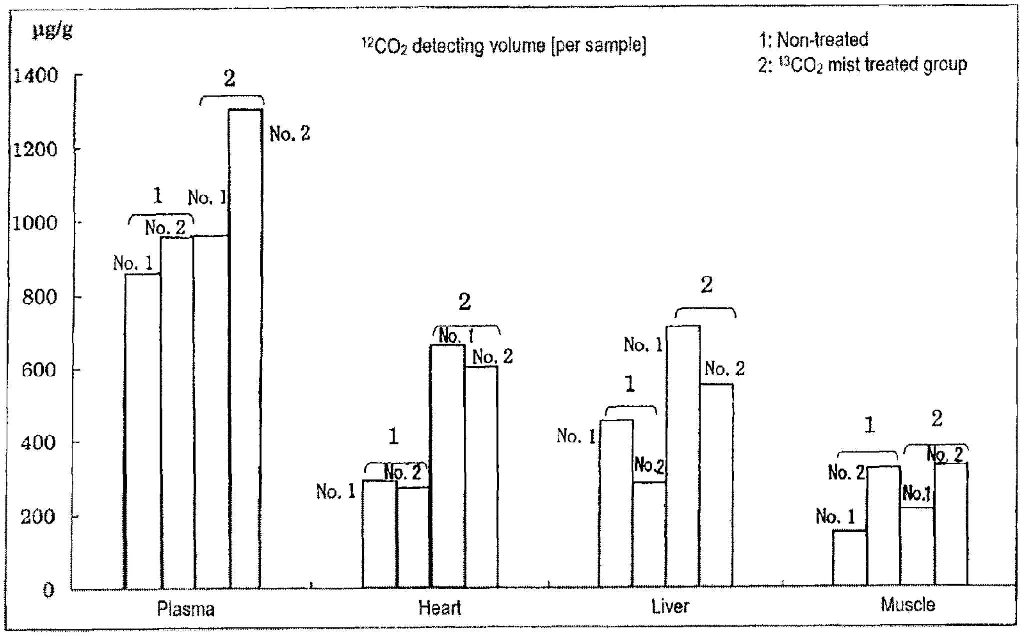
FIG. 57 A view showing detecting amounts per samples with $^{12}CO_2$ in the bar graphs.

FIG. 57 shows, with the bar graphs, the respective $^{12}CO_2$ detected volumes of the non-treated No. 1, the non-treated No. 2, the $^{13}CO_2$ mist treated No. 1 and the $^{13}CO_2$ mist treated No. 2, classifying the specimens of the plasmas, hearts, livers and muscles. In this graph, if comparing the $^{12}CO_2$ detecting volumes of the non-treatments and the $^{13}CO_2$ mist treatments, it is found that although the detected volumes of $^{12}CO_2$ in the respective tissues show the high tendency in the samples of the $^{13}CO_2$ mist treated specimens, any remarkable difference is not recognized.

Figure 58:
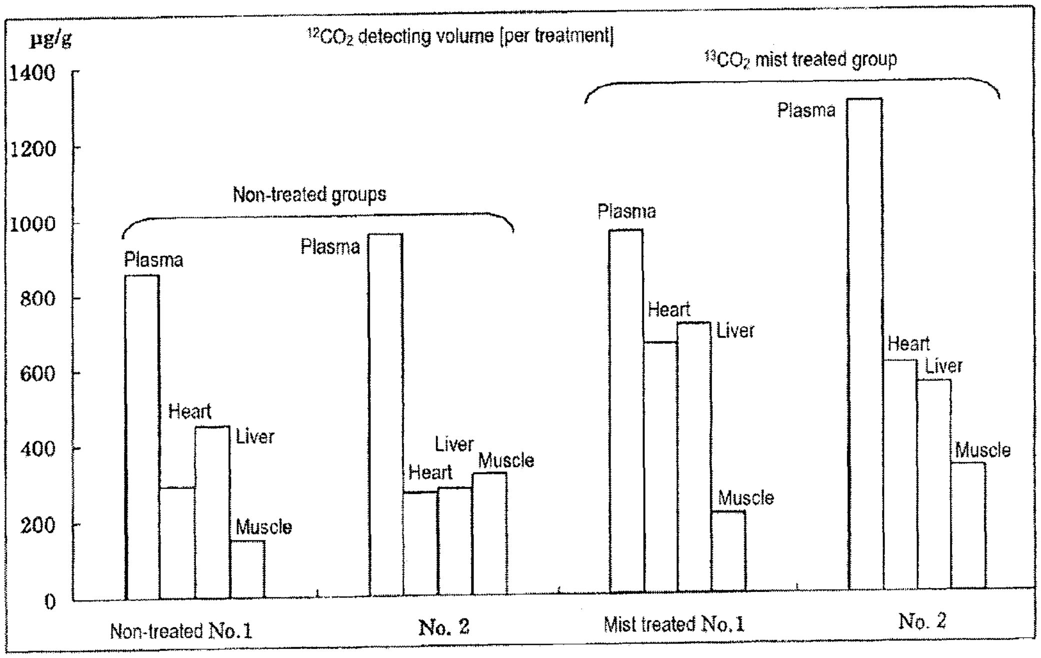
FIG. 58 A view showing detecting amounts per treating processes with $^{12}CO_2$ in the bar graphs.

FIG. 58 shows, with the bar graphs, in FIG. 57, the respective $^{12}CO_2$ detected volumes of the non-treated No. 1, the non-treated No. 2, the $^{13}CO_2$ mist treated No. 1 and the $^{13}CO_2$ mist treated No. 2, classifying the specimens of the plasmas, hearts, livers and muscles. Also in this graph, any remarkable difference is not recognized.

Figure 59:
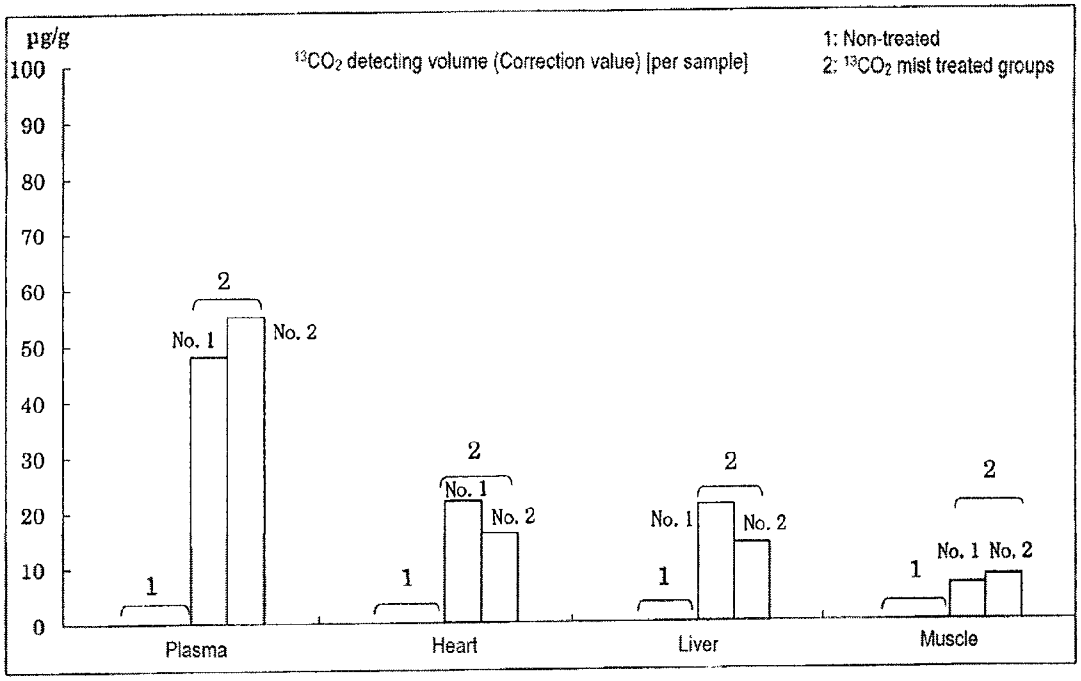
FIG. 59 A view showing detecting amounts per samples with $^{13}CO_2$ in the bar graphs.

FIG. 59 shows, with the bar graphs, the respective $^{13}CO_2$ detected volumes (corrected values) of the non-treated No. 1, the non-treated No. 2, the $^{13}CO_2$ mist treated No. 1 and the $^{13}CO_2$ mist treated No. 2, classifying the specimens of the plasmas, hearts, livers and muscles. This graph shows that in the case of the non-treatment, the volume of $^{13}CO_2$ was scarcely detected, and in the case of performing the $^{13}CO_2$ treatment, $^{13}CO_2$ was effectively detected in each of the tissues of the plasmas, hearts, livers and muscles, and shows the carbon dioxide gas mist pressure bath was effectively treated.

Figure 60:
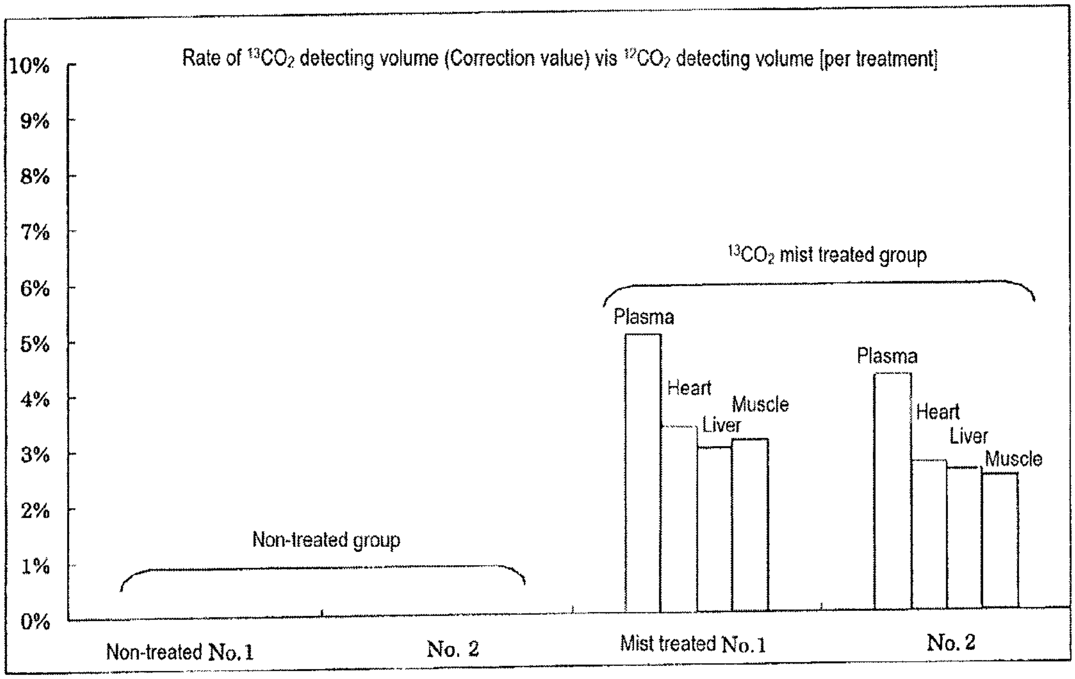
FIG. 60 A view showing detecting amounts per treating processes with $^{13}CO_2$ in the bar graphs.

FIG. 60 shows, with the bar graphs, in FIG. 59, the respective $^{13}CO_2$ detected volumes of the non-treated No. 1, the non-treated No. 2, the $^{13}CO_2$ mist treated No. 1 and the $^{13}CO_2$ mist treated No. 2, classifying the specimens of the plasmas, hearts, livers and muscles. Also this graph shows that, in the non-treated, the volume of $^{13}CO_2$ is scarcely detected, but in the $^{13}CO_2$ mist treatment, the $^{13}CO_2$ mist is effectively detected in each of the tissues.

Figure 61:
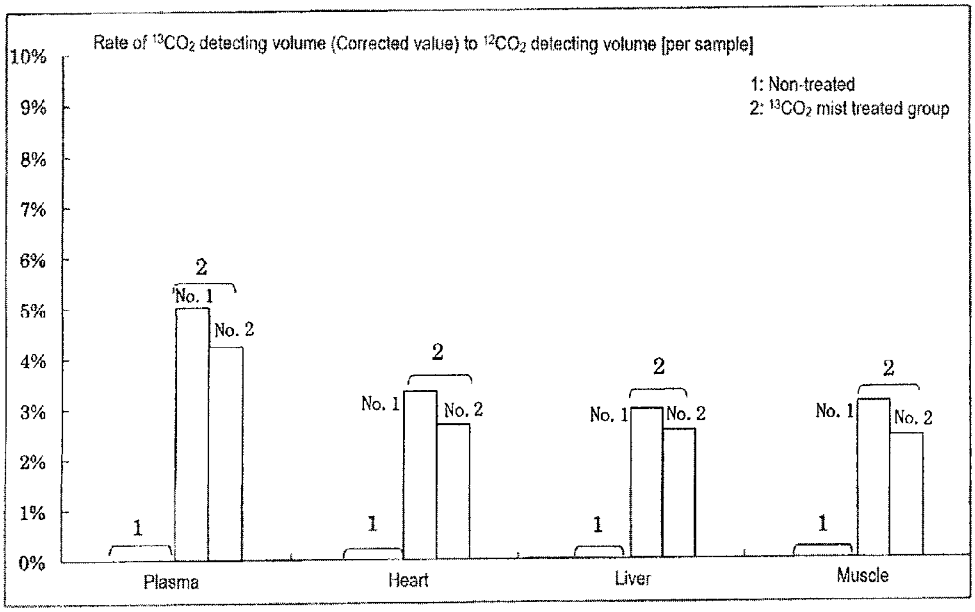
FIG. 61 A view showing detecting amounts per specimens with $^{13}CO_2$ vis $^{12}CO_2$ in the bar graphs.

FIG. 61 shows, with the bar graphs, respectively the rate of the $^{13}CO_2$ detecting volume (collected value) to each of the detecting volumes of the non-treated No. 1, the non-treated No. 2, the $^{13}CO_2$ treated No. 1 and the $^{13}CO_2$ treated No. 2. This graph shows that, in the non-treated, $^{13}CO_2$ was scarcely detected to the detecting volume of $^{12}CO_2$. In the case of performing the $^{13}CO_2$ treatment, $^{13}CO_2$ was effectively detected in each of the tissues of the plasmas, hearts, livers and muscles, and shows the carbon dioxide gas mist pressure bath was effectively treated.

Figure 62:
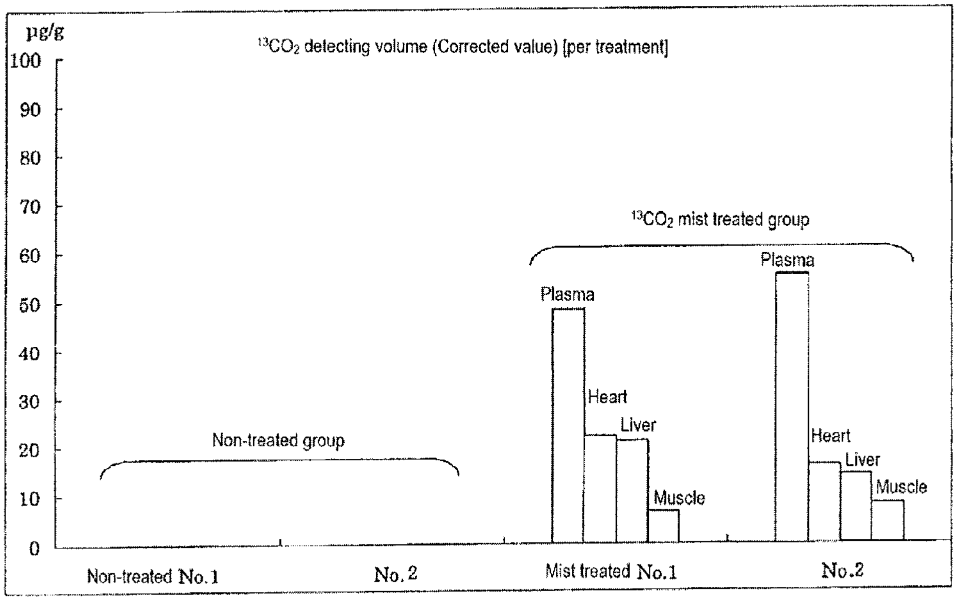
FIG. 62 A view showing detecting amounts per treating processes with $^{13}CO_2$ vis $^{12}CO_2$ in the bar graphs.

FIG. 62 shows, with the bar graph, in FIG. 61, the rate of the detecting volumes (collected value) of $^{13}CO_2$ to the respective detected volumes of the non-treated No. 1, the non-treated No. 2, the $^{13}CO_2$ treated No. 1 and the $^{13}CO_2$ treated No. 2, specifying the non-treatment and the $^{13}CO_2$ mist treatment. It is seen from this graph that, in the non-treated case, $^{13}CO_2$ was scarcely detected with respect to the detecting volume of $^{12}CO_2$, but if carrying out the $^{13}CO_2$ mist treatment, the $^{13}CO_2$ mist was effectively detected in the tissues of the plasmas, hearts, livers and muscles.

Next, Table 24 arranges the experimented results of the test specimens 1 to 4 of the non-treated rats and the test specimens 1 to 4 of the $^{13}CO_2$ treated rats.

TABLE 24

(μg/g)

| | | Plasma | | | Heart | | | Liver | | | Skeletal Muscle | | |
|---|---|---|---|---|---|---|---|---|---|---|---|---|---|
| | Samples | $^{12}CO_2$ | $^{13}CO_2$ | Total $CO_2$ | $^{12}CO_2$ | $^{13}CO_2$ | Total $CO_2$ | $^{12}CO_2$ | $^{13}CO_2$ | Total $CO_2$ | $^{12}CO_2$ | $^{13}CO_2$ | Total $CO_2$ |
| Non- | Specimen 1 | 861 | 7.6 | 868.6 | 293.3 | 3.3 | 296.6 | 450.7 | 4.7 | 455.4 | 152 | 1.5 | 153.5 |
| Treated | Specimen 2 | 965 | 8.4 | 973.4 | 268.6 | 3.1 | 271.7 | 280.4 | 3.1 | 283.5 | 317.4 | 3.5 | 320.9 |
| Group | Specimen 3 | 983.8 | 6.8 | 990.6 | 604.5 | 5.8 | 610.3 | 689.1 | 5.7 | 694.8 | 217.1 | 2.2 | 219.3 |
| | Specimen 4 | 859.2 | 5.8 | 865.0 | 424.9 | 4.3 | 429.2 | 529.6 | 4.7 | 534.3 | 318.9 | 3.1 | 322.0 |
| | Average | 917.25 | 7.15 | 924.4 | 397.83 | 4.1 | 402.0 | 487 | 4.6 | 492.0 | 251.35 | 2.58 | 253.9 |
| $^{13}CO^2$ | Specimen 1 | 960 | 59 | 1018.8 | 657.6 | 29.4 | 687.0 | 706.5 | 29.1 | 735.6 | 207.4 | 8.9 | 216.3 |
| Mist | Specimen 2 | 1306 | 70 | 1376.2 | 598.4 | 23.1 | 621.5 | 545.4 | 19.8 | 565.2 | 332.4 | 11.8 | 344.2 |
| Treated | Specimen 3 | 774.6 | 38 | 812.5 | 608.3 | 19.8 | 628.1 | 482.8 | 14.4 | 497.2 | 561.4 | 20.0 | 581.4 |
| Group | Specimen 4 | 823.7 | 29 | 852.7 | 610.3 | 15 | 625.3 | 626.5 | 14.3 | 640.8 | 275.5 | 8.2 | 283.7 |
| | Average | 966 | 49.0 | 1015.05 | 619 | 21.8 | 640.5 | 590 | 19.4 | 609.7 | 344.18 | 12.2 | 356.4 |
| Treated/Non-Treated | | 1.05 | 6.85 | 1.10 | 1.56 | 5.29 | 1.59 | 1.21 | 4.26 | 1.24 | 1.37 | 4.75 | 1.40 |

In Table 24, the ratio of the average values of $^{13}CO_2$ and $^{12}CO_2$ detected in the respective tissues of the specimens 1 to 4 of the non-treated groups is approximately 0.01 (for example, in the case of the plasma, 7.15/917.25=0.008) showing almost the same value as in the atmosphere, and on the other hand, the same ratio in the $^{13}CO_2$ treating groups (for example, in the case of the plasma, 49.0/966=0.05) is more than 6 times of the non-treated groups in the plasma, and more than 3 times of the non-treated groups in the hearts, livers and skeletal muscles.

The ratio of the average values of the total $CO_2$ detected in the respective tissues of the specimens 1 to 4 of the non-treated groups to the average values of the total $CO_2$ detected in the respective tissues of the specimens 1 to 4 of the $^{13}CO_2$ treated groups slightly increased in the plasma as 1.10 (015.05/924.4) times, but in the hearts, increased as 1.59 (640.5/402.0) times, and this fact is considered as contributing to acceleration of metabolism function.

The above analyzing results show that, if making the rats a cutaneous respiration of $^{13}CO_2$ by the carbon dioxide gas mist pressure bath treatment by the present invention, $^{13}CO_2$ is effectively distributed in a body organ, and this fact has proved that depending on the carbon dioxide gas mist pressure bath treatment by the present invention, carbon dioxide is taken effectively into the living body.

Thus, by causing the carbon dioxide gas mist to contact the skin and mucous membrane of the living organism at predetermined pressure (above the internal pressure of the living organism), thereby to heighten the concentration of carbon dioxide taken into the blood so that carbon dioxide does not cease to advance till reaching the heart, an ischemic region of the myocardial infarction diseased part can be cured and blood vessels of the heart muscle can be expanded to improve conditions of myocardial infarction.

As having explained in detail, in the present carbon dioxide pressure bath method, the following steps (a) to (d) are continued at least once per day for four weeks, that is, a step (a) of producing a carbon dioxide gas mist by pulverizing and dissolving carbon dioxide gas into a liquid, and forming this liquid into a mist; a step (b) of spraying the carbon dioxide gas mist into a carbon dioxide gas mist-enclosing means for enclosing the living organism in an air tight state; a step (c) of expelling gas existing in the carbon dioxide gas mist-enclosing means into the outside, if necessary in parallel with the step (b), in order to maintain the pressure of gas within the carbon dioxide gas mist-enclosing means at or above a prescribed value being higher than the atmospheric pressure; and a step (d) of continuing such a step of supplying, for at least 20 minutes, the carbon dioxide mist into the carbon dioxide gas mist-enclosing means. Thereby, carbon dioxide is contacted to the skin and mucous membrane of a living organism directly or through clothing, thereby to improve or promote circulation of the blood in the myocardial region, and furthermore to prevent, improve or cure myocardial infarction.

INDUSTRIAL APPLICABILITY

The present invention relates to the carbon dioxide gas mist pressure bath method and the carbon dioxide gas mist pressure bath apparatus for preventing, improving or curing myocardial infarction by contacting carbon dioxide to the skin and mucous membrane of the living organism directly or through clothing under a predetermined condition, thereby to improve or promote circulation of the blood in the myocardial region, and has the industrial applicability.

EXPLANATION OF REFERENCE NUMERALS AND MARKS

10, 10A: carbon dioxide gas mist pressure bath apparatus
11: carbon dioxide gas mist generating and supplying means
111: carbon dioxide supply means
112: liquid supply means
113: carbon dioxide gas mist generating means
113': carbon dioxide gas mist generating means (atomizing system)
14: liquid storage
115A: nozzle
115B: liquid suction pipe
116: baffle
117A: carbon dioxide supply part
117B: carbon dioxide inlet part
118A: carbon dioxide gas mist collection part
118B: carbon dioxide gas mist outlet part
119: carbon dioxide gas mist supply pipe
12: pressure bath cover
121: cove main body
122: opening and closing part
123: open part
124: inlet port
125: outlet port
13: concentration meter
14: control device
141: flow valve
142: switch valve
150: pressure bath cover
151: manometer
20: carbon dioxide gas mist pressure apparatus
21A, 21B: carbon dioxide gas mist generating and supplying means
22: horse pressure bath cover
221: cover main body
222: opening and closing part
223: opening part
224A, 224B: inlet ports
225: outlet port
30: carbon dioxide gas mist pressure bath apparatus
32: pressure bath cover
321: cover main body
322: upper part
323: bottom part
324: side part
325: gate
325A: handle
326: opening
327: leakage prevention means
327A: opening
328: inlet port
329: outlet port
32*a*: pressure bath cover for standing
32*b*: pressure bath cover for lying
321*a*, 321*b*: cover main bodies
325*a*, 325*b*: gates
326*a*, 326*b*: openings
327*a*, 327*b*: leakage prevention means
328*a*, 328*b*: inlet ports
329*a*, 329*b*: outlet ports
330: chair

The invention claimed is:

1. A carbon dioxide gas mist pressure bath apparatus for preventing, improving or curing a myocardial infarction by contacting a carbon dioxide gas mist to a skin and a mucous membrane of a living organism directly or through a clothing, thereby to improve or promote a circulation of a blood, comprising:
   - a carbon dioxide gas mist-enclosing unit for enclosing the living organism under a sealing condition;
   - a gas supply unit for supplying a carbon dioxide gas;
   - a carbon dioxide gas mist generating and supplying unit for pulverizing and dissolving the carbon dioxide gas supplied from the gas supply unit into a liquid stored therein to generate the carbon dioxide gas mist, and supplying the carbon dioxide gas mist into the carbon dioxide gas mist-enclosing unit, the carbon dioxide gas mist generating and supplying unit including a connection part connected to the gas supply unit at one end portion thereof, a branch part diverging a gas flow from the connection part into first and second gas flows, a liquid storage storing the liquid at a lower part thereof, a nozzle extending upwardly from a bottom portion of the liquid storage and communicating with the first gas flow diverged at the branch part, a liquid suction pipe forming member covering the nozzle to define a liquid sending pipe formed between the nozzle and the liquid suction pipe forming member, the liquid sending pipe sending the liquid stored in the liquid storage to one end of the nozzle, a baffle arranged apart from the one end of the nozzle and colliding the gas and the liquid blown up by the first gas flow discharged from the nozzle to generate the gas mist, a confluent part arranged at an upper part of the baffle to mix the second gas flow diverged at the branch part into the gas mist from an upper side thereof, a gas introduction part extending from the branch part toward the confluent part and guiding the second gas flow diverged at the branch part to the confluent part, and a gas mist discharging part connected to the carbon dioxide gas mist-enclosing unit and discharging the gas mist from the confluent part to the carbon dioxide gas mist-enclosing unit;

an exhausting device for exhausting the gas in the carbon dioxide gas mist-enclosing unit to an outside thereof; and a control device for, while exhausting the gas in the carbon dioxide gas mist-enclosing unit to the outside thereof, controlling a supplying amount of the carbon dioxide gas mist from the carbon dioxide gas mist generating and supplying unit, such that an air pressure within the carbon dioxide gas mist-enclosing unit is set to be within a predetermined range, wherein the connection part, the branch part, the liquid storage, the nozzle, the liquid suction pipe forming member, the liquid sending pipe, the baffle, the confluent part, the gas introduction part, and the gas mist discharging part of the carbon dioxide gas mist generating and supplying unit are integrally formed.

2. The carbon dioxide gas mist pressure bath apparatus as set forth in claim 1, further comprising a concentration detecting unit for measuring a concentration of the carbon dioxide gas mist in the carbon dioxide gas mist-enclosing unit, wherein the control device controls the supplying amount of the carbon dioxide gas mist such that the concentration of the carbon dioxide gas mist is to be at a predetermined value or more.

3. The carbon dioxide gas mist pressure bath apparatus as set forth in claim 2, further comprising an air pressure detecting unit for measuring an air pressure in the carbon dioxide gas mist-enclosing unit, wherein the control device controls the supplying amount of the carbon dioxide gas mist such that the air pressure in the carbon dioxide gas mist-enclosing unit is to be at a predetermined value or more.

4. The carbon dioxide gas mist pressure bath apparatus as set forth in claim 1, wherein the carbon dioxide gas mist generating and supplying unit generates the carbon dioxide gas mist having a diameter not more than 10 μm.

5. The carbon dioxide gas mist pressure bath apparatus as set forth in claim 1, wherein the control unit maintains a concentration of the carbon dioxide gas mist within the carbon dioxide gas mist-enclosing unit to be 60% or more.

6. The carbon dioxide gas mist pressure bath apparatus as set forth in claim 3, wherein the control unit maintains the air pressure in the carbon dioxide gas mist-enclosing unit to be 1.0 to 2.5 atmospheric pressure.

7. The carbon dioxide gas mist pressure bath apparatus as set forth in claim 1, wherein the carbon dioxide gas mist-enclosing unit is a foldable cover type, a bag type or a fixedly stationary box type, which is formed with a space for sealing therein the carbon dioxide gas mist.

8. The carbon dioxide gas mist pressure bath apparatus as set forth in claim 7, wherein the carbon dioxide gas mist-enclosing unit comprises a carbon dioxide gas mist inlet port having a check valve thereinside, an outlet port discharging the gas stored thereinside, a doorway for getting in and out the living body, and an opening portion for exposing a head of the living body.

9. The carbon dioxide gas mist pressure bath apparatus as set forth in claim 8, wherein the opening portion has a leakage prevention member for preventing the carbon dioxide gas mist leaking from a space between the opening portion and the living body.

10. The carbon dioxide gas mist pressure bath apparatus as set forth in claim 7, wherein the carbon dioxide gas mist-enclosing unit is the box type having a chair thereinside.

11. The carbon dioxide gas mist pressure bath apparatus as set forth in claim 1, wherein the carbon dioxide gas mist generating and supplying unit includes a path extending between the connection part and the nozzle, the gas introduction part is diverged from the gas discharge path at the branch part and extends toward the confluent part through a side portion of the carbon dioxide gas mist generating and supplying unit, the confluent part is connected to one end of the gas introduction part and to surround the baffle, and the gas mist discharging part is arranged adjacent to the confluent part and is communicated with the confluent part at one end thereof to discharge the gas mist from the confluent part.

* * * * *